(12) United States Patent
Hoge et al.

(10) Patent No.: US 11,202,793 B2
(45) Date of Patent: Dec. 21, 2021

(54) HIGH PURITY RNA COMPOSITIONS AND METHODS FOR PREPARATION THEREOF

(71) Applicant: ModernaTX, Inc., Cambridge, MA (US)

(72) Inventors: Stephen Hoge, Brookline, MA (US); William Issa, Dedham, MA (US); Edward J. Miracco, Arlington, MA (US); Jennifer Nelson, Brookline, MA (US); Amy E. Rabideau, Waltham, MA (US); Gabor Butora, Martinsville, NJ (US)

(73) Assignee: ModernaTX, Inc., Cambridge, MA (US)

( * ) Notice: Subject to any disclaimer, the term of this patent is extended or adjusted under 35 U.S.C. 154(b) by 410 days.

(21) Appl. No.: 16/333,330

(22) PCT Filed: Sep. 14, 2017

(86) PCT No.: PCT/US2017/051674
§ 371 (c)(1),
(2) Date: Mar. 14, 2019

(87) PCT Pub. No.: WO2018/053209
PCT Pub. Date: Mar. 22, 2018

(65) Prior Publication Data
US 2019/0247417 A1 Aug. 15, 2019

Related U.S. Application Data

(60) Provisional application No. 62/394,711, filed on Sep. 14, 2016.

(51) Int. Cl.
*A61K 31/7105* (2006.01)
*C07K 14/505* (2006.01)
*C12P 19/34* (2006.01)
*A61P 33/00* (2006.01)
*A61P 31/12* (2006.01)
*A61P 31/04* (2006.01)
*A61P 35/00* (2006.01)
*C12N 15/10* (2006.01)
*G01N 33/68* (2006.01)

(52) U.S. Cl.
CPC .......... *A61K 31/7105* (2013.01); *A61P 31/04* (2018.01); *A61P 31/12* (2018.01); *A61P 33/00* (2018.01); *A61P 35/00* (2018.01); *C07K 14/505* (2013.01); *C12N 15/10* (2013.01); *C12P 19/34* (2013.01); *G01N 33/6851* (2013.01)

(58) Field of Classification Search
CPC ............ A61K 2039/53; A61K 2300/00; C12N 9/1247; C12N 15/67; C12N 15/1062; C12Q 1/68; C12Q 1/6844; C12Q 527/00; C12Q 2549/00

USPC ...................... 435/6.1, 91.1, 91.31; 536/23.1
See application file for complete search history.

(56) References Cited

U.S. PATENT DOCUMENTS

| | | |
|---|---|---|
| 5,256,555 A | 10/1993 | Milburn et al. |
| 5,756,264 A | 5/1998 | Schwartz et al. |
| 6,022,715 A | 2/2000 | Merenkova et al. |
| 6,096,503 A | 8/2000 | Sutcliffe et al. |
| 6,100,024 A | 8/2000 | Hudson et al. |
| 6,528,262 B1 | 3/2003 | Gilad et al. |
| 8,383,340 B2 | 2/2013 | Ketterer et al. |
| 8,710,200 B2 | 4/2014 | Schrum et al. |
| 8,754,062 B2 | 6/2014 | De Fougerolles et al. |
| 8,822,663 B2 | 9/2014 | Schrum et al. |
| 8,999,380 B2 | 4/2015 | Bancel et al. |
| 9,221,891 B2 | 12/2015 | Bancel et al. |
| 9,283,287 B2 | 3/2016 | Bancel et al. |
| 9,303,079 B2 | 4/2016 | Bancel et al. |
| 9,464,124 B2 | 10/2016 | Bancel et al. |
| 9,512,456 B2 | 12/2016 | Wang et al. |
| 9,533,047 B2 | 1/2017 | de Fougerolles et al. |
| 9,597,380 B2 | 3/2017 | Chakraborty et al. |
| 9,868,691 B2 | 1/2018 | Benenato et al. |
| 9,872,900 B2 | 1/2018 | Ciaramella et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,207,010 B2 | 2/2019 | Besin et al. |
| 10,232,055 B2 | 3/2019 | Kariko et al. |
| 10,273,269 B2 | 4/2019 | Ciaramella |

(Continued)

FOREIGN PATENT DOCUMENTS

| | | |
|---|---|---|
| EP | 2092064 B1 | 9/2010 |
| WO | WO 2002/48310 A2 | 6/2002 |

(Continued)

OTHER PUBLICATIONS

U.S. Appl. No. 16/036,318, filed Jul. 16, 2018, Ciaramella et al.

(Continued)

*Primary Examiner* — Jane J Zara
(74) *Attorney, Agent, or Firm* — Wolf, Greenfield & Sacks, P.C.

(57) ABSTRACT

The invention relates to improved RNA compositions for use in therapeutic applications. The RNA compositions are particularly suited for use in human therapeutic application (e.g., in RNA therapeutics). The RNA compositions are made by improved processes, in particular, improved in vitro-transcription (IVT) processes. The invention also relates to methods for producing and purifying RNA (e.g, therapeutic RNAs), as well as methods for using the RNA compositions and therapeutic applications thereof.

23 Claims, 51 Drawing Sheets
Specification includes a Sequence Listing.

(56) References Cited

U.S. PATENT DOCUMENTS

| | | |
|---|---|---|
| 10,286,086 B2 | 5/2019 | Roy et al. |
| 10,385,088 B2 | 8/2019 | Fraley et al. |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,526,629 B2 | 1/2020 | Rabideau et al. |
| 10,653,712 B2 | 5/2020 | Hoge |
| 10,653,767 B2 | 5/2020 | Ciaramella et al. |
| 10,695,419 B2 | 6/2020 | Ciaramella et al. |
| 10,857,105 B2 | 12/2020 | Benenato et al. |
| 10,925,958 B2 | 2/2021 | Ciaramella |
| 11,045,540 B2 | 6/2021 | Ciaramella |
| 11,103,578 B2 | 8/2021 | Ciaramella et al. |
| 2001/0001066 A1 | 5/2001 | Cezayirli et al. |
| 2001/0005506 A1 | 6/2001 | Cezayirli et al. |
| 2003/0165849 A1 | 9/2003 | Zhang et al. |
| 2006/0247195 A1 | 11/2006 | Ray |
| 2007/0281336 A1 | 12/2007 | Jendrisak et al. |
| 2008/0220471 A1 | 9/2008 | Davis et al. |
| 2010/0028943 A1 | 2/2010 | Thomas et al. |
| 2010/0048883 A1 | 2/2010 | Ketterer et al. |
| 2010/0291156 A1 | 11/2010 | Barner et al. |
| 2012/0301955 A1 | 11/2012 | Thomas et al. |
| 2013/0102034 A1 | 4/2013 | Schrum et al. |
| 2013/0236974 A1 | 9/2013 | De Fougerolles |
| 2013/0245103 A1 | 9/2013 | de Fougerolles et al. |
| 2013/0259923 A1 | 10/2013 | Bancel et al. |
| 2013/0266640 A1 | 10/2013 | De Fougerolles et al. |
| 2014/0142290 A1 | 5/2014 | Madden et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0378538 A1 | 12/2014 | Bancel |
| 2015/0051268 A1 | 2/2015 | Bancel et al. |
| 2015/0056253 A1 | 2/2015 | Bancel et al. |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2016/0024140 A1 | 1/2016 | Issa et al. |
| 2016/0024141 A1 | 1/2016 | Issa et al. |
| 2016/0032273 A1 | 2/2016 | Shahrokh et al. |
| 2016/0038612 A1 | 2/2016 | Hoge et al. |
| 2016/0243221 A1 | 8/2016 | Hoge et al. |
| 2016/0317647 A1 | 11/2016 | Ciaramella et al. |
| 2017/0043037 A1 | 2/2017 | Kariko et al. |
| 2017/0202979 A1 | 7/2017 | Chakraborty et al. |
| 2017/0204152 A1 | 7/2017 | Nelson et al. |
| 2017/0130255 A1 | 10/2017 | Wang et al. |
| 2017/0340724 A1 | 11/2017 | Ciaramella et al. |
| 2017/0340725 A1 | 11/2017 | Ciaramella et al. |
| 2018/0000953 A1 | 1/2018 | Almarsson et al. |
| 2018/0002393 A1 | 1/2018 | Bancel et al. |
| 2018/0028645 A1 | 2/2018 | Ciaramella et al. |
| 2018/0028664 A1 | 2/2018 | Besin et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0280496 A1 | 10/2018 | Ciaramella et al. |
| 2018/0289792 A1 | 10/2018 | Ciaramella et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0312549 A1 | 11/2018 | Ciaramella |
| 2018/0318409 A1 | 11/2018 | Valiante et al. |
| 2018/0363019 A1 | 12/2018 | Hoge |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0085368 A1 | 3/2019 | Bancel et al. |
| 2019/0099481 A1 | 4/2019 | Ciaramella et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314292 A1 | 10/2019 | Benenato et al. |
| 2019/0336452 A1 | 11/2019 | Brader |
| 2019/0351040 A1 | 11/2019 | Valiante et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129608 A1 | 4/2020 | Ciaramella et al. |
| 2020/0129615 A1 | 4/2020 | Ciaramella et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2021/0046173 A1 | 2/2021 | Ciaramella et al. |
| 2021/0163919 A1 | 6/2021 | Issa et al. |
| 2021/0187097 A1 | 6/2021 | Ciaramella et al. |
| 2021/0217484 A1 | 7/2021 | Giessel et al. |
| 2021/0228707 A1 | 7/2021 | Mektar et al. |
| 2021/0268086 A1 | 9/2021 | Zhong et al. |

FOREIGN PATENT DOCUMENTS

| | | |
|---|---|---|
| WO | WO 2005/118857 A2 | 12/2005 |
| WO | WO 2008/077592 A1 | 7/2008 |
| WO | WO 2011/071931 A2 | 6/2011 |
| WO | WO 2012/038450 A1 | 3/2012 |
| WO | WO 2013/102203 A1 | 7/2013 |
| WO | WO 2014/140211 A1 | 9/2014 |
| WO | WO 2014/152966 A1 | 9/2014 |
| WO | WO 2014/160243 A1 | 10/2014 |
| WO | WO 2015/188933 A1 | 12/2015 |
| WO | WO 2016/164762 A1 | 10/2016 |
| WO | WO 2016/201377 A1 | 12/2016 |
| WO | WO 2017/015457 A1 | 1/2017 |
| WO | WO 2017/015463 A1 | 1/2017 |
| WO | WO 2017/019935 A1 | 2/2017 |
| WO | WO 2017/020026 A1 | 2/2017 |
| WO | WO 2017/031232 A1 | 2/2017 |
| WO | WO 2017/031241 A1 | 2/2017 |
| WO | WO 2017/062513 A1 | 4/2017 |
| WO | WO 2017/066789 A1 | 4/2017 |
| WO | WO 2017/070601 A1 | 4/2017 |
| WO | WO 2017/070616 A1 | 4/2017 |
| WO | WO 2017/070618 A1 | 4/2017 |
| WO | WO 2017/070620 A1 | 4/2017 |
| WO | WO 2017/070622 A1 | 4/2017 |
| WO | WO 2017/070623 A1 | 4/2017 |
| WO | WO 2017/127750 A1 | 7/2017 |
| WO | WO 2017/201333 A1 | 11/2017 |
| WO | WO 2017/201340 A1 | 11/2017 |
| WO | WO 2017/201342 A1 | 11/2017 |
| WO | WO 2017/201347 A1 | 11/2017 |
| WO | WO 2018/053209 A1 | 3/2018 |
| WO | WO 2018/075980 A1 | 4/2018 |
| WO | WO 2018/081459 A1 | 5/2018 |
| WO | WO 2018/081462 A1 | 5/2018 |
| WO | WO 2018/089851 A1 | 5/2018 |
| WO | WO 2018/107088 A1 | 6/2018 |
| WO | WO 2018/111967 A1 | 6/2018 |
| WO | WO 2018/144082 A1 | 8/2018 |
| WO | WO 2018/144778 A1 | 8/2018 |
| WO | WO 2018/157009 A1 | 8/2018 |
| WO | WO 2018/170245 A1 | 9/2018 |
| WO | WO 2018/170256 A1 | 9/2018 |

(56) References Cited

FOREIGN PATENT DOCUMENTS

| | | |
|---|---|---|
| WO | WO 2018/170260 A1 | 9/2018 |
| WO | WO 2018/170270 A1 | 9/2018 |
| WO | WO 2018/170347 A1 | 9/2018 |
| WO | WO 2018/175783 A1 | 9/2018 |
| WO | WO 2018/187590 A2 | 10/2018 |
| WO | WO 2018/200737 A1 | 11/2018 |
| WO | WO 2018/232355 A1 | 12/2018 |
| WO | WO 2018/232357 A1 | 12/2018 |
| WO | WO 2019/036670 A1 | 2/2019 |
| WO | WO 2019/036682 A1 | 2/2019 |
| WO | WO 2019/036683 A1 | 2/2019 |
| WO | WO 2019/036685 A1 | 2/2019 |
| WO | WO 2019/103993 A1 | 5/2019 |
| WO | WO 2020/056370 A1 | 3/2020 |
| WO | WO 2020/061284 A1 | 3/2020 |
| WO | WO 2020/061295 A1 | 3/2020 |
| WO | WO 2020/061367 A1 | 3/2020 |
| WO | WO 2020/097291 A1 | 5/2020 |
| WO | WO 2020/172239 A1 | 8/2020 |
| WO | WO 2020/185811 A1 | 9/2020 |
| WO | WO 2020/190750 A1 | 9/2020 |
| WO | WO 2020/243561 A1 | 12/2020 |
| WO | WO 2021/030533 A1 | 2/2021 |
| WO | WO 2021/050864 A1 | 3/2021 |
| WO | WO 2021/055811 A1 | 3/2021 |
| WO | WO 2021/155243 A1 | 8/2021 |
| WO | WO 2021/159040 A2 | 8/2021 |
| WO | WO 2021/159130 A2 | 8/2021 |

OTHER PUBLICATIONS

U.S. Appl. No. 16/144,394, filed Sep. 27, 2018, Ciaramella et al.
U.S. Appl. No. 17/204,801, filed Mar. 17, 2021, Ciaramella et al.
U.S. Appl. No. 15/748,773, filed Jan. 30, 2018, Ciaramella et al.
U.S. Appl. No. 15/753,293, filed Feb. 17, 2018, Smith.
U.S. Appl. No. 15/767,587, filed Apr. 11, 2018, Ciaramella.
U.S. Appl. No. 16/833,409, filed Mar. 27, 2020, Ciaramella.
U.S. Appl. No. 15/767,600, filed Apr. 11, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 16/853,973, filed Apr. 21, 2020, Ciaramella et al.
U.S. Appl. No. 16/850,519, filed Apr. 16, 2020, Ciaramella et al.
U.S. Appl. No. 16/897,859, filed Jun. 10, 2020, Ciaramella et al.
U.S. Appl. No. 16/898,268, filed Jun. 10, 2020, Ciaramella et al.
U.S. Appl. No. 16/599,661, filed Oct. 11, 2019, Besin et al.
U.S. Appl. No. 16/864,566, filed May 1, 2020, Ciaramella et al.
U.S. Appl. No. 16/897,734, filed Jun. 10, 2020, Ciaramella et al.
U.S. Appl. No. 16/468,838, filed Jun. 12, 2019, Miracco.
U.S. Appl. No. 16/001,765, filed Jun. 6, 2018, Marquardt et al.
U.S. Appl. No. 17/127,949, filed Dec. 18, 2020, Ciaramella.
U.S. Appl. No. 17/385,655, filed Jul. 26, 2021, Ciaramella et al.
U.S. Appl. No. 16/603,111, filed Oct. 4, 2019, Brito et al.
U.S. Appl. No. 16/482,844, filed Aug. 1, 2019, Valiante et al.
U.S. Appl. No. 16/496,135, filed Sep. 20, 2019, Narayanan et al.
U.S. Appl. No. 16/483,012, filed Aug. 1, 2019, Mauger et al.
U.S. Appl. No. 17/350,662, filed Jun. 17, 2021, Rabideau et al.
U.S. Appl. No. 16/362,366, filed Mar. 22, 2019, Ciaramella.
U.S. Appl. No. 16/493,986, filed Sep. 13, 2019, Ciaramella et al.
U.S. Appl. No. 16/494,130, filed Sep. 13, 2019, Ciaramella et al.
U.S. Appl. No. 16/494,103, filed Sep. 13, 2019, Ciaramella et al.
U.S. Appl. No. 17/245,973, filed Apr. 30, 2021, Ciaramella.
U.S. Appl. No. 16/494,988, filed Sep. 17, 2019, Ciaramella et al.
U.S. Appl. No. 17/155,592, filed Jan. 22, 2021, Ciaramella et al.
U.S. Appl. No. 16/639,265, filed Feb. 14, 2020, Issa et al.
U.S. Appl. No. 16/639,305, filed Feb. 14, 2020, Issa et al.
U.S. Appl. No. 16/765,285, filed May 19, 2020, Ciaramella et al.
U.S. Appl. No. 16/302,607, filed Nov. 16, 2018, Benenato et al.
U.S. Appl. No. 16/623,069, filed Dec. 16, 2019, Hoge et al.
U.S. Appl. No. 16/639,403, filed Feb. 14, 2020, Hoge et al.
U.S. Appl. No. 16/848,318, filed Apr. 14, 2020, Ciaramella et al.
U.S. Appl. No. 16/965,589, filed Jul. 28, 2020, Ciaramella et al.
U.S. Appl. No. 17/255,949, filed Dec. 23, 2020, Zhong et al.
U.S. Appl. No. 17/277,423, filed Mar. 18, 2021, Almarsson et al.
U.S. Appl. No. 17/277,452, filed Mar. 18, 2021, Hennessy et al.
U.S. Appl. No. 17/276,112, filed Mar. 12, 2021, Martini et al.
U.S. Appl. No. 17/438,049, filed Sep. 10, 2021, Elich et al.
U.S. Appl. No. 17/291,947, filed May 6, 2021, Ashburn et al.
U.S. Appl. No. 17/439,198, filed Sep. 14, 2021, Lusso et al.
U.S. Appl. No. 17/325,883, filed May 20, 2021, Dousis et al.
U.S. Appl. No. 16/788,182, filed Feb. 11, 2020, Panther et al.
U.S. Appl. No. 16/794,318, filed Feb. 19, 2020, Mauger et al.
U.S. Appl. No. 17/145,164, filed Jan. 8, 2021, Giessel et al.
U.S. Appl. No. 17/411,896, filed Aug. 25, 2021, Kramarczyk et al.
U.S. Appl. No. 17/000,201, filed Aug. 21, 2020, Stewart-Jones et al.
U.S. Appl. No. 17/000,215, filed Aug. 21, 2020, Stewart-Jones et al.
International Search Report and Written Opinion for Application No. PCT/US2017/051674, dated Dec. 14, 2017.
[No Author Listed], MEGAscript Kit Product Manual, Oct. 27, 2009. Ambion/Invitrogen website: http://tools.invitrogen.com/contenl/sfs/manuals/ cms_072987.pdf, (last accessed Mar. 17, 2013). 29 pages.
Andrews-Pfannkoch, C. et al., Hydroxyapatite-mediated separation of double-stranded DNA, single-stranded DNA, and RNA genomes from natural viral assemblages. Appl Environ Microbiol. Aug. 2010;76(15):5039-45. Epub Jun. 11, 2010.
Brennan, Ribonucleoside triphosphate concentration-dependent termination of bacteriophage SP01 transcription in vitro by Bacillus subtilis RNA polymerase.Virology. Jun. 1984;135(2):555-60. doi: 10.1016/0042-6822(84)90211-3.
Devoldere et al., Evading innate immunity in nonviral mRNA delivery: don't shoot the messenger. Drug Discov Today. Jan. 2016;21(1):11-25. doi: 10.1016/j.drudis.2015.07.009. Epub Jul. 23, 2015.
Easton et al., Rapid, nondenaturing RNA purification using weak anion-exchange fast performance liquid chromatography. RNA. Mar. 2010;16(3):647-53. Epub Jan. 25, 2010.
Furuichi, Caps on Eukaryotic mRNAs. eLS. John Wiley & Sons. Jul. 1-12, 2014.
Georgopoulos et al., Use of high-performance liquid chromatographic fractionation of large RNA molecules in the assay of group I intron ribozyme activity. J Chromatogr A. Jan. 28, 2000;868(1):109-14.
Gruegelsiepe et al., Handbook of RNA Biochemistry, ed. R.K. Hartmann, Part LI, pp. 3-21, 2005.
Hartmann et al., Handbook of RNA Biochemistry, Second Edition, "Part I Rna Synthesis and Detection." 2014. p 1-27.
Jia et al., Kinetic mechanism of GTP binding and RNA synthesis during transcription initiation by bacteriophage T7 RNA polymerase. J Biol Chem. Nov. 28, 1997;272(48):30147-53. doi: 10.1074/jbc.272.48.30147.
Kariko et al., Generating the optimal mRNA for therapy: HPLC purification eliminates immune activation and improves translation of nucleoside-modified, protein-encoding mRNA. Nucleic Acids Res. Nov. 2011;39(21):e142.
Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.
Koch, G., et al., Quantitative Studies on the Infectivity of ribonucleic acid from partially purified and highly purified poliovirus preparations. Virology. Mar. 1960; 10(3): 329-343.
Lewandowski, L.J. et al., Separation of the infectious ribonucleic acid of potato spindle tuber virus from double-stranded ribonucleic acid of plant tissue extracts. J Virol. Nov. 1971;8(5):809-12.
Mellits, K.H. et al., Removal of double-stranded contaminants from RNA transcripts: synthesis of adenovirus VA RNAI from a T7 vector. Nucleic Acids Res. Sep. 25, 1990;18(18):5401-6.
Nedialkov et al., NTP-driven translocation by human RNA polymerase II. J Biol Chem. May 16, 2003;278(20):18303-12. doi: 10.1074/jbc.M301103200. Epub Mar. 13, 2003.

(56) References Cited

OTHER PUBLICATIONS

Sahin et al., mRNA-based therapeutics—developing a new class of drugs. Nat Rev Drug Discov. Oct. 2014;13(10):759-80. doi: 10.1038/nrd4278. Epub Sep. 19, 2014.
Steinle et al., Concise Review: Application of In Vitro Transcribed Messenger RNA for Cellular Engineering and Reprogramming: Progress and Challenges. Stem Cells. Jan. 2017;35(1):68-79. doi: 10.1002/stem.2402. Epub Jun. 20, 2016.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.
Wang et al., Purification of the messenger ribonucleic acid for the lipoprotein of the *Escherichia coli* outer membrane. Biochemistry. Oct. 2, 1979;18(20):4270-7.
Weissman et al., HPLC purification of in vitro transcribed long RNA. Methods Mol Biol. 2013;969:43-54. doi: 10.1007/978-1-62703-260-5_3.

Figure 4.
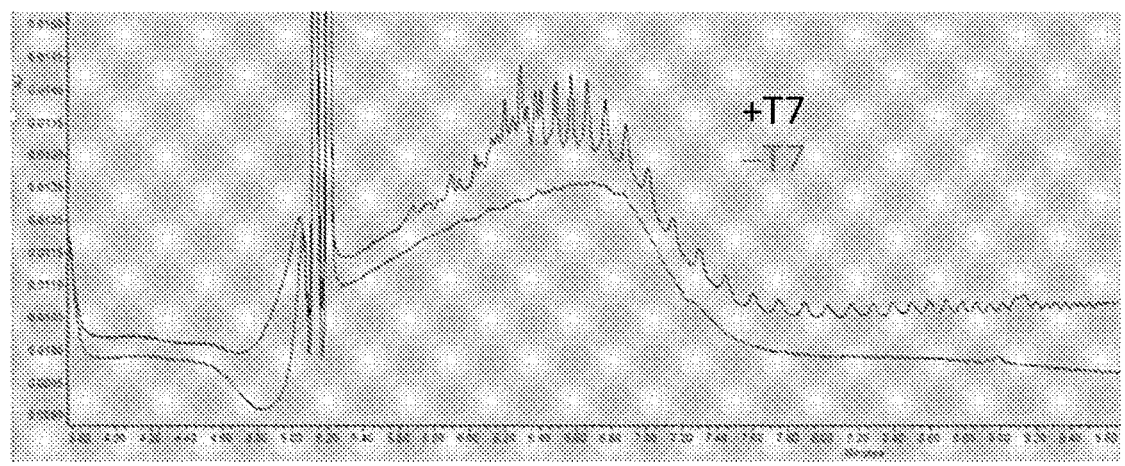
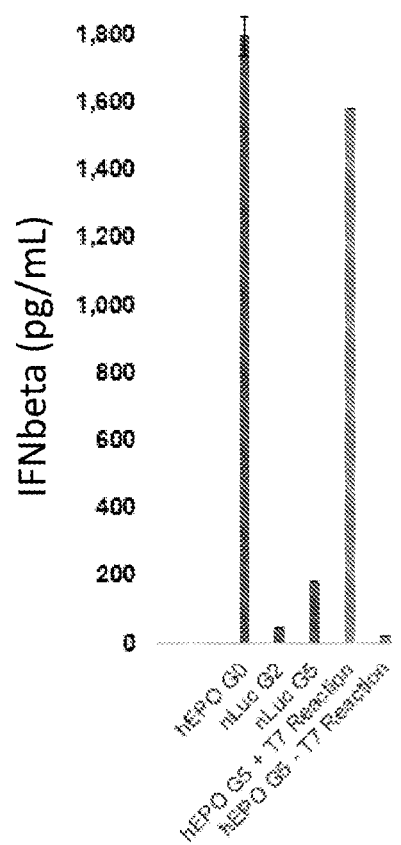

Figure 25.

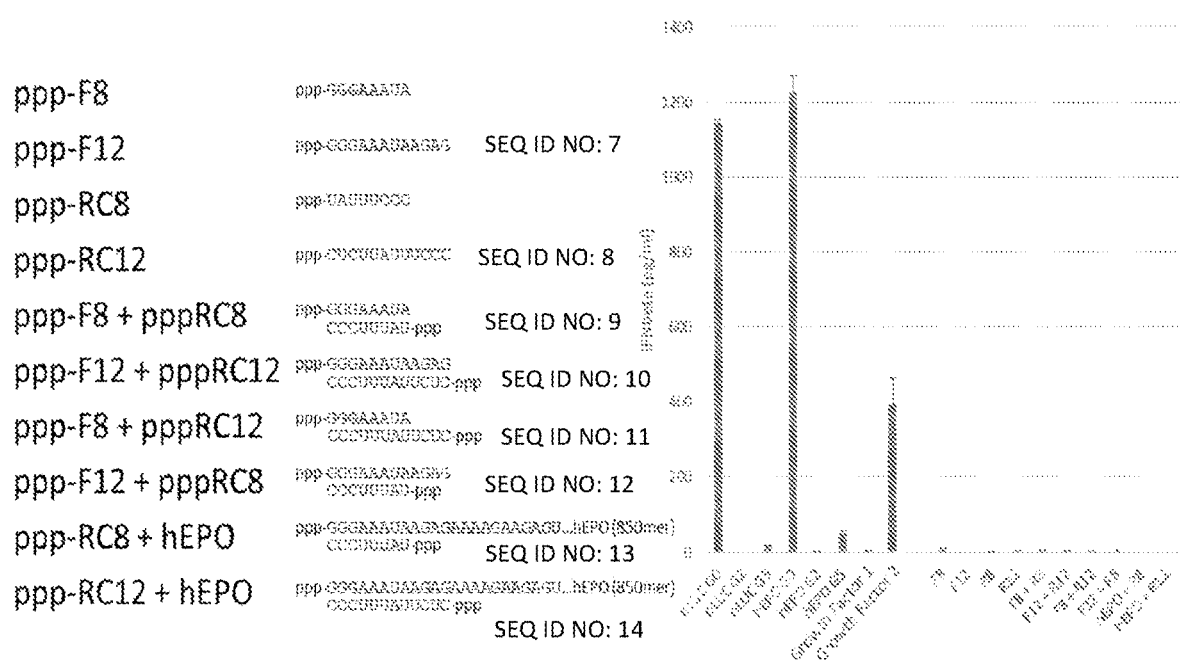

| | | |
|---|---|---|
| ppp-F8 | ppp-GGGAAAUA | |
| ppp-F12 | ppp-GGGAAAUAAGAG | SEQ ID NO: 7 |
| ppp-RC8 | ppp-UAUUUCCC | |
| ppp-RC12 | ppp-CUCUUAUUUCCC | SEQ ID NO: 8 |
| ppp-F8 + pppRC8 | ppp-GGGAAAUA / CCCUUUAU-ppp | SEQ ID NO: 9 |
| ppp-F12 + pppRC12 | ppp-GGGAAAUAAGAG / CCCUUUAUCUC-ppp | SEQ ID NO: 10 |
| ppp-F8 + pppRC12 | ppp-GGGAAAUA / CCCUUUAUCUC-ppp | SEQ ID NO: 11 |
| ppp-F12 + pppRC8 | ppp-GGGAAAUAAGAG / CCCUUUAU-ppp | SEQ ID NO: 12 |
| ppp-RC8 + hEPO | ppp-GGGAAAUAGAGAAAAGAAGAGU...hEPO(850mer) / CCCUUUAU-ppp | SEQ ID NO: 13 |
| ppp-RC12 + hEPO | ppp-GGGAAAUAGAGAAAAGAAGAGU...hEPO(850mer) / CCCUUUAUCUC-ppp | SEQ ID NO: 14 |

SEQUENCE LISTING

```
<160> NUMBER OF SEQ ID NOS: 32

<210> SEQ ID NO 1
<211> LENGTH: 12
<212> TYPE: RNA
<213> ORGANISM: Artificial Sequence
<220> FEATURE:
<223> OTHER INFORMATION: Synthetic Polynucleotide

<400> SEQUENCE: 1
cucuuauuuc cc                                                        12

<210> SEQ ID NO 2
<211> LENGTH: 49
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by OH
<220> FEATURE:
<221> NAME/KEY: misc_feature
<222> LOCATION: (49)..(49)
```

<223> OTHER INFORMATION: Modified by ppp

<400> SEQUENCE: 2
ggaaauaaga gagaaaagac ccuuuauucu cucuuuucuu cucauucuu                49

<210> SEQ ID NO 3
<211> LENGTH: 55
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by OH
<220> FEATURE:
<221> NAME/KEY: misc_feature
<222> LOCATION: (55)..(55)
<223> OTHER INFORMATION: Modified by ppp

<400> SEQUENCE: 3
gggaaauaag agagaaaaga agagucccuu uauucucucu uuucuucuca uucuu          55

<210> SEQ ID NO 4
<211> LENGTH: 60
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by OH
<220> FEATURE:
<221> NAME/KEY: misc_feature
<222> LOCATION: (60)..(60)
<223> OTHER INFORMATION: Modified by ppp

<400> SEQUENCE: 4
gggaaauaag agagaaaaga agaguaagaa cccuuuauuc ucucuuuucu ucucauucuu     60

<210> SEQ ID NO 5
<211> LENGTH: 65
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by OH
<220> FEATURE:
<221> NAME/KEY: misc_feature
<222> LOCATION: (65)..(65)
<223> OTHER INFORMATION: Modified by ppp

<400> SEQUENCE: 5
gggaaauaag agagaaaaga agaguaagaa gaaaucccuu uauucucucu uuucuucuca     60
uucuu                                                                65

<210> SEQ ID NO 6
<211> LENGTH: 70
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by OH

```
<220> FEATURE:
<221> NAME/KEY: misc_feature
<222> LOCATION: (70)..(70)
<223> OTHER INFORMATION: Modified by ppp

<400> SEQUENCE: 6 gggaauaag agagaaaaga agaguaagaa gaaauauaag cccuuuauuc ucucuuuucu    60
ucucauucuu                                                         70

<210> SEQ ID NO 7
<211> LENGTH: 12
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by ppp

<400> SEQUENCE: 7 gggaauaag ag                                                       12

<210> SEQ ID NO 8
<211> LENGTH: 12
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by ppp

<400> SEQUENCE: 8
cucuuauuuc cc                                                      12

<210> SEQ ID NO 9
<211> LENGTH: 16
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by ppp
<220> FEATURE:
<221> NAME/KEY: misc_feature
<222> LOCATION: (16)..(16)
<223> OTHER INFORMATION: Modified by ppp

<400> SEQUENCE: 9 gggaauacc cuuuau                                                   16

<210> SEQ ID NO 10
<211> LENGTH: 24
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by ppp
<220> FEATURE:
<221> NAME/KEY: misc_feature
<222> LOCATION: (24)..(24)
<223> OTHER INFORMATION: Modified by ppp
```

-continued

<400> SEQUENCE: 10
gggaaauaag agcccuuuau ucuc                                  24

<210> SEQ ID NO 11
<211> LENGTH: 20
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by ppp
<220> FEATURE:
<221> NAME/KEY: misc_feature
<222> LOCATION: (20)..(20)
<223> OTHER INFORMATION: Modified by ppp

<400> SEQUENCE: 11
gggaaauacc cuuuauucuc                                       20

<210> SEQ ID NO 12
<211> LENGTH: 20
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by ppp
<220> FEATURE:
<221> NAME/KEY: misc_feature
<222> LOCATION: (20)..(20)
<223> OTHER INFORMATION: Modified by ppp

<400> SEQUENCE: 12
gggaaauaag agcccuuuau                                       20

<210> SEQ ID NO 13
<211> LENGTH: 31
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by ppp
<220> FEATURE:
<221> NAME/KEY: misc_feature
<222> LOCATION: (31)..(31)
<223> OTHER INFORMATION: Modified by ppp

<400> SEQUENCE: 13
gggaaauaag agaaagaag agucccuuua u                           31

<210> SEQ ID NO 14
<211> LENGTH: 35
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by ppp
<220> FEATURE:
<221> NAME/KEY: misc_feature
<222> LOCATION: (35)..(35)
<223> OTHER INFORMATION: Modified by ppp

```
<400> SEQUENCE: 14
gggaaauaag agaaagaag agucccuuua uucuc                                35

<210> SEQ ID NO 15
<211> LENGTH: 40
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by ppp
<220> FEATURE:
<221> NAME/KEY: misc_feature
<222> LOCATION: (40)..(40)
<223> OTHER INFORMATION: Modified by ppp

<400> SEQUENCE: 15
gggaaauaag agagaaaaga cccuuuauuc ucucuuuucu                          40

<210> SEQ ID NO 16
<211> LENGTH: 41
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by OH
<220> FEATURE:
<221> NAME/KEY: misc_feature
<222> LOCATION: (41)..(41)
<223> OTHER INFORMATION: Modified by ppp

<400> SEQUENCE: 16
aaaaaaaaaa aaaaaaaaaa aaaaauuuuu uuuuuuuuuu u                        41

<210> SEQ ID NO 17
<211> LENGTH: 45
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by OH
<220> FEATURE:
<221> NAME/KEY: misc_feature
<222> LOCATION: (45)..(45)
<223> OTHER INFORMATION: Modified by ppp

<400> SEQUENCE: 17
aaaaaaaaaa aaaaaaaaaa aaaaauuuuu uuuuuuuuuu uuuuu                    45

<210> SEQ ID NO 18
<211> LENGTH: 49
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by OH
<220> FEATURE:
<221> NAME/KEY: misc_feature
<222> LOCATION: (49)..(49)
```

<223> OTHER INFORMATION: Modified by ppp

<400> SEQUENCE: 18
aaaaaaaaaa aaaaaaaaaa aaaaauuuuu uuuuuuuuuu uuuuuuuu                    49

<210> SEQ ID NO 19
<211> LENGTH: 43
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by ppp
<220> FEATURE:
<221> NAME/KEY: misc_feature
<222> LOCATION: (43)..(43)
<223> OTHER INFORMATION: Modified by ppp

<400> SEQUENCE: 19
gggaaauaag agaaaagaag agucccuuua uucucucuuu ucu                         43

<210> SEQ ID NO 20
<211> LENGTH: 40
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by ppp
<220> FEATURE:
<221> NAME/KEY: misc_feature
<222> LOCATION: (40)..(40)
<223> OTHER INFORMATION: Modified by ppp

<400> SEQUENCE: 20
gggaaauaag agagaaaaga cccuuuauuc ucucuuuucu                             40

<210> SEQ ID NO 21
<211> LENGTH: 40
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by ppp
<220> FEATURE:
<221> NAME/KEY: misc_feature
<222> LOCATION: (40)..(40)
<223> OTHER INFORMATION: Modified by OH

<400> SEQUENCE: 21
gggaaauaag agagaaaaga cccuuuauuc ucucuuuucu                             40

<210> SEQ ID NO 22
<211> LENGTH: 40
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by OH
<220> FEATURE:
<221> NAME/KEY: misc_feature

```
<222> LOCATION: (40)..(40)
<223> OTHER INFORMATION: Modified by ppp

<400> SEQUENCE: 22
gggaaauaag agagaaaaga cccuuuauuc ucucuuuucu                           40

<210> SEQ ID NO 23
<211> LENGTH: 45
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by OH
<220> FEATURE:
<221> NAME/KEY: misc_feature
<222> LOCATION: (45)..(45)
<223> OTHER INFORMATION: Modified by ppp

<400> SEQUENCE: 23
gggaaauaag agagaaaaga agagucccuu uauucucucu uuucu                     45

<210> SEQ ID NO 24
<211> LENGTH: 50
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by OH
<220> FEATURE:
<221> NAME/KEY: misc_feature
<222> LOCATION: (50)..(50)
<223> OTHER INFORMATION: Modified by ppp

<400> SEQUENCE: 24
gggaaauaag agagaaaaga agaguaagaa cccuuuauuc ucucuuuucu                50

<210> SEQ ID NO 25
<211> LENGTH: 55
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by OH
<220> FEATURE:
<221> NAME/KEY: misc_feature
<222> LOCATION: (55)..(55)
<223> OTHER INFORMATION: Modified by ppp

<400> SEQUENCE: 25
gggaaauaag agagaaaaga agaguaagaa gaaaucccuu uauucucucu uuucu          55

<210> SEQ ID NO 26
<211> LENGTH: 60
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by OH
<220> FEATURE:
```

```
<221> NAME/KEY: misc_feature
<222> LOCATION: (60)..(60)
<223> OTHER INFORMATION: Modified by ppp

<400> SEQUENCE: 26
gggaaauaag agagaaaaga agaguaagaa gaaauauaag cccuuuauuc ucucuuuucu      60

<210> SEQ ID NO 27
<211> LENGTH: 67
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by OH
<220> FEATURE:
<221> NAME/KEY: misc_feature
<222> LOCATION: (67)..(67)
<223> OTHER INFORMATION: Modified by ppp

<400> SEQUENCE: 27
gggaaauaag agagaaaaga agaguaagaa gaaauauaag agccaccccc uuuauucucu      60
cuuuucu                                                               67

<210> SEQ ID NO 28
<211> LENGTH: 26
<212> TYPE: RNA
<213> ORGANISM: Artificial Sequence
<220> FEATURE:
<223> OTHER INFORMATION: Synthetic Polynucleotide

<400> SEQUENCE: 28
gacucuucuu uucucucuua uuuccc                                          26

<210> SEQ ID NO 29
<211> LENGTH: 31
<212> TYPE: RNA
<213> ORGANISM: Artificial Sequence
<220> FEATURE:
<223> OTHER INFORMATION: Synthetic Polynucleotide

<400> SEQUENCE: 29
guucuuacuc uucuuuucuc ucuuauuucc c                                    31

<210> SEQ ID NO 30
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 30
gauuucuucu uacucuucuu uucucucuua uuuccc                               36

<210> SEQ ID NO 31
<211> LENGTH: 60
<212> TYPE: RNA
<213> ORGANISM: Artificial Sequence
<220> FEATURE:
<223> OTHER INFORMATION: Synthetic Polynucleotide

<400> SEQUENCE: 31
gggaaauaag agagaaaaga agaguaagaa gaaauauaag agccaccaug ggagugcacg      60
```

```
<210> SEQ ID NO 32
<211> LENGTH: 60
<212> TYPE: RNA
<213> ORGANISM: Artificial Sequence
<220> FEATURE:
<223> OTHER INFORMATION: Synthetic Polynucleotide

<400> SEQUENCE: 32
cgugcacucc caugguggcu cuuauauuuc uucuuacucu ucuuuucucu cuuauuuccc        60
```

HIGH PURITY RNA COMPOSITIONS AND METHODS FOR PREPARATION THEREOF

RELATED APPLICATIONS

This application is a national stage filing under 35 U.S.C. § 371 of international application number PCT/US2017/051674, filed Sep. 14, 2017, which was published under PCT Article 21(2) in English and claims the benefit under 35 U.S.C. § 119(e) of U.S. provisional application Ser. No. 62/394,711, filed Sep. 14, 2016, each of which is incorporated by reference herein in its entirety.

BACKGROUND OF INVENTION

The ability to design, synthesize and deliver a nucleic acid, e.g., a ribonucleic acid (RNA) for example, a messenger RNA (mRNA) inside a cell, has provided advancements in the fields of therapeutics, diagnostics, reagents and for biological assays. Many advancements are being made in the process of intracellular translation of the nucleic acid and production of at least one encoded peptide or polypeptide of interest.

mRNA has immense therapeutic potential in that mRNA therapeutics can transiently express essentially any desired protein while avoiding the adverse effects of viral and DNA-based nucleic acid delivery approaches. Mammalian cells, in particular, human cells, however, contain sensors of nucleic acids including RNA as part of the innate immune system—and it is desirable to avoid such sensing and immune response when developing mRNA therapeutics.

In theory, mRNAs produced via chemical synthesis hold promise as mRNA therapeutics, however, the majority of the research in this important therapeutic area to date has focused on in vitro-transcribed (IVT) mRNA, as this enzymatic process facilitates the production of long RNAs, on the order of 1-2 or more kB, the standard length of most mRNA molecules.

Early work showed that incorporation of modified nucleosides, in particular, pseudouridine, reduced innate immune activation and increased translation of mRNA, but residual induction of type I interferons (IFNs) and proinflammatory cytokines remained (Kariko et al. (2005) Immunity 23(2):165-75). Progress was made towards the identification of the contaminants in nucleoside-modified IVT RNA identifying double-stranded RNA (dsRNA) as being at lease partially responsible for innate immune activation. Removal of such contaminants by high performance liquid chromatography (HPLC) resulted in reduced IFN and inflammatory cytokine levels and in turn, higher expression levels in primary cells (Kariko et al. (2011) Nuc. Acids Res. 39:e142). Notably, unmodified mRNAs still induced high levels of cytokine secretion although they were better-translated following HPLC purification.

WO 2013/102203 describes an RNAse III treatment method used to remove dsRNA from IVT mRNA for repeated or continuous transfection into human or animal cells, in particular, for reprogramming of cells from one differentiation state to another. The method purports to result in preparations having decreased levels of dsRNA and increased levels of intact ssRNA, as evidenced by higher levels of reprogramming factors and less toxicity to cells. Such methods, however, are not compatible for use in the preparation of mRNAs for therapeutic use, in particular, for human therapeutic use. RNAse III is known to digest ssRNA as well as dsRNA and in trying to remove dsRNA contaminants, the integrity of the desired ssRNA product is necessarily jeopardized. Thus, there exists a need for better understanding of the nature of contaminants in IVT-generated mRNA preparations, in order to better control for levels and nature of contaminants in IVT preparations. There further exists a need for improved methods of preparing mRNA for therapeutic use and for high purity compositions produced according to such methods.

SUMMARY OF INVENTION

The invention involves, at least in part, the discovery of novel methods for in vitro RNA synthesis and related products. The RNA transcripts produced by the methods described herein have enhanced properties which result in qualitatively and quantitatively superior compositions comprising said RNA transcripts. The RNA transcripts produced by the methods described herein have enhanced properties particularly important for mRNA, lncRNA, and other therapeutic and diagnostic RNA uses, such as improved immune silencing and better safety profiles.

In particular, IVT RNA compositions of the invention are substantially free of certain undesirable contaminants routinely associated with the IVT process. Notably, however, the methods of the invention arrive at mRNA compositions suitable for therapeutic use by controlling the nature and levels of contaminants produced in the IVT reaction, i.e., the contaminants are not made in the initial reaction, as contrasted to art-described methods which attempt to remove contaminants once they have been produced. Without being bound in theory, it is believed that preventing the production of unwanted contaminants in the IVT reaction from the outset provides for improved compositions having higher purity and potency, measurable, for example, in terms of increased translation from full-length, intact mRNA in the composition.

A composition comprising an in vitro-transcribed (IVT) RNA and a pharmaceutically acceptable excipient, wherein the composition is substantially free of reverse complement transcription product is provided in some aspects of the invention. In some embodiments, less than about 5%, 4.5%, 4%, 3.5%, 3%, 2.5%, 2%, 1.5%, 1%, 0.9%, 0.8%, 0.7%, 0.6%, or 0.55% of the total mass of the RNA in the composition is reverse complement transcription product. In some embodiments, less than about 1.0% of the mass of the RNA in the composition is reverse complement transcription product. In some embodiments, less than about 0.5% of the mass of the RNA in the composition is reverse complement transcription product. In some embodiments, less than about 0.25% of the mass of the RNA in the composition is reverse complement transcription product. In some embodiments, less than about 0.1% of the mass of the RNA in the composition is reverse complement transcription product. In some embodiments, less than about 0.05% of the mass of the RNA in the composition is reverse complement transcription product. In some embodiments, less than about 0.01% of the mass of the RNA in the composition is reverse complement transcription product. In some embodiments, less than about 0.005% of the mass of the RNA in the composition is reverse complement transcription product. In some embodiments, less than about 0.001% of the mass of the RNA in the composition is reverse complement transcription product. In exemplary embodiments, the mass of the RNA in the composition is determined by LC, J2 Elisa, RNase III, Gel electrophoresis with radiolabeled NTPs, LCMS +/− nuclease or chemical digestion, NMR using labelled NTPs, chemically/isotopically/radioactively etc. labelled NTPs, cells, biochemical means, RIG-I ATPase activity or MS or gel electrophoresis or other methods known in the art to be suitable for detection and/or quantitation of RNA in RNA-containing compositions.

In some embodiments the reverse complement transcription product is fully complementary with a region of the RNA which is the desired or intended IVT transcription produce (e.g., an mRNA, lncRNA, or other RNA greater than 50 nucleotides in length intended for therapeutic use). A product that is fully complementary with the RNA transcript is considered to have 100% complementarity (e.g., over the length of the reverse complement transcription product. In other embodiments the reverse complement transcription product is partially complementary with a region of the RNA transcript. In some embodiments the reverse complement transcription product is 70%, 75%, 80%, 85%, 90%, 91%, 92%, 93%, 94%, 95%, 96%, 97%, 98%, or 99% complementary with a region of the RNA transcript. In yet other embodiments the reverse complement product is 70%-90%, 75%-90%, 80%-90%, 85%-90%, 90%-95%, 91%-95%, 92%-95%, 93%-95%, 94%-95%, 95%-99%, 96%-99%, 97%-99%, or 98%-99% complementary with a region of the RNA transcript.

The skilled artisan will appreciate that unintended or undesirable reverse complement transcription products generated in an IVT reaction can have complementarity not only to the RNA transcript which is the intended or desired product of the IVT reaction (e.g., an mRNA, lncRNA, or other RNA greater than 50 nucleotides in length intended for therapeutic use) but also can have complementarity to a strand of the DNA template from which the intended or desired RNA transcript is produced. Without being bound in theory, it is believed that certain unintended or undesirable transcription products contaminating IVT RNA compositions that are reduced or eliminated according to the novel processes of the instant invention are transcribed from the intended or desired RNA transcription product, there exists the possibility that certain unintended or undesirable transcription products contaminating IVT RNA compositions may be transcribed from the DNA template used in the IVT reactions. The latter supposition, while possible, does not appear to be evidenced by the data presented herein which demonstrates reverse complement transcription products predominantly complementary to the 5' UTR and/or polyA tail of mRNA transcripts, whereas reverse complement transcription products complementary to portions (e.g., sequence elements) of a DNA template not present in transcribed mRNA are significantly decreased and in some instances not detectable.

In other aspects the invention is a composition comprising an in vitro-transcribed (IVT) RNA encoding a polypeptide of interest and a pharmaceutically acceptable excipient, wherein the composition is substantially free of cytokine-inducing RNA contaminant. In some embodiments, less than about 0.5% of the mass of the RNA in the composition is cytokine-inducing RNA contaminant. In some embodiments, less than about 0.25% of the mass of the RNA in the composition is cytokine-inducing RNA contaminant. In some embodiments, less than about 0.1% of the mass of the RNA in the composition is cytokine-inducing RNA contaminant. In some embodiments, less than about 0.05% of the mass of the RNA in the composition is cytokine-inducing RNA contaminant. In some embodiments, less than about 0.01% of the mass of the RNA in the composition is cytokine-inducing RNA contaminant. In some embodiments, less than about 0.005% of the mass of the RNA in the composition is cytokine-inducing RNA contaminant. In some embodiments, less than about 0.001% of the mass of the RNA in the composition is cytokine-inducing RNA contaminant. In some embodiments, the mass of the RNA in the composition is determined by LC or MS or gel electrophoresis or other method known in the art.

In some embodiments the invention features a composition comprising an in vitro-transcribed (IVT) RNA encoding a polypeptide of interest and a pharmaceutically acceptable excipient, wherein the composition has reduced levels of cytokine-inducing RNA contaminant and/or reverse complement transcription product.

In some embodiments of the compositions of the invention described herein, the mass of the sum total of cytokine-inducing RNA contaminant and/or the reverse complement transcription product is less than about 10%, 9%, 8%, 7%, 6%, 5%, 4.5%, 4%, 3.5%, 3%, 2.5%, 2%, 1.5%, 1%, 0.9%, 0.8%, 0.7%, 0.6%, or 0.55%, 0.5%, 0.45%, 0.4%, 0.35%, 0.3%, 0.0.25%, 0.2%, 0.15%, 0.1%, 0.05%, 0.01%, 0.005%, or 0.001% of the total mass of the RNA in the composition. In some embodiments the ratio of the cytokine-inducing RNA contaminant to RNA transcription product (e.g., intended or desired RNA transcript) in the composition is 99:1, 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, 5:95, or 1:99. In other embodiments the ratio of the reverse complement transcription product to the RNA transcription product (e.g., intended or desired RNA transcript) in the composition is 99:1, 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, 5:95, or 1:99.

The size of the contaminant may vary. In some embodiments the length of the cytokine-inducing RNA contaminant and/or RNA transcription product is greater than 2 nucleotides up to and including the length of the full length transcription product (e.g., the intended or desired transcription produce, for example the mRNA transcript). In other embodiments the length of the cytokine-inducing RNA contaminant and/or RNA transcription product is greater than 5, 10, 15, 20, 25, 30, 35, 40, 45 or 50 nucleotides each up to and including the length of the full length transcription product. In other embodiments the length of the cytokine-inducing RNA contaminant and/or RNA transcription product is 2-500 nucleotides in length, 10-500 nucleotides in length, 15-500 nucleotides in length, 20-500 nucleotides in length, 30-500 nucleotides in length, 40-500 nucleotides in length, 50-500 nucleotides in length, 100-500 nucleotides in length, 200-500 nucleotides in length, 300-500 nucleotides in length, 400-500 nucleotides in length, 2-200 nucleotides in length, 10-200 nucleotides in length, 15-200 nucleotides in length, 20-200 nucleotides in length, 30-200 nucleotides in length, 40-200 nucleotides in length, 50-200 nucleotides in length, 100-200 nucleotides in length, 200-300 nucleotides in length, 300-400 nucleotides in length, 2-100 nucleotides in length, 10-100 nucleotides in length, 15-100 nucleotides in length, 20-100 nucleotides in length, 30-100 nucleotides in length, 40-100 nucleotides in length, or 50-100 nucleotides in length.

The skilled artisan will appreciate that RNA contaminants of a certain structure and/or length are quite prone to stimulating undesired or unwanted immune responses, for example, RNA contaminants of at least 15 or at least 20 or at least 25 nucleotides in length, in particular, RNA contaminants that are double-stranded in nature (dsRNAs). Removal of such contaminants is possible using certain art-recognized methodologies (e.g., enzymatic and/or purification processes or method steps). However, each of such additional purification process or step in the generation of, for example, mRNAs, lncRNA, or other RNA greater than 50 nucleotides in length intended for therapeutic use, introduces the possibility of reduced fidelity of the intended product, for example, by subjecting the direct IVT reaction product to (1) enzymatic conditions (e.g., RNAse treatment producing fragments of RNA) and/or (2) high temperature, non-physiologic solvent conditions (e.g., HPLC or RP chromatography conditions) which can compromise the quality of the RNA product in the process of attempting to degrade or remove contaminants.

In certain aspects of the invention, undesired or unwanted contaminants are a population of RNA species having a distribution of, for example, sizes and masses within a certain range. For example, a certain type of contaminant can have less than 5% of any individual species of contaminant (i.e., RNA species of the same sequence, same length, etc.). In other embodiments contaminants can have less than 4.5%, 4.0%, 3.5%, 3.0%, 2.5%, 2.0%, 1.5%, 1.0%, 0.5%, 0.4%, 0.3%, 0.2%, 0.1%, 0.05%, 0.001%, 0.0005%, or 0.0001% of any individual species.

In some embodiments the reverse complement transcription product is a RNA (dsRNA, ssRNA or a ds-ssRNA hybrid having a ds portion and a ss portion) comprising a strand comprising a sequence which is a reverse complement of the IVT RNA or a RNA (dsRNA, ssRNA or a ds-ssRNA. In some embodiments, where the Poly A tail is encoded within a PolyA:T tract within the DNA template, the reverse complement product comprises a strand comprising a polyU sequence or others ways commonly used in the art to install polyA tails in RNA. The poly U sequence is, for example, pppU(U)n wherein n is 1 or greater. In some embodiments n is 1-100 (for encoded poly A tails where target RNA has 100 nt poly A tail. In other embodiments n is greater than 30 or 30-200. In exemplary embodiments the reverse complement product initiates with a 5' triphosphate (5'-PPP). In other embodiments the reverse complement product initiates with a 5' diphosphate (5'-PP) or a 5' monophosphate (5'-P).

In some embodiments the reverse complement transcription product comprises a reverse complement of the 5'-end of the IVT RNA and/or a reverse complement of the 3'-end of the IVT RNA. In some embodiments the reverse complement of the 5'-end of the IVT RNA comprises a sequence complementary to all or a portion of a 5' UTR of the IVT RNA. In other embodiments the reverse complement of the 3'-end of the IVT RNA comprises a sequence complementary to all or a portion of a polyA tail of the IVT RNA. In yet other embodiments the reverse complement of the 3'-end is the reverse complement of a tailless RNA. In yet other embodiments the reverse complement transcription product comprises a sequence complementary to all or a portion of a 5' end, a 3' end, an open reading frame and/or a polyA tail of the RNA or any combination thereof.

In exemplary aspects of the invention, a cytokine-inducing RNA-contaminant is a RNA (dsRNA, ssRNA or a ds-ssRNA. In some embodiments the cytokine-inducing RNA-contaminant is a strand that in some embodiments comprises a reverse sequence which is a reverse complement of the IVT RNA or a dsRNA or ssRNA comprising a strand comprising a polyU sequence.

In some embodiments the strand comprising the sequence which is the reverse complement of the IVT RNA or the strand comprising the polyU sequence initiates with a 5' triphosphate (5'-PPP). In some embodiments the polyU sequence is greater than 20 nucleotides in length. In some embodiments the polyU sequence is greater than 30 nucleotides in length. In other embodiments the polyU sequence is single stranded. In yet other embodiments the polyU sequence is double stranded.

In some embodiments the cytokine-inducing RNA-contaminant comprises a reverse complement of the 5'-end of the IVT RNA and/or a reverse complement of the 3'-end of the IVT RNA. In some embodiments the reverse complement of the 5'-end of the IVT RNA comprises a sequence complementary to all or a portion of a 5' UTR of the IVT RNA. In other embodiments the reverse complement of the 3'-end of the IVT RNA comprises a sequence complementary to all or a portion of a polyA tail of the IVT RNA. In some embodiments the reverse complement comprises a sequence complementary the first 10-15 nucleotides of the 5' UTR. In some embodiments the reverse complement comprises a sequence complementary the first 10-20 nucleotides of the 5' UTR. In some embodiments the reverse complement comprises a sequence complementary the first 10-30 nucleotides of the 5' UTR. In some embodiments the reverse complement comprises a sequence complementary the first 10-40 nucleotides of the 5' UTR. In yet other embodiments the cytokine-inducing RNA-contaminant comprises a sequence complementary to all or a portion of a 5' end, a 3' end, an open reading frame and/or a polyA tail of the RNA or any combination thereof.

In some embodiments the cytokine-inducing RNA-contaminant is a single stranded tri-phosphate reverse complement of 20 nucleotides or greater. In other embodiments the cytokine-inducing RNA-contaminant is a single stranded tri-phosphate reverse complement of 25 nucleotides or greater. In other embodiments the cytokine-inducing RNA-contaminant is a single stranded tri-phosphate reverse complement of 30 nucleotides or greater. In some embodiments the single stranded tri-phosphate reverse complement is 20-200 nucleotides in length. In some embodiments the single stranded tri-phosphate reverse complement is 20-100 nucleotides in length. In some embodiments the single stranded tri-phosphate reverse complement is 20-50 nucleotides in length. In some embodiments the single stranded tri-phosphate reverse complement is 25-200 nucleotides in length. In some embodiments the single stranded tri-phosphate reverse complement is 25-100 nucleotides in length. In some embodiments the single stranded tri-phosphate reverse complement is 25-50 nucleotides in length. In some embodiments the single stranded tri-phosphate reverse complement is 30-200 nucleotides in length. In some embodiments the single stranded tri-phosphate reverse complement is 30-100 nucleotides in length. In some embodiments the single stranded tri-phosphate reverse complement is 30-50 nucleotides in length.

In other embodiments the cytokine-inducing RNA-contaminant is a single stranded reverse complement having a terminal tri-phosphate-A, tri-phosphate-C, or tri-phosphate-U.

In other embodiments the cytokine-inducing RNA-contaminant is a double stranded tri-phosphate reverse complement of 20 nucleotides or greater. In some embodiments the double stranded tri-phosphate reverse complement has 20-200 nucleotides. In yet other embodiments the cytokine-inducing RNA-contaminant is a double stranded tri-phosphate reverse complement that is a perfect duplex (no single stranded regions). In other embodiments the cytokine-inducing RNA-contaminant is a double stranded tri-phosphate reverse complement that includes a single stranded overhang.

In some aspects of the invention, a dsRNA comprises strands of between 20 and 100 nucleotides in length in some embodiments. In other embodiments the dsRNA is of duplex of between about 20 and about 50 bp in length. In yet other embodiments the dsRNA comprises strands of 1-1,000, 5-1,000, 10-1,000, 100-1,000, 500-1,000, 1-10, 1-20, 1-50, 1-100, 5-10, 5-20, 5-30, 5-50, 5-100, 5-200, 5-300, 5-400, 10-20, 10-30, 10-100, 10-200, 10-300, 10-400, 10-500, 20-25, 20-30, 20-100, 20-200, 20-300, 20-400, 20-500, 30-35, 30-40, 30-100, 30-200, 30-300, 30-400, or 30-500 nucleotides in length. In yet other embodiments the dsRNA comprises strands of 1 nucleotide to full length transcript length.

In other embodiments less than about 0.5% of the mass of the RNA in the composition is dsRNA of a size greater than 40 base pairs.

The purity of the products may be assessed using known analytical methods and assays. In exemplary aspects of the invention the amount of reverse complement transcription product or cytokine-inducing RNA contaminant is determined by high-performance liquid chromatography (such as reverse-phase chromatography, size-exclusion chromatography), Bioanalyzer chip-based electrophoresis system, ELISA, flow cytometry, acrylamide gel, a reconstitution or surrogate type assay. The assays may be performed with or without nuclease treatment (P1, RNase III, RNase H etc.) of the RNA preparation. Electrophoretic/chromatographic/mass spec analysis of nuclease digestion products may also be performed.

In some embodiments the mass of RNA is determined by mass spectrometry such as LC-MS, MALDI-TOF (matrix-assisted laser desorption ionization time of flight).

In some embodiments the composition comprises contaminant transcripts that have a length less than a full length transcript, such as for instance at least 100, 200, 300, 400, 500, 600, 700, 800, or 900 nucleotides less than the full length. Contaminant transcripts can include reverse or forward transcription products (transcripts) that have a length less than a full length transcript, such as for instance at least 100, 200, 300, 400, 500, 600, 700, 800, or 900 nucleotides less than the full length. Exemplary forward transcripts include, for instance, abortive transcripts. In certain embodiments the composition comprises a tri-phosphate poly-U reverse complement of less than 30 nucleotides. In some embodiments the composition comprises a tri-phosphate poly-U reverse complement of any length hybridized to a full length transcript. In other embodiments the composition comprises a single stranded tri-phosphate forward transcript. In other embodiments the composition comprises a single stranded RNA having a terminal tri-phosphate-G. In other embodiments the composition comprises single or double stranded RNA of less than 12 nucleotides or base pairs (including forward or reverse complement transcripts). In any of these embodiments the composition may include less than 50%, 45%, 40%, 35%, 30%, 25%, 20%, 15%, 10%, 9%, 8%, 7%, 6%, 5%, 4%, 3%, 2%, 1%, or 0.5% of any one of or combination of these less than full length transcripts.

In other embodiments the RNA is produced by a process or is preparable by a process comprising (a) forming a reaction mixture comprising a DNA template and NTPs including adenosine triphosphate (ATP), cytidine triphosphate (CTP), uridine triphosphate (UTP), guanosine triphosphate (GTP) and optionally guanosine diphosphate (GDP), and (eg. buffer containing T7 co-factor eg. magnesium).

(b) incubating the reaction mixture under conditions such that the RNA is transcribed, wherein the concentration of at least one of GTP, CTP, ATP, and UTP is at least 2× greater than the concentration of any one or more of ATP, CTP or UTP or the reaction further comprises a nucleotide diphosphate (NDP) or a nucleotide analog and wherein the concentration of the NDP or nucleotide analog is at least 2× greater than the concentration of any one or more of ATP, CTP or UTP, In some embodiments the ratio of concentration of GTP to the concentration of any one ATP, CTP or UTP is at least 2:1, at least 3:1, at least 4:1, at least 5:1 or at least 6:1.

The ratio of concentration of GTP to concentration of ATP, CTP and UTP is, in some embodiments 2:1, 4:1 and 4:1, respectively. In other embodiments the ratio of concentration of GTP to concentration of ATP, CTP and UTP is 3:1, 6:1 and 6:1, respectively. The reaction mixture may comprise GTP and GDP and wherein the ratio of concentration of GTP plus GDP to the concentration of any one of ATP, CTP or UTP is at least 2:1, at least 3:1, at least 4:1, at least 5:1 or at least 6:1 In some embodiments the ratio of concentration of GTP plus GDP to concentration of ATP, CTP and UTP is 3:1, 6:1 and 6:1, respectively.

In yet other embodiments the RNA is produced by a process or is preparable by a process comprising (a) forming a reaction mixture comprising a DNA template and adenosine triphosphate (ATP), cytidine triphosphate (CTP), uridine triphosphate (UTP), guanosine triphosphate (GTP) and optionally guanosine diphosphate (GDP), and a buffer magnesium-containing buffer, (b) incubating the reaction mixture under conditions such that the RNA is transcribed, wherein the effective concentration of phosphate in the reaction is at least 150 mM phosphate, at least 160 mM, at least 170 mM, at least 180 mM, at least 190 mM, at least 200 mM, at least 210 mM or at least 220 mM. The effective concentration of phosphate in the reaction may be 180 mM. The effective concentration of phosphate in the reaction in some embodiments is 195 mM. In other embodiments the effective concentration of phosphate in the reaction is 225 mM.

In other embodiments the RNA is produced by a process or is preparable by a process comprising (a) forming a reaction mixture comprising a DNA template and adenosine triphosphate (ATP), cytidine triphosphate (CTP), uridine triphosphate (UTP), guanosine triphosphate (GTP) and optionally guanosine diphosphate (GDP), and a buffer magnesium-containing buffer, (b) incubating the reaction mixture under conditions such that the RNA is transcribed, wherein the magnesium-containing buffer comprises Mg2+ and wherein the molar ratio of concentration of ATP plus CTP plus UTP pus GTP and optionally GDP to concentration of Mg2+ is at least 1.0, at least 1.25, at least 1.5, at least 1.75, at least 1.85, at least 3 or higher. The molar ratio of concentration of ATP plus CTP plus UTP pus GTP and optionally GDP to concentration of Mg2+ may be 1.5. The molar ratio of concentration of ATP plus CTP plus UTP pus GTP and optionally GDP to concentration of Mg2+ in some embodiments is 1.88. The molar ratio of concentration of ATP plus CTP plus UTP pus GTP and optionally GDP to concentration of Mg2+ in some embodiments is 3.

In some embodiments the composition is produced by a process which does not comprise an dsRNase (e.g., RNaseIII) treatment step. In other embodiments the composition is produced by a process which does not comprise a reverse phase (RP) chromatography purification step. In yet other embodiments the composition is produced by a process which does not comprise a high-performance liquid chromatography (HPLC) purification step.

The RNA in some embodiments is modified mRNA. In other embodiments the RNA is unmodified RNA. In other embodiments the RNA is lncRNA. In yet other embodiments is RNA greater than 50 nucleotides in length. The RNA may include a UTP and the UTP is modified UTP.

In some embodiments the amount of reverse complement transcription product or cytokine-inducing species is determined indirectly by a process comprising:

(a) producing a composition comprising a model RNA from a DNA template encoding the model RNA under identical IVT conditions as used to produce a IVT RNA, and (b) determining the amount of reverse complement transcription product or cytokine-inducing species by LC-MS in the composition comprising the model RNA, wherein the amount of reverse complement transcription product or cytokine-inducing species by LC-MS in the composition comprising the model RNA indicates the amount of reverse complement transcription product or cytokine-inducing species in the composition comprising the IVT RNA.

In other aspects the invention is an in vitro-transcribed (IVT) RNA composition wherein the RNA is not subject to RNaseIII treatments and/or is not subject to RP purification.

In yet other aspects the invention is a composition comprising an in vitro-transcribed (IVT) single stranded RNA encoding a polypeptide of interest and a pharmaceutically acceptable excipient, wherein greater than 98% of the RNA is single stranded and wherein the single stranded RNA comprises transcripts of different lengths. In some embodiments the single stranded RNA comprising transcripts of different lengths includes full length transcript and abortive transcripts. In some embodiments 80-98% of the single stranded non-full length transcript comprises abortive transcripts. In yet other embodiments 95-98% of the single stranded non-full length transcript comprises abortive transcripts.

A unit of use composition is provided in other aspects of the invention. The unit of use composition is an in vitro-transcribed (IVT) single stranded RNA encoding a polypeptide of interest and a pharmaceutically acceptable excipient, wherein the composition is free of residual organic solvents.

In other aspects the invention is a composition comprising an in vitro-transcribed (IVT) single stranded RNA encoding a polypeptide of interest and a pharmaceutically acceptable excipient, wherein the composition is non-immunogenic and wherein the single stranded RNA comprises transcripts of different lengths. In some embodiments the single stranded RNA comprising transcripts of different lengths includes full length transcript and fragment transcripts such as abortive transcripts. Fragment transcripts include for instance non-full length sense RNAs, truncated or prematurely terminated transcripts as well as abortive transcripts which are typically less than the first 25 nucleotides of a transcription product.

In other aspects, the invention is a method of preparing RNA comprising (a) forming a reaction mixture comprising a DNA template and NTPs including adenosine triphosphate (ATP), cytidine triphosphate (CTP), uridine triphosphate (UTP), guanosine triphosphate (GTP) and optionally guanosine diphosphate (GDP), and a buffer eg. a magnesium-containing buffer, and (b) incubating the reaction mixture under conditions such that the RNA is transcribed, wherein the concentration of at least one of GTP, CTP, ATP, and UTP is at least 2× greater than the concentration of any one or more of ATP, CTP or UTP or the reaction further comprises a nucleotide diphosphate (NDP) or a nucleotide analog and wherein the concentration of the NDP or nucleotide analog is at least 2× greater than the concentration of any one or more of ATP, CTP or UTP. In some embodiments the ratio of concentration of GTP to the concentration of any one ATP, CTP or UTP is at least 2:1, at least 3:1, at least 4:1, at least 5:1 or at least 6:1 to produce the RNA.

In some embodiments the ratio of concentration of GTP to concentration of ATP, CTP and UTP is 2:1, 4:1 and 4:1, respectively. In other embodiments the ratio of concentration of GTP to concentration of ATP, CTP and UTP is 3:1, 6:1 and 6:1, respectively. In yet other embodiments the reaction mixture comprises GTP and GDP and wherein the ratio of concentration of GTP plus GDP to the concentration of any one of ATP, CTP or UTP is at least 2:1, at least 3:1, at least 4:1, at least 5:1 or at least 6:1 in other embodiments the ratio of concentration of GTP plus GDP to concentration of ATP, CTP and UTP is 3:1, 6:1 and 6:1, respectively.

Any of the compositions described herein may be a reaction mixture, e.g., a mixture of an IVT reaction that has not been purified by other methods such as RP chromatography. In other aspects the compositions are final products ready for therapeutic administration to a subject.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 4 shows that T7 can be used to perform RNA-templated RNA transcription in the absence of DNA template which upon treatment confers an immunostimulatory product.

FIG. 5A shows a Capillary Electrophoresis analysis of RNase III treated hEPO G5 material. FIG. 5B shows a Capillary Electrophoresis analysis of RNase III treated hEPO G0 material.

FIG. 8A shows model RNA-4 subjected to RNase III treatment following IVT using the equimolar method and FIG. 8B shows model RNA-4 subjected to RNase III treatment following IVT with an excess of GTP.

FIG. 10D shows in vitro IFNbeta analysis of hEPO EQ G5 untreated or after RNase III treatment under equimolar conditions.

FIGS. 11A-11D show Capillary Electrophoresis analysis of RP fractionated hEPO Alpha +/−RIII treatment. FIGS. 11A, 11B and 11C show the effects of IVT with an excess of GTP in the reactions. FIG. 11D shows IVT with excess GTP, which resulted in no IFN response.

FIG. 25 shows the results of an IFN-β assay, analyzing short dsRNAs. The assay is an in vitro analysis of short 5' triphosphorylated oligos.

DETAILED DESCRIPTION

Figure 1:
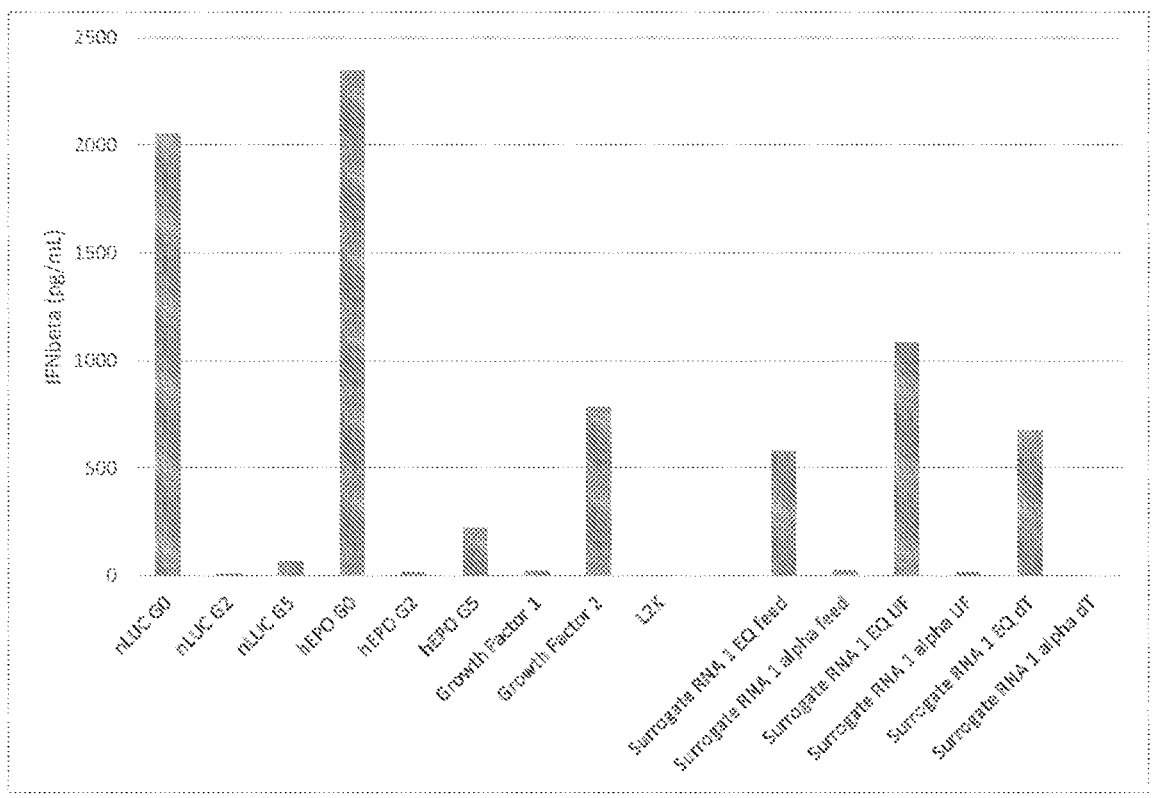
FIG. 1 is a graph depicting the results of an IFN-β assay screening hEPO chemistry variants, nLuc and vehicle controls as well as short model RNA-1 in BJ fibroblasts.

In order to enhance methods for manufacturing protein-coding polymers, new methods of generating RNA have been developed. It has been discovered that changes can be made to an in vitro transcription process to produce an RNA preparation having vastly different properties from RNA produced using a traditional in vitro transcription (IVT) process. The RNA preparations produced according to the methods of the invention (also referred to herein as the IVT RNA compositions) have properties that enable the production of qualitatively and quantitatively superior compositions comprising said RNA transcripts. Even when coupled with extensive purification processes, RNA produced using traditional IVT methods is qualitatively and quantitatively distinct from the RNA preparations of the invention. For instance, the RNA preparations of the invention (and compositions comprising same) are less immunogenic in comparison to RNA preparations (and compositions comprising same) made using traditional IVT. The RNA preparations produced according to the methods of the invention (also referred to herein as the IVT RNA compositions) further have properties that enable the production of qualitatively and quantitatively superior protein production, for instance, when translated. For instance, protein generated from the RNA preparations of the invention is less immunogenic in comparison to RNA preparations made using traditional WT.

Additionally, increased protein expression levels with higher purity are produced from the RNA preparations described herein. Although not bound by a mechanism, it is believed that substantial protein expression levels are a result of the high integrity of mRNA in the purified samples. While some purification procedures can effectively remove a level of contaminants by degradation of those contaminants, the integrity of the pharmaceutical product is negatively impacted. For instance, it is asserted in prior art that RNAse digestion of mRNA samples is useful for removing RNA contaminants. However, RNAse digestion also reduces the integrity of the mRNA by degrading portions of full length transcript produced by the IVT reaction. In contrast to the prior art IVT/purification processes the integrity of mRNA using the methods of the invention is quite high because the methods produce very little to no double stranded transcripts that would require removal using procedures such as RNAse digestion.

The RNA produced by the processes described herein is any RNA greater than 30 nucleotides in length which may be used for therapeutic or diagnostic purposes. In some embodiments the RNA is an RNA of greater than 40, 50, 60, 75, 100, 200, 300, 400, 500, or 1,000 nucleotides in length. In some embodiments the RNA is an RNA of greater than 1000, 2000, 3000, 4000, 5000, 6000, 7000, 8000, 9000, 10,000, 11,000, or 12,000 nucleotides in length. The RNA in some embodiments is mRNA. In some embodiments the RNA is an RNA of about 500 to about 4000 nucleotides in length, 1000 about to about 2000 nucleotides in length, 750 about to about 1800 nucleotides in length, about 1500 to about 3000 nucleotides in length, about 4000 to about 7000 nucleotides in length, or about 6000 to about 12000 nucleotides in length. The mRNA may be modified or unmodified. In other embodiments the RNA is one or more of the following: mRNA, modified mRNA, unmodified RNA, lncRNA, self-replicating RNA, circular RNA, CRISPR guide RNA.

Traditional IVT reactions are performed by incubating a DNA template with an RNA polymerase and equimolar quantities of nucleotide triphosphates, including GTP, ATP, CTP, and UTP in a transcription buffer. An RNA transcript having a 5' terminal guanosine triphosphate is produced from this reaction. These reactions also result in the production of a number of impurities such as double stranded and single stranded RNAs which are immunostimulatory and may have an additive impact. The methods of the invention which prevent formation of reverse complements prevent the innate immune recognition of both species. In some embodiments the methods of the invention result in the production of RNA having significantly reduced T cell activity than an RNA preparation made using prior art methods with equimolar NTPs. The prior art attempts to remove these undesirable components using a series of subsequent purification steps. Such purification methods are undesirable because they involve additional time and resources and also result in the incorporation of residual organic solvents in the final product, which is undesirable for a pharmaceutical product. It is labor and capital intensive to scale up processes like reverse phase chromatography (RP): utilizing for instance explosion proof facilities, HPLC columns and purification systems rated for high pressure, high temperature, flammable solvents etc. The scale and throughput for large scale manufacture are limited by these factors. Subsequent purification is also required to remove alkylammonium ion pair utilized in RP process. In contrast the methods described herein even enhance currently utilized methods (eg RP). Lower impurity load leads to higher purification recovery of full length RNA devoid of cytokine inducing contaminants eg. higher quality of materials at the outset. An additional advantage of the modified IVT processes of the invention, when using RNase III as a preparative purification, is that since there is less RNase III substrate, less inert/extraneous cleavage products (those that degrade but do not translate) are generated by RNase III treatment. If only trace amounts of dsRNA/RNase III substrate, even though may be cytokine silent, more final intact RNA product (intact cap/ORF/PolyA) capable of translating protein is present. This leads to a reduced burden for any subsequent purification.

It was discovered quite surprisingly, according to aspects of the invention, that the manipulation of one or more of the reaction parameters in the IVT reaction produces a RNA preparation of highly functional RNA without one or more of the undesirable contaminants produced using the prior art processes. One parameter in the IVT reaction that may be manipulated is the relative amount of a nucleotide or nucleotide analog in comparison to one or more other nucleotides or nucleotide analogs in the reaction mixture (e.g., disparate nucleotide amounts or concentration). For instance, the IVT reaction may include an excess of a nucleotides, e.g., nucleotide monophosphate, nucleotide diphosphate or nucleotide triphosphate and/or an excess of nucleotide analogs and/or nucleoside analogs. The methods of the invention produce a high yield product which is significantly more pure than products produced by traditional IVT methods.

Nucleotide analogs are compounds that have the general structure of a nucleotide or are structurally similar to a nucleotide or portion thereof. In particular, nucleotide analogs are nucleotides which contain, for example, an analogue of the nucleic acid portion, sugar portion and/or phosphate groups of the nucleotide. Nucleotides include, for instance, nucleotide monophosphates, nucleotide diphosphates, and nucleotide triphosphates. A nucleotide analog, as used herein is structurally similar to a nucleotide or portion thereof but does not have the typical nucleotide structure (nucleobase-ribose-phosphate). Nucleoside analogs are compounds that have the general structure of a nucleoside or are structurally similar to a nucleoside or portion thereof. In particular, nucleoside analogs are nucleosides which contain, for example, an analogue of the nucleic acid and/or sugar portion of the nucleoside.

A nucleoside triphosphate, as used herein, refers to a molecule including a nucleobase linked to a ribose (i.e. nucleoside) and three phosphates (i.e. nucleotide). A nucleotide diphosphate refers to the same molecule, but which has two phosphate moieties. A nucleotide monophosphate refers to the same molecule, but which has one phosphate moiety. The nucleotide monophosphate, nucleotide diphosphate and triphosphate are sometimes referred to herein as NMP, NDP and NTP, respectively. The N in NMP, NDP and NTP refer to any nucleotide, including naturally occurring nucleotides, synthetic nucleotides, and modified nucleotides. Thus the terms NDP and NTP refer to nucleotide diphosphates and nucleotide triphosphates, respectively, having any naturally occurring, synthetic, or modified nucleotide therein.

Natural nucleotide diphosphates include at least adenosine diphosphate (ADP), guanosine diphosphate (GDP), cytidine diphosphate (CDP), and uridine diphosphate (UDP). Natural nucleotide triphosphates include at least adenosine triphosphate (ATP), guanosine triphosphate (GTP), cytidine triphosphate (CTP), 5-methyluridine triphosphate (m5UTP), and uridine triphosphate (UTP). In some embodiments the NDP and/or NTP are modified. For instance, modified NDP or NTP may have a handle to enable easy purification and isolation.

Nucleotide triphosphates are added to the RNA strand by a polymerase such as T7 polymerase. Nucleotide diphosphates and monophosphates, in contrast can initiate the reaction (e.g., serve as the first transcribed monomer) but won't be incorporated within the strand by T7 polymerase (e.g., won't be incorporated anywhere else in the strand). In some instances the nucleotide diphosphates, such as GDP, may be incorporated as the first monomer. For instance if T7 initiates with GDP and produces a 5'GDP a functional RNA may be generated. 5' GDP initiated RNA is still a substrate for vaccinia capping enzyme. When an excess of NMP such as GMP is used in the reaction the purity may be enhanced by ligating a cap on, as the transcribed product with 5' PO4 is a substrate for ligase(s) (e.g., DNA/RNA ligase(s)).

The nucleotide analogs useful in the invention are structurally similar to nucleotides or portions thereof but, for example, are not polymerizable by T7. Nucleotide/nucleoside analogs as used herein (including C, T, A, U, G, dC, dT, dA, dU, or dG analogs) include for instance, antiviral nucleotide analogs, phosphate analogs (soluble or immobilized, hydrolyzable or non-hydrolyzable), dinucleotide, trinucleotide, tetranucleotide, e.g., a cap analog, or a precursor/substrate for enzymatic capping (vaccinia, or ligase), a nucleotide labelled with a functional group to facilitate ligation/conjugation of cap or 5' moiety (IRES), a nucleotide labelled with a 5' PO4 to facilitate ligation of cap or 5' moiety, or a nucleotide labelled with a functional group/protecting group that can be chemically or enzymatically cleavable. Antiviral nucleotide/nucleoside analogs include but are not limited to Ganciclovir, Entecavir, Telbivudine, Vidarabine and Cidofovir.

IVT Reaction Conditions

In exemplary aspects, the methods of the invention involve the production of RNA via an IVT reaction. IVT is an art-recognized method used to generate synthetic polynucleotides in vitro. In vitro transcribed (IVT) RNA can be engineered to transiently express proteins by structurally resembling natural RNA. However, there are inherent challenges of this drug class, particularly related to controlling the translational efficacy and immunogenicity of the IVT RNA. In particular, IVT RNA produces unwanted innate immune effects and there are very stringent purification procedures by HPLC that are typically applied as an additional, final RNA production step. The removal of minor amounts of short double stranded RNA fragments is critically important to achieve this further reduced immune response.

The typical reaction used in the prior art provides a high fidelity reasonably high yield product. However, the product has a baseline level of contaminants, only some of which can be removed using routine purification methods. The IVT reaction typically includes the following: an RNA polymerase, e.g., a T7 RNA polymerase at a final concentration of, e.g., 1000-12000 U/mL, e.g., 7000 U/mL; the DNA template at a final concentration of, e.g., 10-70 nM, e.g., 40 nM; nucleotides (NTPs) at a final concentration of e.g., 0.5-10 mM, e.g., 7.5 mM each; magnesium at a final concentration of, e.g., 12-60 mM, e.g., magnesium acetate at 40 mM; a buffer such as, e.g., HEPES or Tris at a pH of, e.g., 7-8.5, e.g. 40 mM Tris HCl, pH 8. In some embodiments 5 mM dithiothreitol (DTT) and/or 1 mM spermidine may be included. In some embodiments, an RNase inhibitor is included in the IVT reaction to ensure no RNase induced degradation during the transcription reaction. For example, murine RNase inhibitor can be utilized at a final concentration of 1000 U/mL. In some embodiments a pyrophosphatase is included in the IVT reaction to cleave the inorganic pyrophosphate generated following each nucleotide incorporation into two units of inorganic phosphate. This ensures that magnesium remains in solution and does not precipitate as magnesium pyrophosphate. For example, an E. coli inorganic pyrophosphatase can be utilized at a final concentration of 1 U/mL.

A typical in vitro transcription reaction includes the following:

| 1 | Template cDNA | 1.0 µg |
|---|---|---|
| 2 | 10x transcription buffer (400 mM Tris-HCl pH 8.0, 190 mM MgCl2, 50 mM DTT or TCEP, 10 mM Spermidine) | 2.0 µl |
| 3 | Custom NTPs (25 mM each) | 7.2 µl |
| 4 | RNase Inhibitor | 20 U |
| 5 | T7 RNA polymerase | 3000 U |
| 6 | dH$_2$0 | Up to 20.0 µl. and |
| 7 | Incubation at 37° C. for 1 hr-5 hrs. | |

The crude IVT mix may be stored at 4° C. for 4-12 hours. One unit of RNase-free DNase is then used to digest the original template. After 15 minutes of incubation at 37° C., the RNA is purified using purification techniques such as dT resin, reverse phase HPLC or Ambion's MEGACLEAR™ Kit (Austin, Tex.) following the manufacturer's instructions. The exemplary IVT reaction is not limiting in terms of components or amounts of components used.

Similar to traditional methods, the RNA of the invention may also be produced by forming a reaction mixture comprising a DNA template, and one or more NTPs such as ATP, CTP, UTP, GTP (or corresponding analog of aforementioned components) and a buffer. The reaction is then incubated under conditions such that the RNA is transcribed. However, the methods of the invention involve the surprising finding that the presence of an excess amount of one or more nucleotides and/or nucleotide analogs can have significant impact on the end product. The methods of the invention can be used to produce high quality product lacking unintended or undesirable impurities and without impacting the efficacy of the reaction.

The IVT methods of the invention involve a modification in the amount (e.g., molar amount or quantity) of nucleotides and/or nucleotide analogs in the reaction mixture. In some aspects, one or more nucleotides and/or one or more nucleotide analogs may be added in excess to the reaction mixture. An excess of nucleotides and/or nucleotide analogs is any amount greater than the amount of one or more of the other nucleotides such as NTPs in the reaction mixture. For instance, an excess of a nucleotide and/or nucleotide analog may be a greater amount than the amount of each or at least one of the other individual NTPs in the reaction mixture or may refer to an amount greater than equimolar amounts of the other NTPs.

In the embodiment when the nucleotide and/or nucleotide analog that is included in the reaction mixture is an NTP, the NTP may be present in a higher concentration than all three of the other NTPs included in the reaction mixture. The other three NTPs may be in an equimolar concentration to one another. Alternatively one or more of the three other NTPs may be in a different concentration than one or more of the other NTPs.

In some embodiments, the excess of the selected NTP is 2 times or fold (×), 3×, 4×, 5×, 6×, 7×, 8×, 9×, 10×, 11×, 12×, 13×, 14×, 15×, 15×-100×, 10×-90×, 10×-80×, 10×-70× or even greater than the amount of any one or more of the other individual NTPs in the reaction mixture. In other embodiments, the excess of the selected NTP is 2 times or fold (×), 3×, 4×, 5×, 6×, 7×, 8×, 9×, 10×, 11×, 12×, 13×, 14×, 15×, 15×-100×, 10×-90×, 10×-80×, 10×-70× or even greater than the amount of the total of the other individual NTPs in the reaction mixture. In exemplary embodiments, the NTP is in a molar excess relative to other NTPs in the reaction mixture. For example, the NTP in excess can be added at a molar ratio, e.g., 2:1, 3:1, 4:1, 5:1, 6:1, 7:1, 8:1, 9:1, 10:1, 11:1, 12:1, 13:1, 14:1, 15:1, or greater than one or more of the other NTPs in the reaction mixture. In other embodiments, the excess of the selected NTP is in a concentration of 0.5 mM, 1.0 mM, 1.5 mM, 2.0 mM, 2.5 mM, 3.0 mM, 3.54.0 mM, 4.5 mM, 5.0 mM, 5.5 mM, 6.0 mM, 7 mM, 8 mM, 9 mM, 10 mM, 15 mM, 20 mM, 30 mM, 40 mM, 50 mM, 60 mM, 70 mM, 100 mM, 120 mM, 150 mM, or even greater than the amount of any one or more of the other individual NTPs in the reaction mixture or in a range of 60-100 mM or 4.5-100 mM. In other embodiments, the excess of the selected NTP is in a concentration of 0.5 mM, 1.0 mM, 1.5 mM, 2.0 mM, 2.5 mM, 3.0 mM, 3.54.0 mM, 4.5 mM, 5.0 mM, 5.5 mM, 6.0 mM, 7 mM, 8 mM, 9 mM, 10 mM, 15 mM, 20 mM, 30 mM, 40 mM, 50 mM, 60 mM, 70 mM, 100 mM, 120 mM, 150 mM or even greater than the amount of any one or more of the sum of the other NTPs in the reaction mixture.

In some instances, the NTP in excess in the reaction mixture is NTP-1 and the other NTPs in the reaction mixture are NTP-2, NTP-3, and NTP-4. In some embodiments NTP-1 is present in the reaction mixture in a greater concentration than NTP-2, NTP-3, and NTP-4 and wherein NTP-2, NTP-3, and NTP-4 are each in an equimolar amount. In some embodiments the ratio of NTP-1:NTP-2:NTP-3:NTP-4 is at least 2:1:1:1, at least 3:1:1:1, at least 4:1:1:1, at least 5:1:1:1, at least 6:1:1:1, at least 7:1:1:1, at least 8:1:1:1, at least 9:1:1:1, at least 10:1:1:1, at least 11:1:1:1, at least 12:1:1:1, at least 13:1:1:1, at least 14:1:1:1, at least 15:1:1:1, at least 16:1:1:1, at least 17:1:1:1, at least 18:1:1:1, at least 19:1:1:1, each with a potential upper cap of NTP-1 as 20. In some embodiments the ratio of NTP-1:NTP-2+NTP-3+NTP-4 is at least 3:3, at least 5:3, at least 6:3, at least 7:3, at least 8:3, at least 9:3, at least 10:3, or at least 15:3, each with a potential upper cap of 20:3.

In other embodiments NTP-1 is present in the reaction mixture in a greater concentration than NTP-2, NTP-3, and NTP-4 and NTP-2 and NTP-3 are each in an equimolar amount and NTP-4 is present in the reaction mixture in a concentration higher than NTP-2 and NTP-3 and less than NTP-1. For instance, in some embodiments the ratio of NTP-1:NTP-4:NTP-2:NTP-3 is at least 3:2:1:1, at least 4:3:1:1, at least 4:2:1:1, at least 5:3:1:1, at least 5:3:2:2, at least 6:4:2:2, at least 8:4:2:2, at least 9:2:1:1, at least 10:2:1:1, at least 11:2:1:1, at least 12:2:1:1, at least 13:2:1:1, at least 14:2:1:1, at least 15:2:1:1, at least 16:2:1:1, at least 17:2:1:1, at least 18:2:1:1, at least 19:2:1:1, each with a potential upper cap of NTP-1 as 20.

In other embodiments NTP-1 is present in the reaction mixture in a greater concentration than NTP-2, NTP-3, and NTP-4 and NTP-2 and NTP-3 are each in an equimolar amount and NTP-4 is present in the reaction mixture in a concentration less than NTP-1, NTP-2 and NTP-3. For instance, in some embodiments the ratio of NTP-1:NTP-3:NTP-2:NTP-4 is at least 3:2:2:1, at least 4:3:3:1, at least 4:2:2:1, at least 5:3:3:1, at least 5:3:3:2, at least 6:4:4:2, at least 8:4:4:2, at least 9:2:2:1, at least 10:2:2:1, at least 11:2:2:1, at least 12:2:2:1, at least 13:2:2:1, at least 14:2:2:1, at least 15:2:2:1, at least 16:2:2:1, at least 17:2:2:1, at least 18:2:2:1, at least 19:2:2:1, each with a potential upper cap of NTP-1 as 20.

NTP-1 in some embodiments is GTP, ATP, UTP, or CTP. NTP-2 in some embodiments is GTP, ATP, UTP, or CTP. NTP-3 in some embodiments is GTP, ATP, UTP, or CTP. NTP-4 in some embodiments is GTP, ATP, UTP, or CTP.

In some embodiments, the NTP is GTP and it is present in the mixture at a ratio of at least 2:1, at least 3:1, at least 4:1, at least 5:1, at least 6:1, at least 7:1, at least 8:1, at least 9:1, at least 10:1, at least 11:1, at least 12:1, at least 13:1, at least 14:1, or at least 15:1 relative to the concentration of any one of ATP, CTP, or UTP. The ratio of GTP to other NTPs may be from about 2:1 to about 3:1, from about 2.5:1 to about 3.5:1, from about 3:1 to about 4:1, from about 3.5:1 to about 4.5:1, from about 4:1 to about 5:1, from about 4.5:1 to about 5.5:1, from about 5:1 to about 6:1, from about 5.5:1 to about 6.5:1, from about 6:1 to about 7:1, from about 6.5:1 to about 7.5:1, from about 7:1 to about 8:1, from about 7.5:1 to about 8.5:1, from about 8:1 to about 9:1, from about 8.5:1 to about 9.5:1, and from about 9:1 to about 10:1. In an embodiment, the ratio of concentration of GTP to the concentration of ATP, CTP, and UTP may be 2:1, 4:1, and 4:1, respectively. In another embodiment, the ratio of concentration of GTP to the concentration of ATP, CTP, and UTP may be 3:1, 6:1, and 6:1, respectively.

In the embodiment when the nucleotide and/or nucleotide analog that is included in the reaction mixture is an NDP or a nucleotide analog, the NDP or nucleotide analog may be present in a higher concentration than all four of the NTPs included in the reaction mixture. The four NTPs may be in an equimolar concentration to one another. Alternatively one or more of the four NTPs may be in a different concentration than one or more of the other NTPs.

In other embodiments, the excess of the selected NDP or nucleotide analog is 2 times or fold (×), 3×, 4×, 5×, 6×, 7×, 8×, 9×, 10×, 11×, 12×, 13×, 14×, 15×, 15×-100×, 10×-90×, 10×-80×, 10×-70× or even greater than the amount of any one or more of the individual NTPs in the reaction mixture. In other embodiments, the excess of the selected NDP or nucleotide analog is 2 times or fold (×), 3×, 4×, 5×, 6×, 7×, 8×, 9×, 10×, 11×, 12×, 13×, 14×, 15×, 15×-100×, 10×-90×, 10×-80×, 10×-70× or even greater than the amount of the total of the individual NTPs in the reaction mixture. In exemplary embodiments, the NDP or nucleotide analog is in a molar excess relative to other NTPs in the reaction mixture. For example, the NDP or nucleotide analog in excess can be added at a molar ratio, e.g., 2:1, 3:1, 4:1, 5:1, 6:1, 7:1, 8:1, 9:1, 10:1, 11:1, 12:1, 13:1, 14:1, 15:1, or greater than one or more of the NTPs in the reaction mixture. In other embodiments, the excess of the selected NDP or nucleotide analog is in a concentration of 0.5 mM, 1.0 mM, 1.5 mM, 2.0 mM, 2.5 mM, 3.0 mM, 3.54.0 mM, 4.5 mM, 5.0 mM, 5.5 mM, 6.0 mM, 7 mM, 8 mM, 9 mM, 10 mM, 15 mM, 20 mM, 30 mM, 40 mM, 50 mM, 60 mM, 70 mM, 100 mM, 120 mM, 150 mM, or even greater than the amount of any one or more of the individual NTPs in the reaction mixture or in a range of 60-100 mM or 4.5-100 mM. In other embodiments, the excess of the selected NDP or nucleotide analog is in a concentration of 0.5 mM, 1.0 mM, 1.5 mM, 2.0 mM, 2.5 mM, 3.0 mM, 3.54.0 mM, 4.5 mM, 5.0 mM, 5.5 mM, 6.0 mM, 7 mM, 8 mM, 9 mM, 10 mM, 15 mM, 20 mM, 30 mM, 40 mM, 50 mM, 60 mM, 70 mM, 100 mM, 120 mM, 150 mM or even greater than the amount of any one or more of the sum of the NTPs in the reaction mixture.

In some instances, the NTPs in the reaction mixture are NTP-1, NTP-2, NTP-3, and NTP-4. In some embodiments NDP or nucleotide analog is present in the reaction mixture in a greater concentration than NTP-1, NTP-2, NTP-3, and NTP-4 and wherein NTP-1, NTP-2, NTP-3, and NTP-4 are each in an equimolar amount. In some embodiments the ratio of NDP or nucleotide analog:NTP-1+NTP+2:NTP-3+NTP-4 is at least 4:4, at least 5:4, at least 6:4, at least 7:4, at least 8:4, at least 9:4, at least 10:4, or at least 15:4, each with a potential upper cap of 20:4.

In some embodiments the excess of NDP or nucleotide analog is combined with an equivalent or greater concentration of one of the four NTPs.

In other embodiments NDP or nucleotide analog is present in the reaction mixture in a greater concentration than NTP-1, NTP-2, NTP-3, and NTP-4 and NTP-1, NTP-2 and NTP-3 are each in an equimolar amount and NTP-4 is present in the reaction mixture in a concentration less than or greater than NTP-1, NTP-2 and NTP-3. For instance, in some embodiments the ratio of NDP or nucleotide analog: NTP-1:NTP-3:NTP-2:NTP-4 is at least 3:2:2:2:1, at least 4:3:3:3:1, at least 4:2:2:2:1, at least 5:3:3:3:1, at least 5:3:3:3:2, at least 6:4:4:4:2, at least 8:4:4:4:2, at least 9:2:2:2:1, at least 10:2:2:2:1, at least 11:2:2:2:1, at least 12:2:2:2:1, at least 13:2:2:2:1, at least 14:2:2:2:1, at least 15:2:2:2:1, at least 16:2:2:2:1, at least 17:2:2:2:1, at least 18:2:2:2:1, at least 19:2:2:2:1, each with a potential upper cap of NDP or nucleotide analog as 20.

In other embodiments NDP or nucleotide analog is present in the reaction mixture in a greater concentration than NTP-1, NTP-2, NTP-3, and NTP-4 and NTP-2 and NTP-3 are each in an equimolar amount and NTP-1 and/or NTP-4 are present in the reaction mixture in a concentration less than or greater than NTP-2 and NTP-3. In other embodiments NDP or nucleotide analog is present in the reaction mixture in a greater concentration than NTP-1, NTP-2, NTP-3, and NTP-4 and NTP-1, NTP-2, NTP-3, and NTP-4 are each present in a different amount from one another.

In some embodiments the upper limit of the excess of nucleotide or nucleotide analog in the reaction mixture is governed by the solubility limit.

In some embodiments the NTPs are salt NTPs. For instance the NTPs may be ammonium NTPs, tris NTPs, lithium NTPs, potassium NTPs, or sodium NTPs.

In one embodiment of the invention, the IVT method may involve the addition of a combination of NTP and NDP to the reaction mixture. The NTP and NDP in combination may be added in excess to the reaction mixture. An excess of the combination of NTP and NDP is any amount greater than the amount of one or more of at least one of the other NTPs or all of the other NTPs in the reaction mixture. For instance, an excess of NTP and NDP may be the combined amount that is greater amount than the amount of at least one of the other NTPs in the reaction mixture.

Thus, in some embodiments the IVT reaction may include an equimolar amount of nucleotide triphosphate relative to at least one of the other nucleotide triphosphates or less than an excess of nucleotide triphosphate when it is used in combination with a corresponding nucleotide diphosphate, as long as the total amount of that nucleotide is present in excess in the reaction. A corresponding nucleotide diphosphate refers to a nucleotide diphosphate having the same base as the nucleotide triphosphate. For example, the nucleotide triphosphate may be GTP and the nucleotide diphosphate may be GDP.

In some embodiments, the NTP and NDP in combination are equimolar. In another embodiment, the amount of NTP is greater than the amount of NDP in the combination added to the reaction mixture. The amount of NDP may be greater than the amount of NTP in the combination added to the reaction mixture. In some embodiments, the excess of the NTP and NDP combination mixture is 2 times or fold (×), 3×, 4×, 5×, 6×, 7×, 8×, 9×, 10×, 11×, 12×, 13×, 14×, 15×, 15×-100×, 10×-90×, 10×-80×, 10×-70× or even greater than the amount of the other individual NTPs in the reaction mixture. In each embodiment the other individual NTPs may be present in the same (equimolar) or different amounts in the reaction mixture. The fold difference described herein refers to a comparison with at least one, at least two or all three of the other NTPs in the reaction mixture.

In other embodiments, the NTP is 2 times or fold (×), 3×, 4×, 5×, 6×, 7×, 8×, 9×, 10×, 11×, 12×, 13×, 14×, 15×, 15×-100×, 10×-90×, 10×-80×, 10×-70× or even greater than the amount of the NDP in the reaction mixture. In yet other embodiments, the NDP is 2 times or fold (×), 3×, 4×, 5×, 6×, 7×, 8×, 9×, 10×, 11×, 12×, 13×, 14×, 15×, 15×-100×, 10×-90×, 10×-80×, 10×-70× or even greater than the amount of the NTP in the reaction mixture.

In each of the embodiments described herein, the NTP and NDP may be, for example, GTP and GDP, respectively, and may be present in the mixture in a concentration at least 6 times or fold (×), 7×, 8×, 9×, 10×, 11×, 12×, 13×, 14×, 15×, 15×-100×, 10×-90×, 10×-80×, 10×-70× or even greater than the amount of any one of ATP, CTP, or UTP in the reaction mixture. In exemplary embodiments, the NTP and NDP in combination are in a molar excess relative to the other individual NTPs in the reaction mixture. For example, the NTP and NDP combination mixture can be added at a molar ratio, e.g., 2:1, 3:1, 4:1, 5:1, 6:1, 7:1, 8:1, 9:1, 10:1, 11:1, 12:1, 13:1, 14:1, 15:1, or greater in the reaction mixture. The ratio of GTP and GDP to other NTPs may be from about 2:1 to about 3:1, from about 2.5:1 to about 3.5:1, from about 3:1 to about 4:1, from about 3.5:1 to about 4.5:1, from about 4:1 to about 5:1, from about 4.5:1 to about 5.5:1, and from about 5:1 to about 6:1. In one embodiment, the ratio of concentration of GTP to the concentration of ATP, CTP, and UTP may be 3:1, 6:1, and 6:1, respectively.

In other embodiments the ratio of NTP to NDP and in some embodiments GTP to GDP is considered relative to the ratio or purine nucleotide to pyrimidine nucleotide (Pu:Py) in the reaction mixture. In some embodiments the GTP:GDP to Pu:Py ratios are 2:1, 3:1, 4:1, 5:1, 6:1, 7:1, 8:1, 9:1, 10:1, 11:1, 12:1, 13:1, 14:1, 15:1, or greater in the reaction mixture.

In some embodiments, the buffer contains phosphate. The effective concentration of the phosphate is at least 150 mM, at least 160 mM, at least 170 mM, at least 180 mM, at least 190 mM, at least 200 mM, at least 210 mM, at least 220 mM, or at least 230 mM phosphate. In one embodiment, the effective concentration of phosphate is 180 mM. In another embodiment, the effective concentration of phosphate is 195 mM.

In another embodiment, the buffer contains magnesium. The buffer may have a ratio of the concentration of ATP plus CTP plus UTP plus GTP and optionally, GDP to molar concentration of $Mg^{2+}$ of at least 1.0, at least 1.1, at least 1.2, at least 1.25, at least 1.3, at least 1.4, at least 1.5, at least 1.6, at least 1.7, at least 1.75, at least 1.8, and at least 1.85 or 3. In other embodiments the ratio is 1.0, 1.1, 1.2, 1.25, 1.3, 1.4, 1.5, 1.6, 1.7, 1.75, 1.8, 1.85, 2, 2.1, 2.2, 2.3, 2.4, 2.5, 2.6, 2.7, 2.8, 2.9, or 3 or any range of these variables. In one embodiment, the ratio is 1.5. In another embodiment, the ratio is 1.88. In one embodiment, the ratio is 3.

In exemplary aspects of the invention, the IVT reaction (reaction mixture) includes an RNA polymerase, for example, T7, SP6, T3, etc. In some embodiments, the polymerase, e.g., T7 polymerase is included at a concentration of greater than 5 U/µl, greater than 10 U/µl, greater than 20 U/µl, greater than 50 U/µl, or greater than 100 U/µl. In some embodiments the polymerase, e.g., T7 polymerase, concentration is a range of from about 1 to about 250 U/µl of reaction mixture, e.g., from about 1 to about 100 U/µl or from about 100 to about 250 U/µl. In some embodiments, the T7 polymerase concentration is a range of from about 30 to about 60 U/µl, about 60 to about 80 U/µl, about 80 to about 100 U/µl, about 100 to about 150 U/µl or from about 150 to about 200 U/µl. In some embodiments, the polymerase, e.g., T7 polymerase is included at a concentration of 7, 14, 25, 50, 75, or 140.

As used herein, a DNA template refers to a polynucleotide template for RNA polymerase. The DNA template useful according to the methods described herein includes in some embodiments a gene of interest coding for, e.g., a polypeptide of interest. The DNA template in some embodiments includes a RNA polymerase promoter, e.g., a T7 promoter located 5' to and operably linked to the gene of interest and optionally a sequence coding for a poly A tail located 3' to the gene of interest.

RNA polymerases known in the art may be used in the methods of the present invention. RNA polymerases include but are not limited to, a phage RNA polymerase, e.g., a T7 RNA polymerase, a T3 RNA polymerase, an SP6 RNA polymerase, and/or mutant polymerases such as, but not limited to, polymerases able to incorporate modified nucleic acids. As a non-limiting example, the RNA polymerase may be modified to exhibit an increased ability to incorporate a 2'-modified nucleotide triphosphate compared to an unmodified RNA polymerase.

As used herein, "gene of interest" refers to a polynucleotide which encodes a polypeptide or protein of interest. Depending on the context, the gene of interest refers to a deoxyribonucleic acid, e.g., a gene of interest in a DNA template which can be transcribed to an RNA transcript, or a ribonucleic acid, e.g., a gene of interest in an RNA transcript which can be translated to produce the encoded polypeptide of interest in vitro, in vivo, in situ or ex vivo. A polypeptide of interest includes but is not limited to, biologics, antibodies, vaccines, therapeutic proteins or peptides, etc.

An "RNA transcript" refers to a ribonucleic acid produced by an IVT reaction using a DNA template and an RNA polymerase. In some embodiments the RNA transcript is an mRNA and typically includes the coding sequence for a gene of interest and a poly A tail. RNA transcript includes an mRNA. The RNA transcript can include modifications, e.g., modified nucleotides. As used herein, the term RNA transcript includes and is interchangeable with mRNA, modified mRNA "mmRNA" or modified mRNA, and primary construct.

Purity

RNA produced according to the methods of the invention is surprisingly pure and of high integrity. It has fewer contaminants than RNA preparations produced according to traditional IVT methods. In some embodiments it has fewer immune stimulating contaminants than RNA preparations produced according to traditional IVT methods. The contaminants are RNA fragments produced by the reaction other than the desired RNA. In some embodiments the RNA fragment contaminants are reverse complement transcription products and/or cytokine inducing RNA contaminants. In other embodiments the RNA fragment contaminants are double stranded RNA or immunogenic contaminants.

The RNA preparations of the invention in some embodiments have less contaminants than RNA preparations produced according to traditional IVT methods. In some embodiments the RNA preparations of the invention have at least 10%, 20%, 25%, 30%, 35%, 40%, 45%, 50%, 55%, 60%, 65%, 70%, 75%, 80%, 85%, 90%, 91%, 92%, 93%, 94%, 95% 96%, 97%, 98%, or 99% less contaminants than RNA preparations produced according to traditional IVT methods. In other embodiments the RNA preparations of the invention are substantially free of contaminants. In other embodiments the RNA preparations of the invention are 100% free of contaminants.

Thus, the invention in some aspects involves the preparation of an IVT RNA that is substantially free of reverse complement transcription product without the need for further purification steps. As used herein, the term "reverse complement transcription product" refers to an RNA molecule resulting from RNA-templated transcription. The reverse complement transcription product may be in some embodiments an RNA-templated transcription product. Without being bound in theory it is believed that the reverse complement product is predominantly or all RNA-templated transcription product. If the reverse complement product were composed of DNA-templated transcription product, the product would include, for example, nucleotide sequences complementary to the T7 promoter region from the DNA template. The reverse complement products characterized to date are predominantly free of sequences complementary to, for example, the T7 promoter region. In some embodiments the reverse complement transcription product is a double-stranded RNA (dsRNA), which may include one strand encoding a sequence which is a reverse complement of at least a portion of the IVT RNA. In other embodiments the reverse transcription complement product may be a dsRNA with one strand comprising a polyU sequence. Either the reverse complement strand encoding the polypeptide of interest or the strand encoding the polyU sequence may initiate with a 5' triphosphate (5'ppp). The RNA-template transcription product may include a reverse complement of the 5'-end of the IVT RNA and/or a reverse complement of the 3'-end of the IVT RNA. Furthermore, the reverse complement of the 5'-end of the IVT RNA may be complementary to all or a portion of a 5'UTR of the IVT RNA. The reverse complement may comprise a sequence complementary to the first 10-15, the first 5-15, the first 5-20, the first 10-20, the first 15-25 nucleotides of the 5'UTR. Likewise, the reverse complement of the 3'-end of the IVT RNA may be complementary to all or a portion of a polyA tail of the IVT RNA. The reverse complement transcription product can be templated from anywhere on the RNA and thus can be any size or complementary to any location on the template. For instance, the reverse complement product may be a 5-mer 10-mer 15-mer 20-mer 25-mer 40-mer 50-mer 60-mer 70-mer, 100-mer, 200-mer, etc. all the way up to the full length of the intended or desired product.

The present invention features compositions comprising an IVT RNA and a pharmaceutically acceptable excipient substantially free of reverse complement transcription product. In some embodiments, in the IVT RNA that is substantially free of reverse complement transcription product includes reverse complement transcription product that makes up less than about 10%, 9%, 8%, 7%, 6%, 5%, 4.5%, 4%, 3.5%, 3%, 2.5%, 2%, 1.5%, 1%, 0.9%, 0.8%, 0.7%, 0.6%, or 0.55%, 0.5%, 0.45%, 0.4%, 0.35%, 0.3%, 0.0.25%, 0.2%, 0.15%, 0.1%, 0.05%, 0.01%, 0.005%, or 0.001% of the mass of the total RNA. The mass of the RNA composition may be determined by any means known in the art. Examples of methods for determining the mass of the RNA include liquid chromatography and mass spectrometry.

Although not bound in theory, it is believed that in some embodiments of the invention the contaminants are single-stranded reverse complements bound to a population of the IVT RNAs forming a double stranded structure in the context of longer RNAs. T7 may template off of an abortive (sense strand) nascent RNA as well as full length product nascent RNA. The RNA-templated transcript (antisense), once transcribed (initiating predominantly with pppC, pppU, and pppA), presumably remains associated with the nascent sense RNA. Alternatively if such constructs do form they may be intrinsically silent. The association of the 2 strands effectively is dsRNA with 5'ppp. The presence of 5'ppp on one or more of the hybridized strands, renders the structure immunostimulatory. Even when the antisense RNA templated transcript is dissociated from the RNA, the presence of ssRNA with pppC, pppU, and pppA is still cytokine inducing. Since the methods of the invention produce RNA devoid of dsRNA as seen in J2 ELISA and RNase III treatment, the products would not assume a structure of large full length RNA. It is likely that the RNA is folding similarly if transcribed with equimolar or the inventive IVT process.

In some embodiments the RNA preparations of the invention are substantially free of cytokine-inducing RNA contaminant. As used herein, the term "cytokine-inducing contaminant" refers to an RNA molecule which induces cytokine generation, for example, type I interferon (IFNα/β induction), for example, as determined in a cell-based cytokine induction assay, for example, as determined in a BJ fibroblast/IFNbeta assay and/or Luminex assay as described in the working examples of the instant specification. In exemplary aspects of the invention, the term "cytokine-inducing" contaminant refers to an RNA molecule which induces cytokine induction and which is substantially double-stranded in nature.

Without being bound in theory, it is believed that double-stranded RNA molecules which result from aberrant polymerase transcription, for example, transcription templated off the desired RNA produced in an IVT reaction, induce cytokines via activation of an innate immune response akin to the natural antiviral immune response and includes two types of pathogen recognition receptors (PRRs): the Toll-like receptors (TLRs) and the RIG-I-like receptors (RLRs), for example, toll-like receptor 3 (TLR3), as well as the RNA helicases, for example, RIG-I and MDA5. Examples of other cytokine-inducing molecules include RNaseIII substrates. An RNase III substrate, as used herein, refers to a double stranded RNA molecule which is susceptible to cleavage by an RNase III enzyme.

In some embodiments, the cytokine-inducing RNA contaminant may be a double-stranded RNA with a reverse sequence complementary to the IVT RNA or a polyU sequence. The reverse complement of the IVT RNA or the polyU sequence may initiate with a 5'ppp.

The cytokine-inducing RNA contaminant may include a reverse complement of the 5'-end of the IVT RNA and/or a reverse complement of the 3'-end of the IVT RNA. Furthermore, the reverse complement of the 5'-end of the IVT RNA may be complementary to all or a portion of a 5'UTR of the IVT RNA. The reverse complement may comprise a sequence complementary to the first 10-15, the first 5-15, the first 5-20, the first 10-20, the first 15-25 nucleotides of the 5'UTR. In some embodiments the reverse complement may comprise a sequence complementary to a range of 1-20, 1-30, 1-40, 1-50, 1-60, 1-70, 1-80, 1-90, 1-100, 1-200, 1-300, 1-400, 1-500, 1-600, 1-700, 1-800, 1-900, 1-1000, 1-2000, 1-2500, or 1-3000 nucleotides in length within the 5'UTR. In other embodiments the reverse complement may comprise a sequence complementary to a range of 10-20, 10-30, 10-40, 10-50, 1-60, 10-70, 10-80, 10-90, 10-100, 10-200, 10-300, 10-400, 10-500, 10-600, 10-700, 10-800, 10-900, 10-1000, 10-2000, 10-2500, or 10-3000 nucleotides in length within the 5'UTR. In other embodiments the reverse complement may comprise a sequence complementary to a range of 20-25, 20-30, 20-40, 20-50, 20-60, 20-70, 20-80, 20-90, 20-100, 20-200, 20-300, 20-400, 20-500, 20-600, 20-700, 20-800, 20-900, 20-1000, 20-2000, 20-2500, or 20-3000 nucleotides in length within the 5'UTR. Likewise, the reverse complement of the 3'-end of the IVT RNA may be complementary to all or a portion of a polyA tail of the IVT RNA. The reverse complement may comprise a sequence complementary to the first 10-15, the first 5-15, the first 5-20, the first 10-20, the first 15-25 nucleotides of the 3'UTR. In some embodiments the reverse complement may comprise a sequence complementary to a range of 1-20, 1-30, 1-40, 1-50, 1-60, 1-70, 1-80, 1-90, 1-100, 1-200, 1-300, 1-400, 1-500, 1-600, 1-700, 1-800, 1-900, 1-1000, 1-2000, 1-2500, 1-3000, or 1-full length or maximum size of the RNA nucleotides in length within the 3'UTR. In other embodiments the reverse complement may comprise a sequence complementary to a range of 10-20, 10-30, 10-40, 10-50, 1-60, 10-70, 10-80, 10-90, 10-100, 10-200, 10-300, 10-400, 10-500, 10-600, 10-700, 10-800, 10-900, 10-1000, 10-2000, 10-2500, or 10-3000 nucleotides in length within the 3'UTR. In other embodiments the reverse complement may comprise a sequence complementary to a range of 20-25, 20-30, 20-40, 20-50, 20-60, 20-70, 20-80, 20-90, 20-100, 20-200, 20-300, 20-400, 20-500, 20-600, 20-700, 20-800, 20-900, 20-1000, 20-2000, 20-2500, or 20-3000 nucleotides in length within the 3'UTR.

The present disclosure includes a composition comprising an IVT RNA and a pharmaceutically acceptable excipient substantially free of cytokine-inducing RNA contaminant. In some embodiments, the cytokine-inducing RNA contaminant makes up less than 0.5%, 0.45%, 0.4%, 0.35%, 0.3%, 0.25%, 0.2%, 0.15%, 0.1%, 0.05%, 0.01%, 0.005%, or 0.001% of the mass of the RNA. The mass of the RNA composition may be determined by any means known in the art. Examples include liquid chromatography and mass spectrometry.

The dsRNA of the contaminant such as the cytokine-inducing RNA contaminant and/or the reverse complement transcription product may be 20 to 50 nucleotides in length. In other embodiments, the dsRNA may be 20-25, 25-30, 30-35, 35-40, 40-45, 45-50, 50-55, 55-60, 60-65, 65-70, 70-75, 75-80, 80-85, 85-90, 90-95, 95-100, 100-110, 110-120, 120-130, 130-140, 140-150, 150-160, 160-170, 170-180, 180-190, 190-200, 200-225, 225-250, 250-275, 275-300, 300-325, 325-350, 350-375, 375-400, 400-425, 425-450, 450-475, 475-500, 500-550, 550-600, 600-650, 650-700, 700-750, 750-800, 800-850, 850-900, 900-950, and 950-1000 nucleotides in length. In some embodiments, the mass of the dsRNA is greater than 40 base pairs and makes up less than about 0.5% of the RNA composition.

The contaminant strands may have 5'ppp ends. In some embodiments, the contaminant strands may have a lower abundance of pppA, pppC, and pppU, as compared to equimolar process-produced RNA. In another embodiment, the contaminant strands may have lower ratios of pppA:pppG, pppC:pppG, and/or pppU:pppG as compared to equimolar processes. pppNTPs may be detected by LC-MS following total nuclease digestion e.g. Nuclease P1 treatment. Nuclease P1 digests RNA and DNA into single nucleotides. The only triphosphate species that should be present are for the initiating nucleotides. If no RNA templated transcription products are formed, 5'PPPG is the only triphosphate that should be present as this is the only targeted site of initiation. Presence and abundance of 5'pppA, 5'pppC, and/or 5'pppU as detected by LC/MS following Nuclease P1 digestion are indicative of RNA templated RNA transcripts.

In addition to having less impurities, particularly double stranded impurities, the IVT RNA compositions have a high proportion of full length functional RNA transcript relative to other RNA species in the composition, particularly when compared to traditional purified RNA compositions produced using IVT methods combined with purification steps such as reverse phase chromatography or RNAse III treatment. In some embodiments greater than about 80%, 85%, 90%, 91%, 92%, 93%, 94%, 95%, 96%, 97%, 98%, 99%, 99.5% or 99.8% of the mass of the RNA comprises single stranded full length transcripts. In addition to the single stranded full length transcripts, the IVT RNA composition may include other single stranded RNA species such as single stranded partial RNA transcripts in a sense orientation, including abortive transcripts. The IVT RNA composition, however, is substantially free of RNAse III insensitive fragments.

The RNA compositions described herein may include other components besides the full length RNA transcript, e.g., truncated transcripts and/or run-on transcripts. For instance, the RNA may include transcripts of different lengths, e.g., shorter or longer than the full-length transcript. Thus, in some embodiments the RNA preparation of the invention includes truncated and/or abortive transcripts. RNA polymerase binds to a DNA promoter and synthesizes the short mRNA transcripts. As used herein, the term "truncated transcripts" refers to transcripts having identity to the IVT RNA, but being of insufficient length and lacking all required elements to encode the polypeptide of interest (eg poly A). In certain instances, truncated transcripts are released prior to the transcription complex leaving the promoter, termed abortive transcripts. As used herein, the term "abortive transcripts" refers to transcripts having identity to the IVT RNA, but being of insufficient length and lacking all required elements to encode the polypeptide of interest (eg poly A), generally having a length of 15 nucleotides or less. In exemplary aspects of the invention, the truncated and/or abortive transcripts are present and are not cytokine-inducing. In an embodiment, the truncated and/or abortive transcripts are removed from the sample. In some embodiments truncated transcripts have a length of 100 nucleotides or less.

The methods of the instant invention also have been determined to produce compositions having reduced 3' heterogeneity or 3' end heterogeneity, also referred to herein as increased 3' homogeneity, or 3' end homogeneity. It was determined by the present inventors that traditional equimolar IVT reaction conditions can produce transcripts terminating at different 3' residues (e.g., transcription not uniformly terminating). An assay featured in the Working Examples was developed to detect the 3' end heterogeneity resulting from traditional IVT reactions (the assay differentiating between non-A nucleobases occurring at the 3' end of a particular test transcript). Notably, the methods of the instant invention produce transcripts having a lower degree of 3' end heterogeneity (or more homogeneous 3' ends). For example, transcripts produced according to traditional IVT reactions (e.g., equimolar reactions) can produce compositions in which greater than 50% of the transcripts (optionally greater than 60%, greater than 70%, greater than 75%, greater that 80% or more) have different ends, whereas transcripts produced according to the IVT reactions of the invention (e.g., alpha reactions) can produce compositions in which less than 50% of the transcripts, i.e., greater than 50% of the transcripts have the same ends, i.e., terminate at the same nucleobase (e.g., relative to the DNA template) (optionally less than 40%, less that 30%, less than 25%, less than 20% or less) have different ends).

The truncated transcripts within the population of single stranded partial RNA transcripts may include a range of sizes. For instance, in some embodiments, at least 80% of the population of truncated transcripts have a length of 100 nucleotides or less. In other embodiments at least 50%, 60%, 70%, 85%, 90%, 95%, 98% or 100% of the population of truncated transcripts have a length of 100 nucleotides or less.

The single stranded RNA population within the IVT RNA compositions described herein typically are free or substantially free of RNAse III insensitive fragments. An "RNAse III insensitive fragment" as used herein refers to single stranded transcripts having identity to the IVT RNA (sense orientation), but being of insufficient length and lacking all required elements to encode the polypeptide of interest (having less nucleotides than full length transcripts) and wherein the fragment is produced by enzymatic, in particular RNAse III, cleavage. The production of RNAse III insensitive fragments can result, for example, in a traditional IVT process (as depicted in FIG. 40) coupled with an RNAse III digestion.

Figure 40:
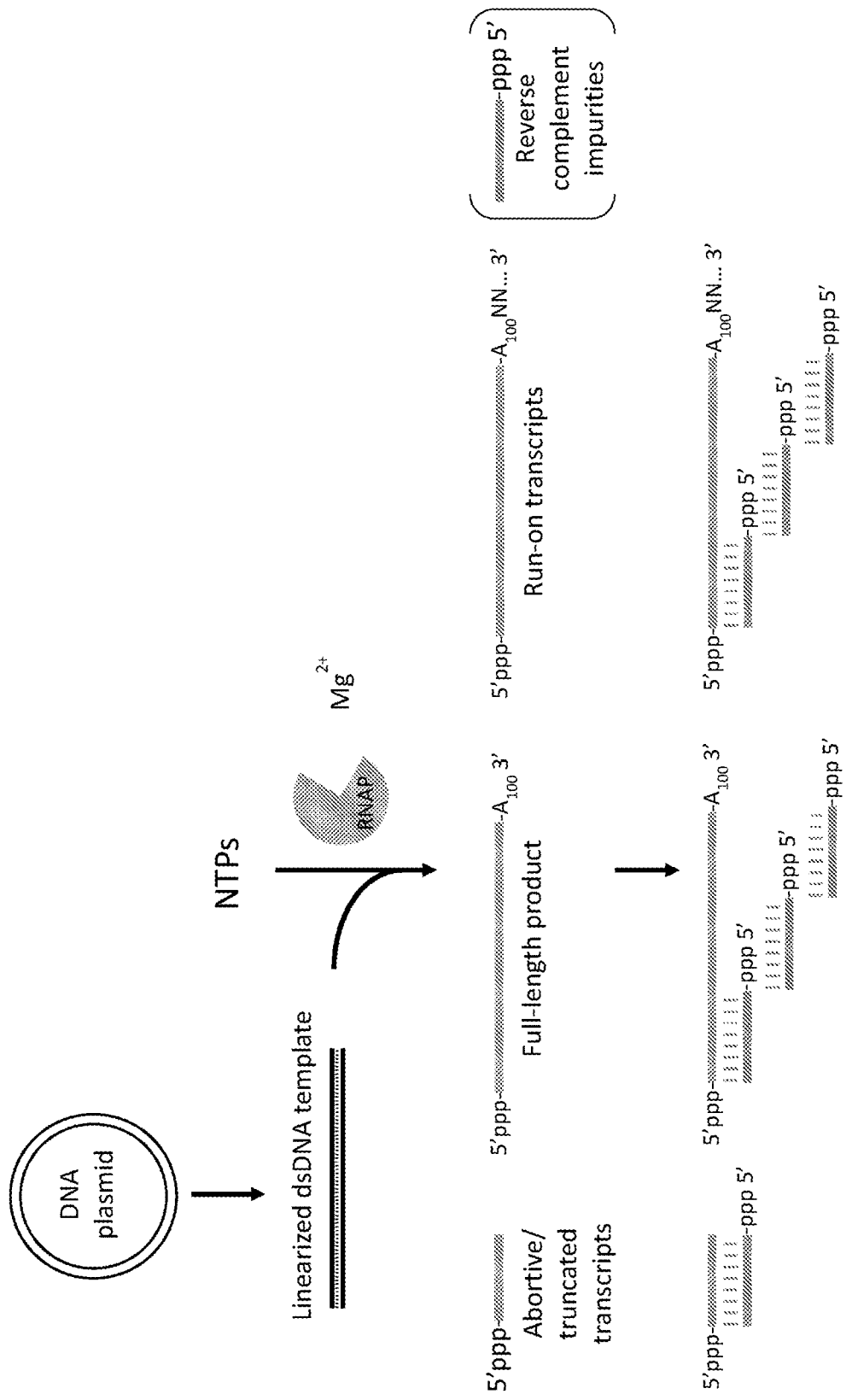
FIG. 40 is a schematic depicting a traditional in vitro transcription (IVT) process and types of impurities formed.

As shown in FIG. 40 a first step in a traditional IVT/RNAse III purification process involves a transcription reaction utilizing linear dsDNA template, equimolar concentrations of NTPs and RNA polymerase in the presence of $Mg^{2\pm}$. The reaction produces a mixed population of single stranded truncated/abortive transcripts, full length RNA transcript, run-on transcripts and reverse complement impurities. The reverse complement impurities can bind to some of the single stranded RNA or to other impurities, e.g., truncated transcripts, producing double stranded RNA and/or RNA having both double and single stranded regions. It has been postulated in the art that RNAse III can be used to degrade the double stranded RNA from IVT compositions, thus effectively removing it from the composition. However, RNAse III can also degrade double stranded regions of full length RNA transcript and/or run-on transcripts (e.g., double stranded regions resulting from reverse complements binding within polyA tail regions), leaving single stranded fragments having a length of less than the full length RNA transcripts. These single stranded fragments are the RNAse III insensitive fragments described herein. As a result of this RNAse degradation significant amounts of full length transcripts generated during the IVT process are lost, causing significant loss of product integrity. These compositions have significantly lower ability to express protein when delivered to a cell or subject.

RNAse III insensitive fragments generated following RNAse III treatment of products generated according to methods such as those depicted in FIG. 40 may include a range of sizes. For instance, in some embodiments, at least 80% of the population of abortive transcripts have a length of greater than 100 nucleotides. In other embodiments at least 50%, 60%, 70%, 85%, 90%, 95%, 98% or 100% of the population of RNAse III insensitive fragments have a length of greater than 100 nucleotides.

Without being bound in theory, it is believed that the removal of certain species or contaminants, for example, dsRNA species or contaminants, is important in the preparation of IVT RNA compositions for therapeutic use. By contrast, the presence of residual truncated and/or abortive transcripts in IVT RNA compositions is not believed to be required; such species are not believed to induce unwanted cytokines and/or an innate immune response to the IVT RNA. In other embodiments the RNA preparation of the invention is substantially free of truncated or abortive transcripts.

Although truncated/abortive transcripts may be present in the IVT RNA compositions or the invention, RNAse III insensitive fragments are not present in the IVT RNA compositions because the composition is not treated with RNAse III. While truncated transcripts and RNAse III insensitive fragments both have a range of sizes or lengths, the average length of truncated transcripts is less than the average length of RNAse III insensitive fragments. As such, when the composition comprises a population of single stranded partial RNA transcripts in a sense orientation and greater than 80% of the population of single stranded partial RNA transcripts in a sense orientation has a nucleotide length of 100 nucleotides or less. In some embodiments greater than 90%, 91%, 92%, 93%, 94%, 95%, 96%, 97%, 98%, 99% or 100% of the population of single stranded partial RNA transcripts in a sense orientation has a nucleotide length of 100 nucleotides or less. In other embodiments greater than 50%, 55%, 60%, 65%, 70%, 75%, 85%, or 88% of the population of single stranded partial RNA transcripts in a sense orientation has a nucleotide length of 100 nucleotides or less.

In some embodiments the RNA preparation is a pharmaceutical composition with a pharmaceutically acceptable carrier. In other embodiments the RNA preparation is a reaction product (e.g., IVT reaction product) which has not yet been subjected to further purification techniques. The RNA preparation may include a number of other components in addition to the RNA. The reaction product, however, is substantially free of reverse complement transcription product and/or cytokine inducing RNA contaminants.

Assays

The amount of contaminant, including reverse complement transcription product and/or cytokine-inducing RNA contaminant, may be determined by methods known in the art. Many methods for determining the purity of a nucleic acid sample are known in the art. Exemplary methods include, but are not limited to, the following: high-performance liquid chromatography (such as reverse-phase chromatography, size-exclusion chromatography), gel electrophoresis, and translational assays to assess the quality and purity of nucleic acid production. RNA preparation quality can also be determined using Bioanalyzer chip-based electrophoresis system. In vitro efficacy can be analyzed by, e.g., transfecting RNA transcript into a human cell line, e.g., HeLA, PBMC, BJ Fibroblasts, Hek 293). Protein expression of the polypeptide of interest can be quantified using methods such as Enzyme-Linked Immunosorbant Assay (ELISA), western blot, or flow cytometry.

A variety of methods have been used to detect and/or quantitate dsRNA using dsRNA-specific antibodies. These include ELISA, for example, sandwich ELISA (Schonborn et al. (1991) Nucleic Acids Res 19:2993-3000), dot-blots (for quantitation, specificity testing) (Kariko et al. (2011) Nucleic Acids Res 39:e142), and immunoprecipitation/immunoblotting. In exemplary aspects of the invention, contaminants may be recognized using an ELISA. A K1/J2 or K2/J2 assay may be used to determine the abundance of dsRNA contaminants in a sample. An exemplary ELISA is a sandwich ELISA, as follows. Blocking: Microtiter plates are pre-coated with protein, e.g., 0.4 µg/well protein A at 4° C. overnight. Free binding sites are saturated with bovine serum albumin (BSA) (e.g., 2%) in buffer (e.g.) PBS and the plates are then washed with buffer (e.g., PBS) and stored at 4° C. The dsRNA-specific J2 monoclonal antibody (IgG2a) is immobilized onto the protein A layer by incubation of hybridoma supernatant (e.g. 100 µl per well at 4° C. overnight. The plates are washed multiple times with buffer, e.g., PBS plus Tween 20 (e.g., 0.5% (v/v) Tween 20) and nucleic acid samples are added in buffer (e.g., TE buffer, 37° C., 2 h). After washing as above, bound nucleic acid (i.e., J2 antigens) are identified by successive incubation with the diluted hybridoma supernatant (e.g., 1:2) of the dsRNA-specific K2 lgM monoclonal antibody followed by an alkaline phosphatase conjugated secondary antibody (e.g., 1:5000 diluted goat anti-mouse lgM). Both incubation steps are carried out al 37° C. for ~1-2 h. Washing, substrate incubation and reading of absorption are performed according to art recognized methods.

A similar assay using dot blots is described by Kariko et al., Nuc. Acids Res. 2011; 39(21):e142. The assay is performed by blotting RNA (200 ng) onto super-charged Nytran membranes, where it is dried and blocked with 5% non-fat dried milk in TBS-T buffer (50 mM Tris-HCl, 150 mM NaCl, 0.05% Tween-20, pH 7.4). The sample is then incubated with a dsRNA-specific K1 or J2 monoclonal antibody (IgG) for one hour. The membranes may be washed with TBS-T and incubated with an HRP-conjugated anti-goat polyclonal antibody, for example. The membranes are washed again, and the signal is detected using TMB. The signal is developed with the addition of TMB. The assay is useful for detecting dsRNA duplexes greater than 40 base pairs in length.

Cytokine assays may also be used to detect RNA contaminants. Numerous cytokine assays are known in the art. The assays may test for the induction of any cytokine associated with impure IVT products. These cytokines include for instance, interleukins (IL), interference (IFN) alphas, beta, and gamma, and TNF. In one embodiment, an IFN-β cell-based assay may be used. Its results have been shown to correlate with the presence of RNaseIII substrate as detected by LC-MS. Other cell-based cytokine assays, such as for example IL or multiplex cytokine assays may be used.

In exemplary BJF IFN-beta and hEPO expression assays BJ Fibroblasts cells (ATCC) are seeded in a cell culture plate. Approximately 24 hours after seeding, the cells are transfected with mRNA using lipofectamine or other delivery agent. After transfection, supernatants are collected and IFN-beta expression iss measured using the human IFN-beta ELISA kit, High Sensitivity per manufacturer's instructions (PBL Assay Science). Briefly, human IFN-β is measured in cell supernatants by indirect enzyme linked immunosorbent assay (ELISA). Pre-coated plates are incubated with cell supernatants then washed to remove non-specifically bound material. IFN-β expression is analyzed by incubating the wells with anti-IFN-β antibody followed by a secondary antibody conjugated to horseradish peroxidase (HRP). Tetramethylbenzidine (TMB) is the HRP substrate used for detection. Human Epo levels are measured using Epo Human ELISA Kit (Thermo Fisher).

In exemplary Luminex assays, serum from mice are collected to assess the cytokine levels using Luminex screening assay technology (R&D Systems). Briefly, analyte-specific antibodies are pre-coated onto color-coded beads. Beads, standards, and samples are pipetted into wells and the immobilized antibodies bind the analytes of interest. After washing away any unbound substances, a biotinylated antibody cocktail specific to the analytes of interest is added to each well. Following a wash to remove any unbound biotinylated antibody, Streptavidin-Phycoerythrin conjugate (Streptavidin-PE), which binds to the biotinylated detection antibodies, is added to each well. A final wash removes unbound Streptavidin-PE and the beads are resuspended in buffer and read using a Luminex analyzer (R&D Systems). A first laser is bead-specific and determines which analyte is being detected. A second laser determines the magnitude of the PE-derived signal, which is in direct proportion to the amount of analyte bound.

Surrogate Assays for Purity

In exemplary aspects of the invention, it may be desirable to determine purity by use of a surrogate assay that is amenable to highly qualitative and/or quantitative detection of products and/or impurities. Accordingly, the invention contemplates determination of purity of an RNA composition, e.g., an IVT RNA, produced by a certain IVT method, by determining purity of a surrogate RNA (e.g., a model RNA) produced by identical conditions. In this manner, purity can be determined indirectly via highly qualitative and/or quantitative detection methods in a surrogate system, this purity determination correlating to purity of an IVT RNA produced in a production system. Furthermore, a reconstitution or surrogate type assay may be used to determine the amount and identity of contaminants in a given RNA preparation indirectly. It may be difficult in some instances to detect low levels of contaminants or contaminants having similar structural properties to the RNA transcripts. Reconstitution systems can be used to test biological activity such as immune stimulatory activity e.g. cytokine activity associated with contaminants by adding back the putative contaminants which are missing from the RNA preparations of the invention in comparison to biological activity by RNA compositions produced by the traditional IVT methods. The reconstitution of the pure RNA preparations of the invention with putative contaminants can demonstrate the lack of the contaminants in the pure RNA preparations.

Additionally, model RNAs (surrogate mRNAs) may be used. Under the same IVT conditions used to produce the IVT RNA, a model RNA from a DNA template encoding the model RNA is produced. A model RNA or surrogate mRNA, as used herein, refers to a noncoding RNA transcript consisting of only the 5' UTR, 3' UTR, and polyA tail. A short model RNA may also be used. A short model RNA is a shorter version of model RNA (only consists of 5'UTR and a shorter polyA tail (A20)). The amount of reverse complement transcription product or cytokine-inducing species in the composition is determined by LC-MS or other analytical methods, as the amount of model RNA indicates the amount of reverse complement transcription product or cytokine-inducing species in the composition. The amount and nature of the contaminants detected in the assay correlates and predicts the amount and nature of the contaminants that would be obtained using the identical IVT reaction conditions to generate full-length mRNAs.

The RNA preparation of the invention is a high quality preparation. In some embodiments the RNA preparation resulting directly from an IVT process may be used directly as a research reagent or a diagnostic or therapeutic reagent without further purification. In some embodiments the RNA preparation may be subjected to one or more purification steps. For instance, the RNA preparation may be purified from truncated RNA, DNA template, and residual enzymes using oligo dT chromatography. An exemplary oligo dT chromatography assay involves packing 20 mer polythymidine Sepharose (3 ml) in a 5 mL SPE column on a solid phase extraction vacuum manifold. The RNA transcript is applied to column, followed by washing and elution. The oligo dT purified RNA transcript is diafiltered into water and concentrated to 1.22 mg/mL using 100 kDa MWCO Amicon spin filters (EMD Millipore). The RNA is recovered and the concentration may be determined using Bioanalyzer gel electrophoresis.

The analysis of the RNA preparation to determine purity and quality of the sample can be performed before or after capping. Alternatively, analysis can be performed before or after poly A capture based affinity purification. In another embodiment, analysis can be performed before or after optional additional purification steps, e.g., anion exchange chromatography and the like.

Mass spectrometry encompasses a broad range of techniques for identifying and characterizing compounds in mixtures. Different types of mass spectrometry-based approaches may be used to analyze a sample to determine its composition. Mass spectrometry analysis involves converting a sample being analyzed into multiple ions by an ionization process. Each of the resulting ions, when placed in a force field, moves in the field along a trajectory such that its acceleration is inversely proportional to its mass-to-charge ratio. A mass spectrum of a molecule is thus produced that displays a plot of relative abundances of precursor ions versus their mass-to-charge ratios. When a subsequent stage of mass spectrometry, such as tandem mass spectrometry, is used to further analyze the sample by subjecting precursor ions to higher energy, each precursor ion may undergo disassociation into fragments referred to as product ions. Resulting fragments can be used to provide information concerning the nature and the structure of their precursor molecule.

MALDI-TOF (matrix-assisted laser desorption ionization time of flight) mass spectrometry provides for the spectrometric determination of the mass of poorly ionizing or easily-fragmented analytes of low volatility by embedding them in a matrix of light-absorbing material and measuring the weight of the molecule as it is ionized and caused to fly by volatilization. Combinations of electric and magnetic fields are applied on the sample to cause the ionized material to move depending on the individual mass and charge of the molecule. U.S. Pat. No. 6,043,031, issued to Koster et al., describes an exemplary method for identifying single-base mutations within DNA using MALDI-TOF and other methods of mass spectrometry.

HPLC (high performance liquid chromatography) is used for the analytical separation of bio-polymers, based on properties of the bio-polymers. HPLC can be used to separate nucleic acid sequences based on size charge, and base composition. A nucleic acid sequence having one base pair difference from another nucleic acid can be separated using HPLC. Thus, nucleic acid samples, which are identical except for a single nucleotide may be differentially separated using HPLC, to identify the presence or absence of a particular nucleic acid fragments. Preferably the HPLC is HPLC-UV.

In some embodiments, the RNA may be purified without using a dsRNase step. For example, RNaseIII may not be used. The composition may be produced by a process that does not use reversed-phase chromatography purification step. In one embodiment, the RNA composition may be produced without using high-performance lipid chromatography (HPLC) purification. Thus, the composition is free of residual organic reagents or contaminants associated with traditional purification processes.

In some instances, the methods of the invention are used to determine the purity of an RNA sample. The term "pure" as used herein refers to material that has only the target nucleic acid active agents such that the presence of unrelated nucleic acids is reduced or eliminated, i.e., impurities or contaminants, including RNA fragments. For example, a purified RNA sample includes one or more target or test nucleic acids but is preferably substantially free of other nucleic acids detectable by methods described. As used herein, the term "substantially free" is used operationally, in the context of analytical testing of the material. Preferably, purified material is substantially free of one or more impurities or contaminants including the reverse complement transcription products and/or cytokine-inducing RNA contaminant described herein and for instance is at least 90%, 91%, 92%, 93%, 94%, 95%, 96%, or 97% pure; more preferably, at least 98% pure, and more preferably still at least 99% pure. In some embodiments a pure RNA sample is comprised of 100% of the target or test RNAs and includes no other RNA.

In some embodiments, capillary electrophoresis (CE) is used to separate the RNA. An electric field is applied to the sample so that it runs through an electrolyte solution, such as an aqueous buffer solution, to a destination vial via a capillary. The analytes migrate differently based on electrophoretic mobility and are detected at the outlet end of the capillary. The output data is recorded and then displayed as an electropherogram. It can be used in conjunction with mass spectrometry to determine the identity of sample components. The capillary electrophoresis system is fully automated in the FRAGMENT ANALYZER™, which can detect differences as small as three base pairs.

In some embodiments, a fragment analyzer (FA) may be used to quantify and purify the RNA. The fragment analyzer automates capillary electrophoresis and HPLC.

In some embodiments, the RNA molecules are mRNA molecules. As used herein, the term "messenger RNA" (mRNA) refers to any polynucleotide which encodes at least one peptide or polypeptide of interest and which is capable of being translated to produce the encoded peptide polypeptide of interest in vitro, in vivo, in situ or ex vivo. An mRNA has been transcribed from a DNA sequence by an RNA polymerase enzyme, and interacts with a ribosome synthesize genetic information encoded by DNA. Generally, mRNA is classified into two sub-classes: pre-mRNA and mature mRNA. Precursor mRNA (pre-mRNA) is mRNA that has been transcribed by RNA polymerase but has not undergone any post-transcriptional processing (e.g., 5' capping, splicing, editing, and polyadenylation). Mature mRNA has been modified via post-transcriptional processing (e.g., spliced to remove introns and polyadenylated) and is capable of interacting with ribosomes to perform protein synthesis. mRNA can be isolated from tissues or cells by a variety of methods. For example, a total RNA extraction can be performed on cells or a cell lysate and the resulting extracted total RNA can be purified (e.g., on a column comprising oligo-dT beads) to obtain extracted mRNA.

Alternatively, mRNA can be synthesized in a cell-free environment, for example by in vitro transcription (IVT). An "in vitro transcription template" as used herein, refers to deoxyribonucleic acid (DNA) suitable for use in an IVT reaction for the production of messenger RNA (mRNA). In some embodiments, an IVT template encodes a 5' untranslated region, contains an open reading frame, and encodes a 3' untranslated region and a polyA tail. The particular nucleotide sequence composition and length of an IVT template will depend on the mRNA of interest encoded by the template.

A "5' untranslated region (UTR)" refers to a region of an mRNA that is directly upstream (i.e., 5') from the start codon (i.e., the first codon of an mRNA transcript translated by a ribosome) that does not encode a protein or peptide.

A "3' untranslated region (UTR)" refers to a region of an mRNA that is directly downstream (i.e., 3') from the stop codon (i.e., the codon of an mRNA transcript that signals a termination of translation) that does not encode a protein or peptide.

An "open reading frame" is a continuous stretch of DNA beginning with a start codon (e.g., methionine (ATG)), and ending with a stop codon (e.g., TAA, TAG or TGA) and encodes a protein or peptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 350, 400, 450, 500, 550, or 600 adenosine monophosphates. In some embodiments, a polyA tail contains 50 to 250 adenosine monophosphates. In a relevant biological setting (e.g., in cells, in vivo, etc.) the poly(A) tail functions to protect mRNA from enzymatic degradation, e.g., in the cytoplasm, and aids in transcription termination, export of the mRNA from the nucleus, and translation.

Thus, the polynucleotide may in some embodiments comprise (a) a first region of linked nucleotides encoding a polypeptide of interest; (b) a first terminal region located 5' relative to said first region comprising a 5' untranslated region (UTR); (c) a second terminal region located 3' relative to said first region; and (d) a tailing region. The terms poly nucleotide and nucleic acid are used interchangeably herein.

In some embodiments, the polynucleotide includes from about 1 to about 3,000, 10 to about 3,000, 20 to about 3,000, 30 to about 3,000, 40 to about 3,000, 50 to about 3,000, 100 to about 3,000, 200 to about 3,000 nucleotides (e.g., from 200 to 500, from 200 to 1,000, from 200 to 1,500, from 200 to 3,000, from 500 to 1,000, from 500 to 1,500, from 500 to 2,000, from 500 to 3,000, from 1,000 to 1,500, from 1,000 to 2,000, from 1,000 to 3,000, from 1,500 to 3,000, and from 2,000 to 3,000).

IVT RNA may function as RNA but are distinguished from wild-type RNA in their functional and/or structural design features which serve to overcome existing problems of effective polypeptide production using nucleic-acid based therapeutics. For example, IVT RNA may be structurally modified or chemically modified. As used herein, a "structural" modification is one in which two or more linked nucleotides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" may be chemically modified to "AT-5meC-G". The same polynucleotide may be structurally modified from "ATCG" to "ATCCCG". Here, the dinucleotide "CC" has been inserted, resulting in a structural modification to the polynucleotide.

cDNA encoding the polynucleotides described herein may be transcribed using an in vitro transcription (IVT) system. The system typically comprises a transcription buffer, nucleotide triphosphates (NTPs), an RNase inhibitor and a polymerase. The NTPs may be manufactured in house, may be selected from a supplier, or may be synthesized as described herein. The NTPs may be selected from, but are not limited to, those described herein including natural and unnatural (modified) NTPs. The polymerase may be selected from, but is not limited to, T7 RNA polymerase, T3 RNA polymerase and mutant polymerases such as, but not limited to, polymerases able to incorporate polynucleotides (e.g., modified nucleic acids).

Chemically-Modified RNAs

Thus, in an exemplary aspect, polynucleotides of the invention may include at least one chemical modification. The polynucleotides can include various substitutions and/or insertions from native or naturally occurring polynucleotides. As used herein in a polynucleotide, the terms "chemical modification" or, as appropriate, "chemically modified" refer to modification with respect to adenosine (A), guanosine (G), uridine (U), thymidine (T) or cytidine (C) ribo- or deoxyribonucleosides in one or more of their position, pattern, percent or population. Generally, herein, these terms are not intended to refer to the ribonucleotide modifications in naturally occurring 5'-terminal RNA cap moieties.

The modifications may be various distinct modifications. In some embodiments, the regions may contain one, two, or more (optionally different) nucleoside or nucleotide modifications. In some embodiments, a modified polynucleotide, introduced to a cell may exhibit reduced degradation in the cell, as compared to an unmodified polynucleotide.

Modifications of the polynucleotides include, but are not limited to those listed in detail below. The polynucleotide may comprise modifications which are naturally occurring, non-naturally occurring or the polynucleotide can comprise both naturally and non-naturally occurring modifications.

The polynucleotides of the invention can include any useful modification, such as to the sugar, the nucleobase, or the internucleotide linkage (e.g. to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleotide linkage. Modifications according to the present invention may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

Non-natural modified nucleotides may be introduced to polynucleotides during synthesis or post-synthesis of the chains to achieve desired functions or properties. The modifications may be on internucleotide lineage, the purine or pyrimidine bases, or sugar. The modification may be introduced at the terminal of a chain or anywhere else in the chain; with chemical synthesis or with a polymerase enzyme. Any of the regions of the polynucleotides may be chemically modified.

The present disclosure provides for polynucleotides comprised of unmodified or modified nucleosides and nucleotides and combinations thereof. As described herein "nucleoside" is defined as a compound containing a sugar molecule (e.g., a pentose or ribose) or a derivative thereof in combination with an organic base (e.g., a purine or pyrimidine) or a derivative thereof (also referred to herein as "nucleobase"). As described herein, "nucleotide" is defined as a nucleoside including a phosphate group. The modified nucleotides may by synthesized by any useful method, as described herein (e.g., chemically, enzymatically, or recombinantly to include one or more modified or non-natural nucleotides). The polynucleotides may comprise a region or regions of linked nucleotides. Such regions may have variable backbone linkages. The linkages may be standard phosphodiester linkages, in which case the polynucleotides would comprise regions of nucleotides. Any combination of base/sugar or linker may be incorporated into the polynucleotides of the invention.

In some embodiments, an RNA of the invention includes a combination of one or more of the aforementioned modified nucleobases (e.g., a combination of 2, 3 or 4 of the aforementioned modified nucleobases.)

Modifications of the nucleic acids which are useful in the present invention include, but are not limited to those in the Table below.

| Name | Symbol | Base | Naturally Occurring |
|---|---|---|---|
| 2-methylthio-N6-(cis-hydroxyisopentenyl)adenosine | ms2i6A | A | YES |
| 2-methylthio-N6-methyladenosine | ms2m6A | A | YES |
| 2-methylthio-N6-threonyl carbamoyladenosine | ms2t6A | A | YES |
| N6-glycinylcarbamoyladenosine | g6A | A | YES |
| N6-isopentenyladenosine | i6A | A | YES |
| N6-methyladenosine | m6A | A | YES |
| N6-threonylcarbamoyladenosine | t6A | A | YES |
| 1,2'-O-dimethyladenosine | m1Am | A | YES |
| 1-methyladenosine | m1A | A | YES |
| 2'-O-methyladenosine | Am | A | YES |
| 2'-O-ribosyladenosine (phosphate) | Ar(p) | A | YES |
| 2-methyladenosine | m2A | A | YES |
| 2-methylthio-N6 isopentenyladenosine | ms2i6A | A | YES |
| 2-methylthio-N6-hydroxynorvalyl carbamoyladenosine | ms2hn6A | A | YES |
| 2'-O-methyladenosine | m6A | A | YES |
| 2'-O-ribosyladenosine (phosphate) | Ar(p) | A | YES |
| Isopentenyladenosine | Iga | A | YES |
| N6-(cis-hydroxyisopentenyl)adenosine | io6A | A | YES |
| N6,2'-O-dimethyladenosine | m6Am | A | YES |
| N6,2'-O-dimethyladenosine | m6Am | A | YES |
| N6,N6,2'-O-trimethyladenosine | m62Am | A | YES |
| N6,N6-dimethyladenosine | m62A | A | YES |
| N6-acetyladenosine | ac6A | A | YES |
| N6-hydroxynorvalylcarbamoyladenosine | hn6A | A | YES |
| N6-methyl-N6-threonylcarbamoyladenosine | m6t6A | A | YES |
| 2-methyladenosine | m2A | A | YES |
| 2-methylthio-N6-isopentenyladenosine | ms2i6A | A | YES |
| 7-deaza-adenosine | — | A | NO |
| N1-methyl-adenosine | — | A | NO |
| N6,N6 (dimethyl)adenine | — | A | NO |
| N6-cis-hydroxy-isopentenyl-adenosine | — | A | NO |
| α-thio-adenosine | — | A | NO |
| 2 (amino)adenine | — | A | NO |
| 2 (aminopropyl)adenine | — | A | NO |
| 2 (methylthio) N6 (isopentenyl)adenine | — | A | NO |
| 2-(alkyl)adenine | — | A | NO |
| 2-(aminoalkyl)adenine | — | A | NO |
| 2-(aminopropyl)adenine | — | A | NO |
| 2-(halo)adenine | — | A | NO |
| 2-(halo)adenine | — | A | NO |
| 2-(propyl)adenine | — | A | NO |
| 2'-Amino-2'-deoxy-ATP | — | A | NO |
| 2'-Azido-2'-deoxy-ATP | — | A | NO |
| 2'-Deoxy-2'-a-aminoadenosine TP | — | A | NO |
| 2'-Deoxy-2'-a-azidoadenosine TP | — | A | NO |
| 6 (alkyl)adenine | — | A | NO |
| 6 (methyl)adenine | — | A | NO |
| 6-(alkyl)adenine | — | A | NO |
| 6-(methyl)adenine | — | A | NO |
| 7 (deaza)adenine | — | A | NO |
| 8 (alkenyl)adenine | — | A | NO |
| 8 (alkynyl)adenine | — | A | NO |
| 8 (amino)adenine | — | A | NO |
| 8 (thioalkyl)adenine | — | A | NO |
| 8-(alkenyl)adenine | — | A | NO |
| 8-(alkyl)adenine | — | A | NO |
| 8-(alkynyl)adenine | — | A | NO |
| 8-(amino)adenine | — | A | NO |
| 8-(halo)adenine | — | A | NO |
| 8-(hydroxyl)adenine | — | A | NO |
| 8-(thioalkyl)adenine | — | A | NO |
| 8-(thiol)adenine | — | A | NO |
| 8-azido-adenosine | — | A | NO |
| aza adenine | — | A | NO |
| deaza adenine | — | A | NO |
| N6 (methyl)adenine | — | A | NO |
| N6-(isopentyl)adenine | — | A | NO |
| 7-deaza-8-aza-adenosine | — | A | NO |
| 7-methyladenine | — | A | NO |
| 1-Deazaadenosine TP | — | A | NO |
| 2'Fluoro-N6-Bz-deoxyadenosine TP | — | A | NO |
| 2'-OMe-2-Amino-ATP | — | A | NO |

-continued

| Name | Symbol | Base | Naturally Occurring |
|---|---|---|---|
| 2'O-methyl-N6-Bz-deoxyadenosine TP | — | A | NO |
| 2'-a-Ethynyladenosine TP | — | A | NO |
| 2-aminoadenine | — | A | NO |
| 2-Aminoadenosine TP | — | A | NO |
| 2-Amino-ATP | — | A | NO |
| 2'-a-Trifluoromethyladenosine TP | — | A | NO |
| 2-Azidoadenosine TP | — | A | NO |
| 2'-b-Ethynyladenosine TP | — | A | NO |
| 2-Bromoadenosine TP | — | A | NO |
| 2'-b-Trifluoromethyladenosine TP | — | A | NO |
| 2-Chloroadenosine TP | — | A | NO |
| 2'-Deoxy-2',2'-difluoroadenosine TP | — | A | NO |
| 2'-Deoxy-2'-a-mercaptoadenosine TP | — | A | NO |
| 2'-Deoxy-2'-a-thiomethoxyadenosine TP | — | A | NO |
| 2'-Deoxy-2'-b-aminoadenosine TP | — | A | NO |
| 2'-Deoxy-2'-b-azidoadenosine TP | — | A | NO |
| 2'-Deoxy-2'-b-bromoadenosine TP | — | A | NO |
| 2'-Deoxy-2'-b-chloroadenosine TP | — | A | NO |
| 2'-Deoxy-2'-b-fluoroadenosine TP | — | A | NO |
| 2'-Deoxy-2'-b-iodoadenosine TP | — | A | NO |
| 2'-Deoxy-2'-b-mercaptoadenosine TP | — | A | NO |
| 2'-Deoxy-2'-b-thiomethoxyadenosine TP | — | A | NO |
| 2-Fluoroadenosine TP | — | A | NO |
| 2-Iodoadenosine TP | — | A | NO |
| 2-Mercaptoadenosine TP | — | A | NO |
| 2-methoxy-adenine | — | A | NO |
| 2-methylthio-adenine | — | A | NO |
| 2-Trifluoromethyladenosine TP | — | A | NO |
| 3-Deaza-3-bromoadenosine TP | — | A | NO |
| 3-Deaza-3-chloroadenosine TP | — | A | NO |
| 3-Deaza-3-fluoroadenosine TP | — | A | NO |
| 3-Deaza-3-iodoadenosine TP | — | A | NO |
| 3-Deazaadenosine TP | — | A | NO |
| 4'-Azidoadenosine TP | — | A | NO |
| 4'-Carbocyclic adenosine TP | — | A | NO |
| 4'-Ethynyladenosine TP | — | A | NO |
| 5'-Homo-adenosine TP | — | A | NO |
| 8-Aza-ATP | — | A | NO |
| 8-bromo-adenosine TP | — | A | NO |
| 8-Trifluoromethyladenosine TP | — | A | NO |
| 9-Deazaadenosine TP | — | A | NO |
| 2-aminopurine | — | A/G | NO |
| 7-deaza-2,6-diaminopurine | — | A/G | NO |
| 7-deaza-8-aza-2,6-diaminopurine | — | A/G | NO |
| 7-deaza-8-aza-2-aminopurine | — | A/G | NO |
| 2,6-diaminopurine | — | A/G | NO |
| 7-deaza-8-aza-adenine, 7-deaza-2-aminopurine | — | A/G | NO |
| 2-thiocytidine | s2C | C | YES |
| 3-methylcytidine | m3C | C | YES |
| 5-formylcytidine | f5C | C | YES |
| 5-hydroxymethylcytidine | hm5C | C | YES |
| 5-methylcytidine | m5C | C | YES |
| N4-acetylcytidine | ac4C | C | YES |
| 2'-O-methylcytidine | Cm | C | YES |
| 2'-O-methylcytidine | Cm | C | YES |
| 5,2'-O-dimethylcytidine | m5Cm | C | YES |
| 5-formyl-2'-O-methylcytidine | f5Cm | C | YES |
| Lysidine | k2C | C | YES |
| N4,2'-O-dimethylcytidine | m4Cm | C | YES |
| N4-acetyl-2'-O-methylcytidine | ac4Cm | C | YES |
| N4-methylcytidine | m4C | C | YES |
| N4,N4-Dimethyl-2'-OMe-Cytidine TP | — | C | YES |
| 4-methylcytidine | — | C | NO |
| 5-aza-cytidine | — | C | NO |
| Pseudo-iso-cytidine | — | C | NO |
| pyrrolo-cytidine | — | C | NO |
| α-thio-cytidine | — | C | NO |
| 2-(thio)cytosine | — | C | NO |
| 2'-Amino-2'-deoxy-CTP | — | C | NO |
| 2'-Azido-2'-deoxy-CTP | — | C | NO |
| 2'-Deoxy-2'-a-aminocytidine TP | — | C | NO |
| 2'-Deoxy-2'-a-azidocytidine TP | — | C | NO |

-continued

| Name | Symbol | Base | Naturally Occurring |
|---|---|---|---|
| 3 (deaza) 5 (aza)cytosine | — | C | NO |
| 3 (methyl)cytosine | — | C | NO |
| 3-(alkyl)cytosine | — | C | NO |
| 3-(deaza) 5 (aza)cytosine | — | C | NO |
| 3-(methyl)cytidine | — | C | NO |
| 4,2'-O-dimethylcytidine | — | C | NO |
| 5 (halo)cytosine | — | C | NO |
| 5 (methyl)cytosine | — | C | NO |
| 5 (propynyl)cytosine | — | C | NO |
| 5 (trifluoromethyl)cytosine | — | C | NO |
| 5-(alkyl)cytosine | — | C | NO |
| 5-(alkynyl)cytosine | — | C | NO |
| 5-(halo)cytosine | — | C | NO |
| 5-(propynyl)cytosine | — | C | NO |
| 5-(trifluoromethyl)cytosine | — | C | NO |
| 5-bromo-cytidine | — | C | NO |
| 5-iodo-cytidine | — | C | NO |
| 5-propynyl cytosine | — | C | NO |
| 6-(azo)cytosine | — | C | NO |
| 6-aza-cytidine | — | C | NO |
| aza cytosine | — | C | NO |
| deaza cytosine | — | C | NO |
| N4 (acetyl)cytosine | — | C | NO |
| 1-methyl-1-deaza-pseudoisocytidine | — | C | NO |
| 1-methyl-pseudoisocytidine | — | C | NO |
| 2-methoxy-5-methyl-cytidine | — | C | NO |
| 2-methoxy-cytidine | — | C | NO |
| 2-thio-5-methyl-cytidine | — | C | NO |
| 4-methoxy-1-methyl-pseudoisocytidine | — | C | NO |
| 4-methoxy-pseudoisocytidine | — | C | NO |
| 4-thio-1-methyl-1-deaza-pseudoisocytidine | — | C | NO |
| 4-thio-1-methyl-pseudoisocytidine | — | C | NO |
| 4-thio-pseudoisocytidine | — | C | NO |
| 5-aza-zebularine | — | C | NO |
| 5-methyl-zebularine | — | C | NO |
| pyrrolo-pseudoisocytidine | — | C | NO |
| Zebularine | — | C | NO |
| (E)-5-(2-Bromo-vinyl)cytidine TP | — | C | NO |
| 2,2'-anhydro-cytidine TP hydrochloride | — | C | NO |
| 2'Fluor-N4-Bz-cytidine TP | — | C | NO |
| 2'Fluoro-N4-Acetyl-cytidine TP | — | C | NO |
| 2'-O-Methyl-N4-Acetyl-cytidine TP | — | C | NO |
| 2'O-methyl-N4-Bz-cytidine TP | — | C | NO |
| 2'-a-Ethynylcytidine TP | — | C | NO |
| 2'-a-Trifluoromethylcytidine TP | — | C | NO |
| 2'-b-Ethynylcytidine TP | — | C | NO |
| 2'-b-Trifluoromethylcytidine TP | — | C | NO |
| 2'-Deoxy-2',2'-difluorocytidine TP | — | C | NO |
| 2'-Deoxy-2'-a-mercaptocytidine TP | — | C | NO |
| 2'-Deoxy-2'-a-thiomethoxycytidine TP | — | C | NO |
| 2'-Deoxy-2'-b-aminocytidine TP | — | C | NO |
| 2'-Deoxy-2'-b-azidocytidine TP | — | C | NO |
| 2'-Deoxy-2'-b-bromocytidine TP | — | C | NO |
| 2'-Deoxy-2'-b-chlorocytidine TP | — | C | NO |
| 2'-Deoxy-2'-b-fluorocytidine TP | — | C | NO |
| 2'-Deoxy-2'-b-iodocytidine TP | — | C | NO |
| 2'-Deoxy-2'-b-mercaptocytidine TP | — | C | NO |
| 2'-Deoxy-2'-b-thiomethoxycytidine TP | — | C | NO |
| 2'-O-Methyl-5-(1-propynyl)cytidine TP | — | C | NO |
| 3'-Ethynylcytidine TP | — | C | NO |
| 4'-Azidocytidine TP | — | C | NO |
| 4'-Carbocyclic cytidine TP | — | C | NO |
| 4'-Ethynylcytidine TP | — | C | NO |
| 5-(1-Propynyl)ara-cytidine TP | — | C | NO |
| 5-(2-Chloro-phenyl)-2-thiocytidine TP | — | C | NO |
| 5-(4-Amino-phenyl)-2-thiocytidine TP | — | C | NO |
| 5-Aminoallyl-CTP | — | C | NO |
| 5-Cyanocytidine TP | — | C | NO |
| 5-Ethynylara-cytidine TP | — | C | NO |
| 5-Ethynylcytidine TP | — | C | NO |
| 5'-Homo-cytidine TP | — | C | NO |
| 5-Methoxycytidine TP | — | C | NO |

| Name | Symbol | Base | Naturally Occurring |
|---|---|---|---|
| 5-Trifluoromethyl-Cytidine TP | — | C | NO |
| N4-Amino-cytidine TP | — | C | NO |
| N4-Benzoyl-cytidine TP | — | C | NO |
| Pseudoisocytidine | — | C | NO |
| 7-methylguanosine | m7G | G | YES |
| N2,2'-O-dimethylguanosine | m2Gm | G | YES |
| N2-methylguanosine | m2G | G | YES |
| Wyosine | imG | G | YES |
| 1,2'-O-dimethylguanosine | m1Gm | G | YES |
| 1-methylguanosine | m1G | G | YES |
| 2'-O-methylguanosine | Gm | G | YES |
| 2'-O-ribosylguanosine (phosphate) | Gr(p) | G | YES |
| 2'-O-methylguanosine | Gm | G | YES |
| 2'-O-ribosylguanosine (phosphate) | Gr(p) | G | YES |
| 7-aminomethyl-7-deazaguanosine | preQ1 | G | YES |
| 7-cyano-7-deazaguanosine | preQ0 | G | YES |
| Archaeosine | G+ | G | YES |
| Methylwyosine | mimG | G | YES |
| N2,7-dimethylguanosine | m2,7G | G | YES |
| N2,N2,2'-O-trimethylguanosine | m22Gm | G | YES |
| N2,N2,7-trimethylguanosine | m2,2,7G | G | YES |
| N2,N2-dimethylguanosine | m22G | G | YES |
| N2,7,2'-O-trimethylguanosine | m2,7Gm | G | YES |
| 6-thio-guanosine | — | G | NO |
| 7-deaza-guanosine | — | G | NO |
| 8-oxo-guanosine | — | G | NO |
| N1-methyl-guanosine | — | G | NO |
| α-thio-guanosine | — | G | NO |
| 2 (propyl)guanine | — | G | NO |
| 2-(alkyl)guanine | — | G | NO |
| 2'-Amino-2'-deoxy-GTP | — | G | NO |
| 2'-Azido-2'-deoxy-GTP | — | G | NO |
| 2'-Deoxy-2'-a-aminoguanosine TP | — | G | NO |
| 2'-Deoxy-2'-a-azidoguanosine TP | — | G | NO |
| 6 (methyl)guanine | — | G | NO |
| 6-(alkyl)guanine | — | G | NO |
| 6-(methyl)guanine | — | G | NO |
| 6-methyl-guanosine | — | G | NO |
| 7 (alkyl)guanine | — | G | NO |
| 7 (deaza)guanine | — | G | NO |
| 7 (methyl)guanine | — | G | NO |
| 7-(alkyl)guanine | — | G | NO |
| 7-(deaza)guanine | — | G | NO |
| 7-(methyl)guanine | — | G | NO |
| 8 (alkyl)guanine | — | G | NO |
| 8 (alkynyl)guanine | — | G | NO |
| 8 (halo)guanine | — | G | NO |
| 8 (thioalkyl)guanine | — | G | NO |
| 8-(alkenyl)guanine | — | G | NO |
| 8-(alkyl)guanine | — | G | NO |
| 8-(alkynyl)guanine | — | G | NO |
| 8-(amino)guanine | — | G | NO |
| 8-(halo)guanine | — | G | NO |
| 8-(hydroxyl)guanine | — | G | NO |
| 8-(thioalkyl)guanine | — | G | NO |
| 8-(thiol)guanine | — | G | NO |
| aza guanine | — | G | NO |
| deaza guanine | — | G | NO |
| N (methyl)guanine | — | G | NO |
| N-(methyl)guanine | — | G | NO |
| 1-methyl-6-thio-guanosine | — | G | NO |
| 6-methoxy-guanosine | — | G | NO |
| 6-thio-7-deaza-8-aza-guanosine | — | G | NO |
| 6-thio-7-deaza-guanosine | — | G | NO |
| 6-thio-7-methyl-guanosine | — | G | NO |
| 7-deaza-8-aza-guanosine | — | G | NO |
| 7-methyl-8-oxo-guanosine | — | G | NO |
| N2,N2-dimethyl-6-thio-guanosine | — | G | NO |
| N2-methyl-6-thio-guanosine | — | G | NO |
| 1-Me-GTP | — | G | NO |
| 2'Fluoro-N2-isobutyl-guanosine TP | — | G | NO |
| 2'O-methyl-N2-isobutyl-guanosine TP | — | G | NO |
| 2'-a-Ethynylguanosine TP | — | G | NO |
| 2'-a-Trifluoromethylguanosine TP | — | G | NO |
| 2'-b-Ethynylguanosine TP | — | G | NO |
| 2'-b-Trifluoromethylguanosine TP | — | G | NO |
| 2'-Deoxy-2',2'-difluoroguanosine TP | — | G | NO |
| 2'-Deoxy-2'-a-mercaptoguanosine TP | — | G | NO |
| 2'-Deoxy-2'-a-thiomethoxyguanosine TP | — | G | NO |
| 2'-Deoxy-2'-b-aminoguanosine TP | — | G | NO |
| 2'-Deoxy-2'-b-azidoguanosine TP | — | G | NO |
| 2'-Deoxy-2'-b-bromoguanosine TP | — | G | NO |
| 2'-Deoxy-2'-b-chloroguanosine TP | — | G | NO |
| 2'-Deoxy-2'-b-fluoroguanosine TP | — | G | NO |
| 2'-Deoxy-2'-b-iodoguanosine TP | — | G | NO |
| 2'-Deoxy-2'-b-mercaptoguanosine TP | — | G | NO |
| 2'-Deoxy-2'-b-thiomethoxyguanosine TP | — | G | NO |
| 4'-Azidoguanosine TP | — | G | NO |
| 4'-Carbocyclic guanosine TP | — | G | NO |
| 4'-Ethynylguanosine TP | — | G | NO |
| 5'-Homo-guanosine TP | — | G | NO |
| 8-bromo-guanosine TP | — | G | NO |
| 9-Deazaguanosine TP | — | G | NO |
| N2-isobutyl-guanosine TP | — | G | NO |
| 1-methylinosine | m1I | I | YES |
| Inosine | I | I | YES |
| 1,2'-O-dimethylinosine | m1Im | I | YES |
| 2'-O-methylinosine | Im | I | YES |
| 7-methylinosine | — | I | NO |
| 2'-O-methylinosine | Im | I | YES |
| Epoxyqueuosine | oQ | Q | YES |
| galactosyl-queuosine | galQ | Q | YES |
| Mannosylqueuosine | manQ | Q | YES |
| Queuosine | Q | Q | YES |
| allyamino-thymidine | — | T | NO |
| aza thymidine | — | T | NO |
| deaza thymidine | — | T | NO |
| deoxy-thymidine | — | T | NO |
| 2'-O-methyluridine | — | U | YES |
| 2-thiouridine | s2U | U | YES |
| 3-methyluridine | m3U | U | YES |
| 5-carboxymethyluridine | cm5U | U | YES |
| 5-hydroxyuridine | ho5U | U | YES |
| 5-methyluridine | m5U | U | YES |
| 5-taurinomethyl-2-thiouridine | τm5s2U | U | YES |
| 5-taurinomethyluridine | τm5U | U | YES |
| Dihydrouridine | D | U | YES |
| Pseudouridine | Ψ | U | YES |
| (3-(3-amino-3-carboxypropyl)uridine | acp3U | U | YES |
| 1-methyl-3-(3-amino-5-carboxypropyl)pseudouridine | m1acp3Ψ | U | YES |
| 1-methylpseduouridine | m1Ψ | U | YES |
| 1-methyl-pseudouridine | — | U | YES |
| 2'-O-methyluridine | Um | U | YES |
| 2'-O-methylpseudouridine | Ψm | U | YES |
| 2'-O-methyluridine | Um | U | YES |
| 2-thio-2'-O-methyluridine | s2Um | U | YES |
| 3-(3-amino-3-carboxypropyl)uridine | acp3U | U | YES |
| 3,2'-O-dimethyluridine | m3Um | U | YES |
| 3-Methyl-pseudo-Uridine TP | — | U | YES |
| 4-thiouridine | s4U | U | YES |
| 5-(carboxyhydroxymethyl)uridine | chm5U | U | YES |
| 5-(carboxyhydroxymethyl)uridine methyl ester | mchm5U | U | YES |
| 5,2'-O-dimethyluridine | m5Um | U | YES |
| 5,6-dihydro-uridine | — | U | YES |
| 5-aminomethyl-2-thiouridine | nm5s2U | U | YES |
| 5-carbamoylmethyl-2'-O-methyluridine | ncm5Um | U | YES |
| 5-carbamoylmethyluridine | ncm5U | U | YES |
| 5-carboxyhydroxymethyluridine | — | U | YES |
| 5-carboxyhydroxymethyluridine methyl ester | — | U | YES |
| 5-carboxymethylaminomethyl-2'-O-methyluridine | cmnm5Um | U | YES |
| 5-carboxymethylaminomethyl-2-thiouridine | cmnm5s2U | U | YES |
| 5-carboxymethylaminomethyl-2-thiouridine | — | U | YES |
| 5-carboxymethylaminomethyluridine | cmnm5U | U | YES |

| Name | Symbol | Base | Naturally Occurring |
|---|---|---|---|
| 5-carboxymethylaminomethyluridine | — | U | YES |
| 5-Carbamoylmethyluridine TP | — | U | YES |
| 5-methoxycarbonylmethyl-2'-O-methyluridine | mcm5Um | U | YES |
| 5-methoxycarbonylmethyl-2-thiouridine | mcm5s2U | U | YES |
| 5-methoxycarbonylmethyluridine | mcm5U | U | YES |
| 5-methoxyuridine | mo5U | U | YES |
| 5-methyl-2-thiouridine | m5s2U | U | YES |
| 5-methylaminomethyl-2-selenouridine | mnm5se2U | U | YES |
| 5-methylaminomethyl-2-thiouridine | mnm5s2U | U | YES |
| 5-methylaminomethyluridine | mnm5U | U | YES |
| 5-Methyldihydrouridine | — | U | YES |
| 5-Oxyacetic acid-Uridine TP | — | U | YES |
| 5-Oxyacetic acid-methyl ester-Uridine TP | — | U | YES |
| N1-methyl-pseudo-uridine | — | U | YES |
| uridine 5-oxyacetic acid | cmo5U | U | YES |
| uridine 5-oxyacetic acid methyl ester | mcmo5U | U | YES |
| 3-(3-Amino-3-carboxypropyl)-Uridine TP | — | U | YES |
| 5-(iso-Pentenylaminomethyl)-2-thiouridine TP | — | U | YES |
| 5-(iso-Pentenylaminomethyl)-2'-O-methyluridine TP | — | U | YES |
| 5-(iso-Pentenylaminomethyl)uridine TP | — | U | YES |
| 5-propynyl uracil | — | U | NO |
| α-thio-uridine | — | U | NO |
| 1 (aminoalkylamino-carbonylethylenyl)-2(thio)-pseudouracil | — | U | NO |
| 1 (aminoalkylaminocarbonylethylenyl)-2,4-(dithio)pseudouracil | — | U | NO |
| 1 (aminoalkylaminocarbonylethylenyl)-4 (thio)pseudouracil | — | U | NO |
| 1 (aminoalkylaminocarbonylethylenyl)-pseudouracil | — | U | NO |
| 1 (aminocarbonylethylenyl)-2(thio)-pseudouracil | — | U | NO |
| 1 (aminocarbonylethylenyl)-2,4-(dithio)pseudouracil | — | U | NO |
| 1 (aminocarbonylethylenyl)-4 (thio)pseudouracil | — | U | NO |
| 1 (aminocarbonylethylenyl)-pseudouracil | — | U | NO |
| 1 substituted 2(thio)-pseudouracil | — | U | NO |
| 1 substituted 2,4-(dithio)pseudouracil | — | U | NO |
| 1 substituted 4 (thio)pseudouracil | — | U | NO |
| 1 substituted pseudouracil | — | U | NO |
| 1-(aminoalkylamino-carbonylethylenyl)-2-(thio)-pseudouracil | — | U | NO |
| 1-Methyl-3-(3-amino-3-carboxypropyl) pseudouridine TP | — | U | NO |
| 1-Methyl-3-(3-amino-3-carboxypropyl)pseudo-UTP | — | U | NO |
| 1-Methyl-pseudo-UTP | — | U | NO |
| 2 (thio)pseudouracil | — | U | NO |
| 2' deoxy uridine | — | U | NO |
| 2' fluorouridine | — | U | NO |
| 2-(thio)uracil | — | U | NO |
| 2,4-(dithio)psuedouracil | — | U | NO |
| 2' methyl, 2'amino, 2'azido, 2'fluro-guanosine | — | U | NO |
| 2'-Amino-2'-deoxy-UTP | — | U | NO |
| 2'-Azido-2'-deoxy-UTP | — | U | NO |
| 2'-Azido-deoxyuridine TP | — | U | NO |
| 2'-O-methylpseudouridine | — | U | NO |
| 2' deoxy uridine | 2' dU | U | NO |
| 2' fluorouridine | — | U | NO |
| 2'-Deoxy-2'-a-aminouridine TP | — | U | NO |
| 2'-Deoxy-2'-a-azidouridine TP | — | U | NO |
| 2-methylpseudouridine | m3Ψ | U | NO |
| 3 (3 amino-3 carboxypropyl)uracil | — | U | NO |
| 4 (thio)pseudouracil | — | U | NO |
| 4-(thio)pseudouracil | — | U | NO |
| 4-(thio)uracil | — | U | NO |
| 4-thiouracil | — | U | NO |
| 5 (1,3-diazole-1-alkyl)uracil | — | U | NO |
| 5 (2-aminopropyl)uracil | — | U | NO |
| 5 (aminoalkyl)uracil | — | U | NO |
| 5 (dimethylaminoalkyl)uracil | — | U | NO |
| 5 (guanidiniumalkyl)uracil | — | U | NO |
| 5 (methoxycarbonylmethyl)-2-(thio)uracil | — | U | NO |
| 5 (methoxycarbonyl-methyl)uracil | — | U | NO |
| 5 (methyl) 2 (thio)uracil | — | U | NO |
| 5 (methyl) 2,4 (dithio)uracil | — | U | NO |
| 5 (methyl) 4 (thio)uracil | — | U | NO |
| 5 (methylaminomethyl)-2 (thio)uracil | — | U | NO |
| 5 (methylaminomethyl)-2,4 (dithio)uracil | — | U | NO |
| 5 (methylaminomethyl)-4 (thio)uracil | — | U | NO |
| 5 (propynyl)uracil | — | U | NO |
| 5 (trifluoromethyl)uracil | — | U | NO |
| 5-(2-aminopropyl)uracil | — | U | NO |
| 5-(alkyl)-2-(thio)pseudouracil | — | U | NO |
| 5-(alkyl)-2,4 (dithio)pseudouracil | — | U | NO |
| 5-(alkyl)-4 (thio)pseudouracil | — | U | NO |
| 5-(alkyl)pseudouracil | — | U | NO |
| 5-(alkyl)uracil | — | U | NO |
| 5-(alkynyl)uracil | — | U | NO |
| 5-(allylamino)uracil | — | U | NO |
| 5-(cyanoalkyl)uracil | — | U | NO |
| 5-(dialkylaminoalkyl)uracil | — | U | NO |
| 5-(dimethylaminoalkyl)uracil | — | U | NO |
| 5-(guanidiniumalkyl)uracil | — | U | NO |
| 5-(halo)uracil | — | U | NO |
| 5-(1,3-diazole-1-alkyl)uracil | — | U | NO |
| 5-(methoxy)uracil | — | U | NO |
| 5-(methoxycarbonylmethyl)-2-(thio)uracil | — | U | NO |
| 5-(methoxycarbonyl-methyl)uracil | — | U | NO |
| 5-(methyl) 2(thio)uracil | — | U | NO |
| 5-(methyl) 2,4 (dithio)uracil | — | U | NO |
| 5-(methyl) 4 (thio)uracil | — | U | NO |
| 5-(methyl)-2-(thio)pseudouracil | — | U | NO |
| 5-(methyl)-2,4 (dithio)pseudouracil | — | U | NO |
| 5-(methyl)-4 (thio)pseudouracil | — | U | NO |
| 5-(methyl)pseudouracil | — | U | NO |
| 5-(methylaminomethyl)-2 (thio)uracil | — | U | NO |
| 5-(methylaminomethyl)-2,4(dithio)uracil | — | U | NO |
| 5-(methylaminomethyl)-4-(thio)uracil | — | U | NO |
| 5-(propynyl)uracil | — | U | NO |
| 5-(trifluoromethyl)uracil | — | U | NO |
| 5-aminoallyl-uridine | — | U | NO |
| 5-bromo-uridine | — | U | NO |
| 5-iodo-uridine | — | U | NO |
| 5-uracil | — | U | NO |
| 6 (azo)uracil | — | U | NO |
| 6-(azo)uracil | — | U | NO |
| 6-aza-uridine | — | U | NO |
| allyamino-uracil | — | U | NO |
| aza uracil | — | U | NO |
| deaza uracil | — | U | NO |
| N3 (methyl)uracil | — | U | NO |
| Pseudo-UTP-1-2-ethanoic acid | — | U | NO |
| Pseudouracil | — | U | NO |
| 4-Thio-pseudo-UTP | — | U | NO |
| 1-carboxymethyl-pseudouridine | — | U | NO |
| 1-methyl-1-deaza-pseudouridine | — | U | NO |
| 1-propynyl-uridine | — | U | NO |
| 1-taurinomethyl-1-methyl-uridine | — | U | NO |
| 1-taurinomethyl-4-thio-uridine | — | U | NO |
| 1-taurinomethyl-pseudouridine | — | U | NO |
| 2-methoxy-4-thio-pseudouridine | — | U | NO |
| 2-thio-1-methyl-1-deaza-pseudouridine | — | U | NO |

| Name | Symbol | Base | Naturally Occurring |
|---|---|---|---|
| 2-thio-1-methyl-pseudouridine | — | U | NO |
| 2-thio-5-aza-uridine | — | U | NO |
| 2-thio-dihydropseudouridine | — | U | NO |
| 2-thio-dihydrouridine | — | U | NO |
| 2-thio-pseudouridine | — | U | NO |
| 4-methoxy-2-thio-pseudouridine | — | U | NO |
| 4-methoxy-pseudouridine | — | U | NO |
| 4-thio-1-methyl-pseudouridine | — | U | NO |
| 4-thio-pseudouridine | — | U | NO |
| 5-aza-uridine | — | U | NO |
| Dihydropseudouridine | — | U | NO |
| (±)1-(2-Hydroxypropyl)pseudouridine TP | — | U | NO |
| (2R)-1-(2-Hydroxypropyl)pseudouridine TP | — | U | NO |
| (2S)-1-(2-Hydroxypropyl)pseudouridine TP | — | U | NO |
| (E)-5-(2-Bromo-vinyl)ara-uridine TP | — | U | NO |
| (E)-5-(2-Bromo-vinyl)uridine TP | — | U | NO |
| (Z)-5-(2-Bromo-vinyl)ara-uridine TP | — | U | NO |
| (Z)-5-(2-Bromo-vinyl)uridine TP | — | U | NO |
| 1-(2,2,2-Trifluoroethyl)-pseudo-UTP | — | U | NO |
| 1-(2,2,3,3,3-Pentafluoropropyl)pseudouridine TP | — | U | NO |
| 1-(2,2-Diethoxyethyl)pseudouridine TP | — | U | NO |
| 1-(2,4,6-Trimethylbenzyl)pseudouridine TP | — | U | NO |
| 1-(2,4,6-Trimethyl-benzyl)pseudo-UTP | — | U | NO |
| 1-(2,4,6-Trimethyl-phenyl)pseudo-UTP | — | U | NO |
| 1-(2-Amino-2-carboxyethyl)pseudo-UTP | — | U | NO |
| 1-(2-Amino-ethyl)pseudo-UTP | — | U | NO |
| 1-(2-Hydroxyethyl)pseudouridine TP | — | U | NO |
| 1-(2-Methoxyethyl)pseudouridine TP | — | U | NO |
| 1-(3,4-Bis-trifluoromethoxybenzyl)pseudouridine TP | — | U | NO |
| 1-(3,4-Dimethoxybenzyl)pseudouridine TP | — | U | NO |
| 1-(3-Amino-3-carboxypropyl)pseudo-UTP | — | U | NO |
| 1-(3-Amino-propyl)pseudo-UTP | — | U | NO |
| 1-(3-Cyclopropyl-prop-2-ynyl)pseudouridine TP | — | U | NO |
| 1-(4-Amino-4-carboxybutyl)pseudo-UTP | — | U | NO |
| 1-(4-Amino-benzyl)pseudo-UTP | — | U | NO |
| 1-(4-Amino-butyl)pseudo-UTP | — | U | NO |
| 1-(4-Amino-phenyl)pseudo-UTP | — | U | NO |
| 1-(4-Azidobenzyl)pseudouridine TP | — | U | NO |
| 1-(4-Bromobenzyl)pseudouridine TP | — | U | NO |
| 1-(4-Chlorobenzyl)pseudouridine TP | — | U | NO |
| 1-(4-Fluorobenzyl)pseudouridine TP | — | U | NO |
| 1-(4-Iodobenzyl)pseudouridine TP | — | U | NO |
| 1-(4-Methanesulfonylbenzyl)pseudouridine TP | — | U | NO |
| 1-(4-Methoxybenzyl)pseudouridine TP | — | U | NO |
| 1-(4-Methoxy-benzyl)pseudo-UTP | — | U | NO |
| 1-(4-Methoxy-phenyl)pseudo-UTP | — | U | NO |
| 1-(4-Methylbenzyl)pseudouridine TP | — | U | NO |
| 1-(4-Methyl-benzyl)pseudo-UTP | — | U | NO |
| 1-(4-Nitrobenzyl)pseudouridine TP | — | U | NO |
| 1-(4-Nitro-benzyl)pseudo-UTP | — | U | NO |
| 1(4-Nitro-phenyl)pseudo-UTP | — | U | NO |
| 1-(4-Thiomethoxybenzyl)pseudouridine TP | — | U | NO |
| 1-(4-Trifluoromethoxybenzyl)pseudouridine TP | — | U | NO |
| 1-(4-Trifluoromethylbenzyl)pseudouridine TP | — | U | NO |
| 1-(5-Amino-pentyl)pseudo-UTP | — | U | NO |
| 1-(6-Amino-hexyl)pseudo-UTP | — | U | NO |
| 1,6-Dimethyl-pseudo-UTP | — | U | NO |
| 1-[3-(2-{2-[2-(2-Aminoethoxy)-ethoxy]-ethoxy}-ethoxy)-propionyl]pseudouridine TP | — | U | NO |
| 1-{3-[2-(2-Aminoethoxy)-ethoxy]-propionyl} pseudouridine TP | — | U | NO |
| 1-Acetylpseudouridine TP | — | U | NO |
| 1-Alkyl-6-(1-propynyl)-pseudo-UTP | — | U | NO |
| 1-Alkyl-6-(2-propynyl)-pseudo-UTP | — | U | NO |
| 1-Alkyl-6-allyl-pseudo-UTP | — | U | NO |
| 1-Alkyl-6-ethynyl-pseudo-UTP | — | U | NO |
| 1-Alkyl-6-homoallyl-pseudo-UTP | — | U | NO |
| 1-Alkyl-6-vinyl-pseudo-UTP | — | U | NO |
| 1-Allylpseudouridine TP | — | U | NO |
| 1-Aminomethyl-pseudo-UTP | — | U | NO |
| 1-Benzoylpseudouridine TP | — | U | NO |
| 1-Benzyloxymethylpseudouridine TP | — | U | NO |
| 1-Benzyl-pseudo-UTP | — | U | NO |
| 1-Biotinyl-PEG2-pseudouridine TP | — | U | NO |
| 1-Biotinylpseudouridine TP | — | U | NO |
| 1-Butyl-pseudo-UTP | — | U | NO |
| 1-Cyanomethylpseudouridine TP | — | U | NO |
| 1-Cyclobutylmethyl-pseudo-UTP | — | U | NO |
| 1-Cyclobutyl-pseudo-UTP | — | U | NO |
| 1-Cycloheptylmethyl-pseudo-UTP | — | U | NO |
| 1-Cycloheptyl-pseudo-UTP | — | U | NO |
| 1-Cyclohexylmethyl-pseudo-UTP | — | U | NO |
| 1-Cyclohexyl-pseudo-UTP | — | U | NO |
| 1-Cyclooctylmethyl-pseudo-UTP | — | U | NO |
| 1-Cyclooctyl-pseudo-UTP | — | U | NO |
| 1-Cyclopentylmethyl-pseudo-UTP | — | U | NO |
| 1-Cyclopentyl-pseudo-UTP | — | U | NO |
| 1-Cyclopropylmethyl-pseudo-UTP | — | U | NO |
| 1-Cyclopropyl-pseudo-UTP | — | U | NO |
| 1-Ethyl-pseudo-UTP | — | U | NO |
| 1-Hexyl-pseudo-UTP | — | U | NO |
| 1-Homoallylpseudouridine TP | — | U | NO |
| 1-Hydroxymethylpseudouridine TP | — | U | NO |
| 1-iso-propyl-pseudo-UTP | — | U | NO |
| 1-Me-2-thio-pseudo-UTP | — | U | NO |
| 1-Me-4-thio-pseudo-UTP | — | U | NO |
| 1-Me-alpha-thio-pseudo-UTP | — | U | NO |
| 1-Methanesulfonylmethylpseudouridine TP | — | U | NO |
| 1-Methoxymethylpseudouridine TP | — | U | NO |
| 1-Methyl-6-(2,2,2-Trifluoroethyl)pseudo-UTP | — | U | NO |
| 1-Methyl-6-(4-morpholino)-pseudo-UTP | — | U | NO |
| 1-Methyl-6-(4-thiomorpholino)-pseudo-UTP | — | U | NO |
| 1-Methyl-6-(substituted phenyl)pseudo-UTP | — | U | NO |
| 1-Methyl-6-amino-pseudo-UTP | — | U | NO |
| 1-Methyl-6-azido-pseudo-UTP | — | U | NO |
| 1-Methyl-6-bromo-pseudo-UTP | — | U | NO |
| 1-Methyl-6-butyl-pseudo-UTP | — | U | NO |
| 1-Methyl-6-chloro-pseudo-UTP | — | U | NO |
| 1-Methyl-6-cyano-pseudo-UTP | — | U | NO |
| 1-Methyl-6-dimethylamino-pseudo-UTP | — | U | NO |
| 1-Methyl-6-ethoxy-pseudo-UTP | — | U | NO |
| 1-Methyl-6-ethylcarboxylate-pseudo-UTP | — | U | NO |
| 1-Methyl-6-ethyl-pseudo-UTP | — | U | NO |
| 1-Methyl-6-fluoro-pseudo-UTP | — | U | NO |
| 1-Methyl-6-formyl-pseudo-UTP | — | U | NO |
| 1-Methyl-6-hydroxyamino-pseudo-UTP | — | U | NO |
| 1-Methyl-6-hydroxy-pseudo-UTP | — | U | NO |
| 1-Methyl-6-iodo-pseudo-UTP | — | U | NO |
| 1-Methyl-6-iso-propyl-pseudo-UTP | — | U | NO |
| 1-Methyl-6-methoxy-pseudo-UTP | — | U | NO |

| Name | Symbol | Base | Naturally Occurring |
|---|---|---|---|
| 1-Methyl-6-methylamino-pseudo-UTP | — | U | NO |
| 1-Methyl-6-phenyl-pseudo-UTP | — | U | NO |
| 1-Methyl-6-propyl-pseudo-UTP | — | U | NO |
| 1-Methyl-6-tert-butyl-pseudo-UTP | — | U | NO |
| 1-Methyl-6-trifluoromethoxy-pseudo-UTP | — | U | NO |
| 1-Methyl-6-trifluoromethyl-pseudo-UTP | — | U | NO |
| 1-Morpholinomethylpseudouridine TP | — | U | NO |
| 1-Pentyl-pseudo-UTP | — | U | NO |
| 1-Phenyl-pseudo-UTP | — | U | NO |
| 1-Pivaloylpseudouridine TP | — | U | NO |
| 1-Propargylpseudouridine TP | — | U | NO |
| 1-Propyl-pseudo-UTP | — | U | NO |
| 1-propynyl-pseudouridine | — | U | NO |
| 1-p-tolyl-pseudo-UTP | — | U | NO |
| 1-tert-Butyl-pseudo-UTP | — | U | NO |
| 1-Thiomethoxymethylpseudouridine TP | — | U | NO |
| 1-Thiomorpholinomethylpseudouridine TP | — | U | NO |
| 1-Trifluoroacetylpseudouridine TP | — | U | NO |
| 1-Trifluoromethyl-pseudo-UTP | — | U | NO |
| 1-Vinylpseudouridine TP | — | U | NO |
| 2,2'-anhydro-uridine TP | — | U | NO |
| 2'-bromo-deoxyuridine TP | — | U | NO |
| 2'-F-5-Methyl-2'-deoxy-UTP | — | U | NO |
| 2'-OMe-5-Me-UTP | — | U | NO |
| 2'-OMe-pseudo-UTP | — | U | NO |
| 2'-a-Ethynyluridine TP | — | U | NO |
| 2'-a-Trifluoromethyluridine TP | — | U | NO |
| 2'-b-Ethynyluridine TP | — | U | NO |
| 2'-b-Trifluoromethyluridine TP | — | U | NO |
| 2'-Deoxy-2',2'-difluorouridine TP | — | U | NO |
| 2'-Deoxy-2'-a-mercaptouridine TP | — | U | NO |
| 2'-Deoxy-2'-a-thiomethoxyuridine TP | — | U | NO |
| 2'-Deoxy-2'-b-aminouridine TP | — | U | NO |
| 2'-Deoxy-2'-b-azidouridine TP | — | U | NO |
| 2'-Deoxy-2'-b-bromouridine TP | — | U | NO |
| 2'-Deoxy-2'-b-chlorouridine TP | — | U | NO |
| 2'-Deoxy-2'-b-fluorouridine TP | — | U | NO |
| 2'-Deoxy-2'-b-iodouridine TP | — | U | NO |
| 2'-Deoxy-2'-b-mercaptouridine TP | — | U | NO |
| 2'-Deoxy-2'-b-thiomethoxyuridine TP | — | U | NO |
| 2-methoxy-4-thio-uridine | — | U | NO |
| 2-methoxyuridine | — | U | NO |
| 2'-O-Methyl-5-(1-propynyl)uridine TP | — | U | NO |
| 3-Alkyl-pseudo-UTP | — | U | NO |
| 4'-Azidouridine TP | — | U | NO |
| 4'-Carbocyclic uridine TP | — | U | NO |
| 4'-Ethynyluridine TP | — | U | NO |
| 5-(1-Propynyl)ara-uridine TP | — | U | NO |
| 5-(2-Furanyl)uridine TP | — | U | NO |
| 5-Cyanouridine TP | — | U | NO |
| 5-Dimethylaminouridine TP | — | U | NO |
| 5'-Homo-uridine TP | — | U | NO |
| 5-iodo-2'-fluoro-deoxyuridine TP | — | U | NO |
| 5-Phenylethynyluridine TP | — | U | NO |
| 5-Trideuteromethyl-6-deuterouridine TP | — | U | NO |
| 5-Trifluoromethyl-Uridine TP | — | U | NO |
| 5-Vinylarauridine TP | — | U | NO |
| 6-(2,2,2-Trifluoroethyl)-pseudo-UTP | — | U | NO |
| 6-(4-Morpholino)-pseudo-UTP | — | U | NO |
| 6-(4-Thiomorpholino)-pseudo-UTP | — | U | NO |
| 6-(Substituted-Phenyl)-pseudo-UTP | — | U | NO |
| 6-Amino-pseudo-UTP | — | U | NO |
| 6-Azido-pseudo-UTP | — | U | NO |
| 6-Bromo-pseudo-UTP | — | U | NO |
| 6-Butyl-pseudo-UTP | — | U | NO |
| 6-Chloro-pseudo-UTP | — | U | NO |
| 6-Cyano-pseudo-UTP | — | U | NO |
| 6-Dimethylamino-pseudo-UTP | — | U | NO |
| 6-Ethoxy-pseudo-UTP | — | U | NO |
| 6-Ethylcarboxylate-pseudo-UTP | — | U | NO |
| 6-Ethyl-pseudo-UTP | — | U | NO |
| 6-Fluoro-pseudo-UTP | — | U | NO |
| 6-Formyl-pseudo-UTP | — | U | NO |
| 6-Hydroxyamino-pseudo-UTP | — | U | NO |
| 6-Hydroxy-pseudo-UTP | — | U | NO |
| 6-Iodo-pseudo-UTP | — | U | NO |
| 6-iso-Propyl-pseudo-UTP | — | U | NO |
| 6-Methoxy-pseudo-UTP | — | U | NO |
| 6-Methylamino-pseudo-UTP | — | U | NO |
| 6-Methyl-pseudo-UTP | — | U | NO |
| 6-Phenyl-pseudo-UTP | — | U | NO |
| 6-Phenyl-pseudo-UTP | — | U | NO |
| 6-Propyl-pseudo-UTP | — | U | NO |
| 6-tert-Butyl-pseudo-UTP | — | U | NO |
| 6-Trifluoromethoxy-pseudo-UTP | — | U | NO |
| 6-Trifluoromethyl-pseudo-UTP | — | U | NO |
| Alpha-thio-pseudo-UTP | — | U | NO |
| Pseudouridine 1-(4-methylbenzenesulfonic acid) TP | — | U | NO |
| Pseudouridine 1-(4-methylbenzoic acid) TP | — | U | NO |
| Pseudouridine TP 1-[3-(2-ethoxy)]propionic acid | — | U | NO |
| Pseudouridine TP 1-[3-{2-(2-[2-(2-ethoxy)-ethoxy]-ethoxy)-ethoxy}]propionic acid | — | U | NO |
| Pseudouridine TP 1-[3-{2-(2-[2{2(2-ethoxy)-ethoxy}-ethoxy]-ethoxy)-ethoxy}]propionic acid | — | U | NO |
| Pseudouridine TP 1-[3-{2-(2-[2-ethoxy]-ethoxy)-ethoxy}]propionic acid | — | U | NO |
| Pseudouridine TP 1-[3-{2-(2-ethoxy)-ethoxy}] propionic acid | — | U | NO |
| Pseudouridine TP 1-methylphosphonic acid | — | U | NO |
| Pseudouridine TP 1-methylphosphonic acid diethyl ester | — | U | NO |
| Pseudo-UTP-N1-3-propionic acid | — | U | NO |
| Pseudo-UTP-N1-4-butanoic acid | — | U | NO |
| Pseudo-UTP-N1-5-pentanoic acid | — | U | NO |
| Pseudo-UTP-N1-6-hexanoic acid | — | U | NO |
| Pseudo-UTP-N1-7-heptanoic acid | — | U | NO |
| Pseudo-UTP-N1-methyl-p-benzoic acid | — | U | NO |
| Pseudo-UTP-N1-p-benzoic acid | — | U | NO |
| Wybutosine | yW | W | YES |
| Hydroxywybutosine | OHyW | W | YES |
| Isowyosine | imG2 | W | YES |
| Peroxywybutosine | o2yW | W | YES |
| undermodified hydroxywybutosine | OHyW* | W | YES |
| 4-demethylwyosine | imG-14 | W | YES |

In some embodiments, the modified nucleobase is pseudouridine (ψ), N1-methylpseudouridine (m$^1$ψ), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine. In some embodiments, an RNA of the invention includes a combination of one or more of the aforementioned modified nucleobases (e.g., a combination of 2, 3 or 4 of the aforementioned modified nucleobases.)

In some embodiments, the modified nucleobase is 1-methyl-pseudouridine (m$^1$ψ), 5-methoxy-uridine (mo$^5$U), 5-methyl-cytidine (m$^5$C), pseudouridine (ψ), α-thio-guanosine, or α-thio-adenosine. In some embodiments, an mRNA of the invention includes a combination of one or more of the aforementioned modified nucleobases (e.g., a combination of 2, 3 or 4 of the aforementioned modified nucleobases.)

In some embodiments, the RNA comprises pseudouridine (ψ) and 5-methyl-cytidine (m$^5$C). In some embodiments, the RNA comprises 1-methyl-pseudouridine (m$^1$ψ). In some embodiments, the RNA comprises 1-methyl-pseudouridine (m$^1$ψ) and 5-methyl-cytidine (m$^5$C). In some embodiments, the RNA comprises 2-thiouridine (s$^2$U). In some embodiments, the RNA comprises 2-thiouridine and 5-methyl-cytidine (m$^5$C). In some embodiments, the RNA comprises 5-methoxy-uridine (mo$^5$U). In some embodiments, the RNA comprises 5-methoxy-uridine (mo$^5$U) and 5-methyl-cytidine (m$^5$C). In some embodiments, the RNA comprises 2'-O-methyl uridine. In some embodiments, the RNA comprises 2'-O-methyl uridine and 5-methyl-cytidine (m$^5$C). In some embodiments, the RNA comprises N6-methyl-adenosine (m$^6$A). In some embodiments, the RNA comprises N6-methyl-adenosine (m$^6$A) and 5-methyl-cytidine (m$^5$C).

In certain embodiments, an RNA of the invention is uniformly modified (i.e., fully modified, modified throughout the entire sequence) for a particular modification. For example, an RNA can be uniformly modified with 5-methyl-cytidine (m$^5$C), meaning that all cytosine residues in the RNA sequence are replaced with 5-methyl-cytidine (m$^5$C). Similarly, RNAs of the invention can be uniformly modified for any type of nucleotide residue present in the sequence by replacement with a modified residue such as those set forth above.

In some embodiments, the modified nucleobase is a modified cytosine. Exemplary nucleobases, nucleosides, and nucleotides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), 2-thio-5-methyl-cytidine.

In some embodiments, the modified nucleobase is a modified uridine. Exemplary nucleobases, nucleosides, and nucleotides having a modified uridine include 5-cyano uridine or 4'-thio uridine.

In some embodiments, the modified nucleobase is a modified adenine. Exemplary nucleobases, nucleosides, and nucleotides having a modified adenine include 7-deaza-adenine, 1-methyl-adenosine (m1A), 2-methyl-adenine (m2A), N6-methyl-adenosine (m6A), and 2,6-Diaminopurine.

In some embodiments, the modified nucleobase is a modified guanine. Exemplary nucleobases, nucleosides, and nucleotides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

In one embodiment, the polynucleotides of the present invention, such as IVT polynucleotides, may have a uniform chemical modification of all or any of the same nucleotide type or a population of modifications produced by mere downward titration of the same starting modification in all or any of the same nucleotide type, or a measured percent of a chemical modification of any of the same nucleotide type but with random incorporation, such as where all uridines are replaced by a uridine analog, e.g., pseudouridine. In another embodiment, the polynucleotides may have a uniform chemical modification of two, three, or four of the same nucleotide type throughout the entire polynucleotide (such as all uridines and all cytosines, etc. are modified in the same way). When the polynucleotides of the present invention are chemically and/or structurally modified the polynucleotides may be referred to as "modified polynucleotides."

Generally, the length of the IVT polynucleotide (e.g., IVT RNA) encoding a polypeptide of interest is greater than about 30 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000, 4,000, 5,000, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the IVT polynucleotide (e.g., IVT RNA) includes from about 30 to about 100,000 nucleotides (e.g., from 30 to 50, from 30 to 100, from 30 to 250, from 30 to 500, from 30 to 1,000, from 30 to 1,500, from 30 to 3,000, from 30 to 5,000, from 30 to 7,000, from 30 to 10,000, from 30 to 25,000, from 30 to 50,000, from 30 to 70,000, from 100 to 250, from 100 to 500, from 100 to 1,000, from 100 to 1,500, from 100 to 3,000, from 100 to 5,000, from 100 to 7,000, from 100 to 10,000, from 100 to 25,000, from 100 to 50,000, from 100 to 70,000, from 100 to 100,000, from 500 to 1,000, from 500 to 1,500, from 500 to 2,000, from 500 to 3,000, from 500 to 5,000, from 500 to 7,000, from 500 to 10,000, from 500 to 25,000, from 500 to 50,000, from 500 to 70,000, from 500 to 100,000, from 1,000 to 1,500, from 1,000 to 2,000, from 1,000 to 3,000, from 1,000 to 5,000, from 1,000 to 7,000, from 1,000 to 10,000, from 1,000 to 25,000, from 1,000 to 50,000, from 1,000 to 70,000, from 1,000 to 100,000, from 1,500 to 3,000, from 1,500 to 5,000, from 1,500 to 7,000, from 1,500 to 10,000, from 1,500 to 25,000, from 1,500 to 50,000, from 1,500 to 70,000, from 1,500 to 100,000, from 2,000 to 3,000, from 2,000 to 5,000, from 2,000 to 7,000, from 2,000 to 10,000, from 2,000 to 25,000, from 2,000 to 50,000, from 2,000 to 70,000, and from 2,000 to 100,000).

In some embodiments, a nucleic acid as described herein is a chimeric polynucleotide. Chimeric polynucleotides or RNA constructs maintain a modular organization similar to IVT polynucleotides, but the chimeric polynucleotides comprise one or more structural and/or chemical modifications or alterations which impart useful properties to the polynucleotide. As such, the chimeric polynucleotides which are modified RNA molecules of the present invention are termed "chimeric modified RNA" or "chimeric RNA." Chimeric polynucleotides have portions or regions which differ in size and/or chemical modification pattern, chemical modification position, chemical modification percent or chemical modification population and combinations of the foregoing.

Polypeptides of Interest

In some embodiments of the invention the is one or more of the following: mRNA, modified mRNA, unmodified RNA, lncRNA, self-replicating RNA, circular RNA, CRISPR guide RNA, and the like. In embodiments the RNA is RNA that encodes a polypeptide, such as mRNA or self-replicating RNA.

In exemplary aspects of the invention, highly pure RNAs compositions are used to produce polypeptides of interest, e.g., therapeutic proteins, vaccine antigen, and the like. In some embodiments, the nucleic acids are therapeutic RNAs. As used herein, the term "therapeutic mRNA" refers to an mRNA that encodes a therapeutic protein. Therapeutic proteins mediate a variety of effects in a host cell or a subject in order to treat a disease or ameliorate the signs and symptoms of a disease. For example, a therapeutic protein can replace a protein that is deficient or abnormal, augment the function of an endogenous protein, provide a novel function to a cell (e.g., inhibit or activate an endogenous cellular activity, or act as a delivery agent for another therapeutic compound (e.g., an antibody-drug conjugate). Therapeutic mRNA may be useful for the treatment of the following diseases and conditions: bacterial infections, viral infections, parasitic infections, cell proliferation disorders, genetic disorders, and autoimmune disorders.

Thus, the polynucleotides of the invention can be used as therapeutic or prophylactic agents. They are provided for use in medicine. For example, the RNA described herein can be administered to a subject, wherein the polynucleotides are translated in vivo to produce a therapeutic peptide. Provided are compositions, methods, kits, and reagents for diagnosis, treatment or prevention of a disease or condition in humans and other mammals. The active therapeutic agents of the invention include the polynucleotides, cells containing polynucleotides or polypeptides translated from the polynucleotides.

The polynucleotides may be induced for translation in a cell, tissue or organism. Such translation can be in vivo, ex vivo, in culture, or in vitro. The cell, tissue or organism is contacted with an effective amount of a composition containing a polynucleotide which contains the RNA polynucleotides.

An "effective amount" of the polynucleotides are provided based, at least in part, on the target tissue, target cell type, means of administration, physical characteristics of the polynucleotide (e.g., size, and extent of modified nucleotides) and other components of the polynucleotides, and other determinants. In general, an effective amount of the polynucleotides provides an induced or boosted peptide production in the cell, preferably more efficient than a composition containing a corresponding unmodified polynucleotide encoding the same peptide. Increased peptide production may be demonstrated by increased cell transfection, increased protein translation from the polynucleotide, decreased nucleic acid degradation (as demonstrated, e.g., by increased duration of protein translation from a modified polynucleotide), or altered peptide production in the host cell.

The RNA of the present invention may be designed to encode polypeptides of interest selected from any of several target categories including, but not limited to, biologics, antibodies, vaccines, therapeutic proteins or peptides, cell penetrating peptides, secreted proteins, plasma membrane proteins, cytoplasmic or cytoskeletal proteins, intracellular membrane bound proteins, nuclear proteins, proteins associated with human disease, targeting moieties or those proteins encoded by the human genome for which no therapeutic indication has been identified but which nonetheless have utility in areas of research and discovery. "Therapeutic protein" refers to a protein that, when administered to a cell has a therapeutic, diagnostic, and/or prophylactic effect and/or elicits a desired biological and/or pharmacological effect.

The RNA disclosed herein, may encode one or more biologics. As used herein, a "biologic" is a polypeptide-based molecule produced by the methods provided herein and which may be used to treat, cure, mitigate, prevent, or diagnose a serious or life-threatening disease or medical condition. Biologics, according to the present invention include, but are not limited to, allergenic extracts (e.g. for allergy shots and tests), blood components, gene therapy products, human tissue or cellular products used in transplantation, vaccines, monoclonal antibodies, cytokines, growth factors, enzymes, thrombolytics, and immunomodulators, among others.

According to the present invention, one or more biologics currently being marketed or in development may be encoded by the RNA of the present invention. While not wishing to be bound by theory, it is believed that incorporation of the encoding polynucleotides of a known biologic into the RNA of the invention will result in improved therapeutic efficacy due at least in part to the specificity, purity and/or selectivity of the construct designs.

The RNA disclosed herein, may encode one or more antibodies or fragments thereof. The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules), as well as antibody fragments. The term "immunoglobulin" (Ig) is used interchangeably with "antibody" herein. As used herein, the term "monoclonal antibody" refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity. Chimeric antibodies of interest herein include, but are not limited to, "primatized" antibodies comprising variable domain antigen-binding sequences derived from a non-human primate (e.g., Old World Monkey, Ape etc.) and human constant region sequences.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies; nanobodies; single-chain antibody molecules and multispecific antibodies formed from antibody fragments.

Any of the five classes of immunoglobulins, IgA, IgD, IgE, IgG and IgM, may be encoded by the RNA of the invention, including the heavy chains designated alpha, delta, epsilon, gamma and mu, respectively. Also included are polynucleotide sequences encoding the subclasses, gamma and mu. Hence any of the subclasses of antibodies may be encoded in part or in whole and include the following subclasses: IgG1, IgG2, IgG3, IgG4, IgA1 and IgA2. According to the present invention, one or more antibodies or fragments currently being marketed or in development may be encoded by the RNA of the present invention.

Antibodies encoded in the RNA of the invention may be utilized to treat conditions or diseases in many therapeutic areas such as, but not limited to, blood, cardiovascular, CNS, poisoning (including antivenoms), dermatology, endocrinology, gastrointestinal, medical imaging, musculoskeletal, oncology, immunology, respiratory, sensory and anti-infective.

In one embodiment, RNA disclosed herein may encode monoclonal antibodies and/or variants thereof. Variants of antibodies may also include, but are not limited to, substitutional variants, conservative amino acid substitution, insertional variants, deletional variants and/or covalent derivatives. In one embodiment, the RNA disclosed herein may encode an immunoglobulin Fc region. In another embodiment, the RNA may encode a variant immunoglobulin Fc region.

The mRNA disclosed herein, may encode one or more vaccine antigens. As used herein, a "vaccine antigen" is a biological preparation that improves immunity to a particular disease or infectious agent. According to the present invention, one or more vaccine antigens currently being marketed or in development may be encoded by the RNA of the present invention.

Vaccine antigens encoded in the RNA of the invention may be utilized to treat conditions or diseases in many therapeutic areas such as, but not limited to, cancer, allergy and infectious disease. In some embodiments the cancer vaccines may be personalized cancer vaccines in the form of a concatemer or individual RNAs encoding peptide epitopes or a combination thereof.

The RNA of the present invention may be designed to encode on or more antimicrobial peptides (AMP) or antiviral peptides (AVP). AMPs and AVPs have been isolated and described from a wide range of animals such as, but not limited to, microorganisms, invertebrates, plants, amphibians, birds, fish, and mammals. The anti-microbial polypeptides described herein may block cell fusion and/or viral entry by one or more enveloped viruses (e.g., HIV, HCV). For example, the anti-microbial polypeptide can comprise or consist of a synthetic peptide corresponding to a region, e.g., a consecutive sequence of at least about 5, 10, 15, 20, 25, 30, 35, 40, 45, 50, 55, or 60 amino acids of the transmembrane subunit of a viral envelope protein, e.g., HIV-1 gp120 or gp41. The amino acid and nucleotide sequences of HIV-1 gp120 or gp41 are described in, e.g., Kuiken et al., (2008). "HIV Sequence Compendium," Los Alamos National Laboratory.

In some embodiments, the anti-microbial polypeptide may have at least about 75%, 80%, 85%, 90%, 95%, 100% sequence homology to the corresponding viral protein sequence. In some embodiments, the anti-microbial polypeptide may have at least about 75%, 80%, 85%, 90%, 95%, or 100% sequence homology to the corresponding viral protein sequence.

In other embodiments, the anti-microbial polypeptide may comprise or consist of a synthetic peptide corresponding to a region, e.g., a consecutive sequence of at least about 5, 10, 15, 20, 25, 30, 35, 40, 45, 50, 55, or 60 amino acids of the binding domain of a capsid binding protein. In some embodiments, the anti-microbial polypeptide may have at least about 75%, 80%, 85%, 90%, 95%, or 100% sequence homology to the corresponding sequence of the capsid binding protein.

The anti-microbial polypeptides described herein may block protease dimerization and inhibit cleavage of viral proproteins (e.g., HIV Gag-pol processing) into functional proteins thereby preventing release of one or more enveloped viruses (e.g., HIV, HCV). In some embodiments, the anti-microbial polypeptide may have at least about 75%, 80%, 85%, 90%, 95%, 100% sequence homology to the corresponding viral protein sequence.

In other embodiments, the anti-microbial polypeptide can comprise or consist of a synthetic peptide corresponding to a region, e.g., a consecutive sequence of at least about 5, 10, 15, 20, 25, 30, 35, 40, 45, 50, 55, or 60 amino acids of the binding domain of a protease binding protein. In some embodiments, the anti-microbial polypeptide may have at least about 75%, 80%, 85%, 90%, 95%, 100% sequence homology to the corresponding sequence of the protease binding protein.

A non-limiting list of infectious diseases that the RNA vaccine antigens or anti-microbial peptides may treat is presented below: human immunodeficiency virus (HIV), HIV resulting in mycobacterial infection, AIDS related Cacheixa, AIDS related Cytomegalovirus infection, HIV-associated nephropathy, Lipodystrophy, AID related cryptococcal meningitis, AIDS related neutropaenia, *Pneumocysitis jiroveci* (*Pneumocystis carinii*) infections, AID related toxoplasmosis, hepatitis A, B, C, D or E, herpes, herpes zoster (chicken pox), German measles (rubella virus), yellow fever, dengue fever etc. (flavi viruses), flu (influenza viruses), haemorrhagic infectious diseases (Marburg or Ebola viruses), bacterial infectious diseases such as Legionnaires' disease (*Legionella*), gastric ulcer (*Helicobacter*), cholera (*Vibrio*), *E. coli* infections, staphylococcal infections, *salmonella* infections or streptococcal infections, tetanus (*Clostridium tetani*), protozoan infectious diseases (malaria, sleeping sickness, leishmaniasis, toxoplasmosis, i.e. infections caused by *plasmodium*, trypanosomes, *leishmania* and *toxoplasma*), diphtheria, leprosy, measles, pertussis, rabies, tetanus, tuberculosis, typhoid, varicella, diarrheal infections such as *Amoebiasis, Clostridium difficile*-associated diarrhea (CDAD), Cryptosporidiosis, Giardiasis, Cyclosporiasis and Rotaviral gastroenteritis, encephalitis such as Japanese encephalitis, Wester equine encephalitis and Tick-borne encephalitis (TBE), fungal skin diseases such as candidiasis, onychomycosis, *Tinea captis*/scal ringworm, *Tinea corporis*/body ringworm, *Tinea cruris*/jock itch, sporotrichosis and *Tinea pedis*/Athlete's foot, Meningitis such as *Haemophilus influenza* type b (Hib), Meningitis, viral, meningococcal infections and pneumococcal infection, neglected tropical diseases such as Argentine haemorrhagic fever, Leishmaniasis, Nematode/roundworm infections, Ross river virus infection and West Nile virus (WNV) disease, Non-HIV STDs such as Trichomoniasis, Human papillomavirus (HPV) infections, sexually transmitted chlamydial diseases, Chancroid and Syphilis, Non-septic bacterial infections such as cellulitis, lyme disease, MRSA infection, *pseudomonas*, staphylococcal infections, Boutonneuse fever, Leptospirosis, Rheumatic fever, Botulism, Rickettsial disease and Mastoiditis, parasitic infections such as Cysticercosis, Echinococcosis, Trematode/Fluke infections, Trichinellosis, Babesiosis, Hypodermyiasis, Diphyllobothriasis and Trypanosomiasis, respiratory infections such as adenovirus infection, aspergillosis infections, avian (H5N1) influenza, influenza, RSV infections, severe acute respiratory syndrome (SARS), sinusitis, Legionellosis, Coccidioidomycosis and swine (H1N1) influenza, sepsis such as bacteraemia, sepsis/septic shock, sepsis in premature infants, urinary tract infection such as vaginal infections (bacterial), vaginal infections (fungal) and gonococcal infection, viral skin diseases such as B19 parvovirus infections, warts, genital herpes, orofacial herpes, shingles, inner ear infections, fetal cytomegalovirus syndrome, foodborn illnesses such as brucellosis (*Brucella* species), *Clostridium perfringens* (Epsilon toxin), *E. Coli* O157:H7 (*Escherichia coli*), *Salmonellosis* (*Salmonella* species), Shingellosis (*Shingella*), Vibriosis and Listeriosis, bioterrorism and potential epidemic diseases such as Ebola haemorrhagic fever, Lassa fever, Marburg haemorrhagic fever, plague, Anthrax Nipah virus disease, Hanta virus, Smallpox, Glanders (*Burkholderia mallei*), Melioidosis (*Burkholderia pseudomallei*), Psittacosis (*Chlamydia psittaci*), Q fever (*Coxiella burnetii*), Tularemia (Fancisella *tularensis*), rubella, mumps and polio.

The RNA disclosed herein, may encode one or more validated or "in testing" therapeutic proteins or peptides. According to the present invention, one or more therapeutic proteins or peptides currently being marketed or in development may be encoded by the RNA of the present invention. Therapeutic proteins and peptides encoded in the RNA of the invention may be utilized to treat conditions or diseases in many therapeutic areas such as, but not limited to, blood, cardiovascular, CNS, poisoning (including antivenoms), dermatology, endocrinology, genetic, genitourinary, gastrointestinal, musculoskeletal, oncology, and immunology, respiratory, sensory and anti-infective.

The RNA disclosed herein, may encode one or more cell-penetrating polypeptides. As used herein, "cell-penetrating polypeptide" or CPP refers to a polypeptide which may facilitate the cellular uptake of molecules. A cell-penetrating polypeptide of the present invention may contain one or more detectable labels. The polypeptides may be partially labeled or completely labeled throughout. The RNA may encode the detectable label completely, partially or not at all. The cell-penetrating peptide may also include a signal sequence. As used herein, a "signal sequence" refers to a sequence of amino acid residues bound at the amino terminus of a nascent protein during protein translation. The signal sequence may be used to signal the secretion of the cell-penetrating polypeptide.

In one embodiment, the RNA may also encode a fusion protein. The fusion protein may be created by operably linking a charged protein to a therapeutic protein. As used herein, "operably linked" refers to the therapeutic protein and the charged protein being connected in such a way to permit the expression of the complex when introduced into the cell. As used herein, "charged protein" refers to a protein that carries a positive, negative or overall neutral electrical charge. Preferably, the therapeutic protein may be covalently linked to the charged protein in the formation of the fusion protein. The ratio of surface charge to total or surface amino acids may be approximately 0.1, 0.2, 0.3, 0.4, 0.5, 0.6, 0.7, 0.8 or 0.9.

The cell-penetrating polypeptide encoded by the RNA may form a complex after being translated. The complex may comprise a charged protein linked, e.g. covalently linked, to the cell-penetrating polypeptide.

In one embodiment, the cell-penetrating polypeptide may comprise a first domain and a second domain. The first domain may comprise a supercharged polypeptide. The second domain may comprise a protein-binding partner. As used herein, "protein-binding partner" includes, but is not limited to, antibodies and functional fragments thereof, scaffold proteins, or peptides. The cell-penetrating polypeptide may further comprise an intracellular binding partner for the protein-binding partner. The cell-penetrating polypeptide may be capable of being secreted from a cell where the RNA may be introduced. The cell-penetrating polypeptide may also be capable of penetrating the first cell.

In one embodiment, the RNA may encode a cell-penetrating polypeptide which may comprise a protein-binding partner. The protein binding partner may include, but is not limited to, an antibody, a supercharged antibody or a functional fragment. The RNA may be introduced into the cell where a cell-penetrating polypeptide comprising the protein-binding partner is introduced.

Human and other eukaryotic cells are subdivided by membranes into many functionally distinct compartments. Each membrane-bound compartment, or organelle, contains different proteins essential for the function of the organelle. The cell uses "sorting signals" which are amino acid motifs located within the protein, to target proteins to particular cellular organelles. One type of sorting signal, called a signal sequence, a signal peptide, or a leader sequence, directs a class of proteins to an organelle called the endoplasmic reticulum (ER).

Proteins targeted to the ER by a signal sequence can be released into the extracellular space as a secreted protein. Similarly, proteins residing on the cell membrane can also be secreted into the extracellular space by proteolytic cleavage of a "linker" holding the protein to the membrane. While not wishing to be bound by theory, the molecules of the present invention may be used to exploit the cellular trafficking described above. As such, in some embodiments of the invention, RNA are provided to express a secreted protein. In one embodiment, these may be used in the manufacture of large quantities of valuable human gene products.

In some embodiments of the invention, RNA are provided to express a protein of the plasma membrane.

In some embodiments of the invention, RNA are provided to express a cytoplasmic or cytoskeletal protein.

In some embodiments of the invention, RNA are provided to express an intracellular membrane bound protein.

In some embodiments of the invention, RNA are provided to express a nuclear protein.

In some embodiments of the invention, RNA are provided to express a protein associated with human disease.

The RNA may have a nucleotide sequence of a native or naturally occurring RNA or encoding a native or naturally occurring peptide. Alternatively, the RNA may have a nucleotide sequence having a percent identity to the nucleotide sequence of a native or naturally occurring RNA or mRNA may have a nucleotide sequence encoding a peptide having a percent identity to the nucleotide sequence of a native or naturally occurring peptide. The term "identity" as known in the art, refers to a relationship between the sequences of two or more peptides, as determined by comparing the sequences. In the art, identity also means the degree of sequence relatedness between peptides, as determined by the number of matches between strings of two or more amino acid residues. Identity measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Thus, in some embodiments, the peptides encoded by the RNAs are polypeptide variants that may have the same or a similar activity as a reference polypeptide. Alternatively, the variant may have an altered activity (e.g., increased or decreased) relative to a reference polypeptide. Generally, variants of a particular polynucleotide or polypeptide of the invention will have at least about 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.) Other tools are described herein, specifically in the definition of "Identity." Default parameters in the BLAST algorithm include, for example, an expect threshold of 10, Word size of 28, Match/Mismatch Scores 1, −2, Gap costs Linear. Any filter can be applied as well as a selection for species specific repeats, e.g., *Homo sapiens*.

According to the present invention, the polynucleotides include RNA to encode one or more polypeptides of interest or fragments thereof. A polypeptide of interest may include, but is not limited to, whole polypeptides, a plurality of polypeptides or fragments of polypeptides. As used herein, the term "polypeptides of interest" refer to any polypeptide which is selected to be encoded in the primary construct of the present invention. As used herein, "polypeptide" means a polymer of amino acid residues (natural or unnatural) linked together most often by peptide bonds. The term, as used herein, refers to proteins, polypeptides, and peptides of any size, structure, or function. In some instances, the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. They may also comprise single chain or multichain polypeptides such as antibodies or insulin and may be associated or linked. Most commonly disulfide linkages are found in multichain polypeptides. The term polypeptide may also apply to amino acid polymers in which one or more amino acid residues are an artificial chemical analogue of a corresponding naturally occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants will possess at least about 50% identity to a native or reference sequence, and preferably, they will be at least about 80%, more preferably at least about 90% identical to a native or reference sequence.

In some embodiments "variant mimics" are provided. As used herein, the term "variant mimic" is one which contains one or more amino acids which would mimic an activated sequence. For example, glutamate may serve as a mimic for phosphoro-threonine and/or phosphoro-serine. Alternatively, variant mimics may result in deactivation or in an inactivated product containing the mimic, e.g., phenylalanine may act as an inactivating substitution for tyrosine; or alanine may act as an inactivating substitution for serine.

The present invention contemplates several types of compositions which are polypeptide based including variants and derivatives. These include substitutional, insertional, deletion and covalent variants and derivatives. The term "derivative" is used synonymously with the term "variant" but generally refers to a molecule that has been modified and/or changed in any way relative to a reference molecule or starting molecule.

As such, RNA encoding polypeptides containing substitutions, insertions and/or additions, deletions and covalent modifications with respect to reference sequences, in particular the polypeptide sequences disclosed herein, are included within the scope of this invention. For example, sequence tags or amino acids, such as one or more lysines, can be added to the peptide sequences of the invention (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to polypeptides are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid.

"Deletional variants" when referring to polypeptides are those with one or more amino acids in the native or starting amino acid sequence removed. Ordinarily, deletional variants will have one or more amino acids deleted in a particular region of the molecule.

"Covalent derivatives" when referring to polypeptides include modifications of a native or starting protein with an organic proteinaceous or non-proteinaceous derivatizing agent, and/or post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the polypeptides produced in accordance with the present invention.

Other post-translational modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)).

As used herein when referring to polypeptides the term "domain" refers to a motif of a polypeptide having one or more identifiable structural or functional characteristics or properties (e.g., binding capacity, serving as a site for protein-protein interactions).

As used herein when referring to polypeptides the terms "site" as it pertains to amino acid based embodiments is used synonymously with "amino acid residue" and "amino acid side chain." A site represents a position within a peptide or polypeptide that may be modified, manipulated, altered, derivatized or varied within the polypeptide based molecules of the present invention.

As used herein the terms "termini" or "terminus" when referring to polypeptides refers to an extremity of a peptide or polypeptide. Such extremity is not limited only to the first or final site of the peptide or polypeptide but may include additional amino acids in the terminal regions. The polypeptide based molecules of the present invention may be characterized as having both an N-terminus (terminated by an amino acid with a free amino group (NH2)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

Once any of the features have been identified or defined as a desired component of a polypeptide to be encoded by the RNA of the invention, any of several manipulations and/or modifications of these features may be performed by moving, swapping, inverting, deleting, randomizing or duplicating. Furthermore, it is understood that manipulation of features may result in the same outcome as a modification to the molecules of the invention. For example, a manipulation which involved deleting a domain would result in the alteration of the length of a molecule just as modification of a nucleic acid to encode less than a full length molecule would.

Modifications and manipulations can be accomplished by methods known in the art such as, but not limited to, site directed mutagenesis. The resulting modified molecules may then be tested for activity using in vitro or in vivo assays such as those described herein or any other suitable screening assay known in the art.

Formulations/Pharmaceutical Compositions

The present invention provides polynucleotides and pharmaceutical compositions thereof optionally in combination with one or more pharmaceutically acceptable excipients. Pharmaceutical compositions may optionally comprise one or more additional active substances, e.g. therapeutically and/or prophylactically active substances. Pharmaceutical compositions of the present invention may be sterile and/or pyrogen-free. General considerations in the formulation and/or manufacture of pharmaceutical agents may be found, for example, in Remington: The Science and Practice of Pharmacy 21st ed., Lippincott Williams & Wilkins, 2005 (incorporated herein by reference in its entirety).

In some embodiments, compositions are administered to humans, human patients or subjects. For the purposes of the present disclosure, the phrase "active ingredient" generally refers to the polynucleotides, e.g., mRNA encoding polynucleotides to be delivered as described herein.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

The polynucleotides of the invention can be formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein in vivo. In addition to traditional excipients such as any and all solvents, dispersion media, diluents, or other liquid vehicles, dispersion or suspension aids, surface active agents, isotonic agents, thickening or emulsifying agents, preservatives, excipients of the present invention can include, without limitation, lipidoids, liposomes, lipid nanoparticles, polymers, lipoplexes, core-shell nanoparticles, peptides, proteins, cells transfected with polynucleotides, hyaluronidase, nanoparticle mimics and combinations thereof.

In some embodiments, nucleic acid molecules of the invention can be formulated using one or more liposomes, lipoplexes, or lipid nanoparticles. In one embodiment, pharmaceutical compositions of nucleic acid molecules include lipid nanoparticles (LNPs). In some embodiments, lipid nanoparticles are MC3-based lipid nanoparticles.

In one embodiment, the polynucleotides may be formulated in a lipid-polycation complex. The formation of the lipid-polycation complex may be accomplished by methods known in the art. As a non-limiting example, the polycation may include a cationic peptide or a polypeptide such as, but not limited to, polylysine, polyornithine and/or polyarginine. In another embodiment, the polynucleotides may be formulated in a lipid-polycation complex which may further include a non-cationic lipid such as, but not limited to, cholesterol or dioleoyl phosphatidylethanolamine (DOPE).

The liposome formulation may be influenced by, but not limited to, the selection of the cationic lipid component, the degree of cationic lipid saturation, the nature of the PEGylation, ratio of all components and biophysical parameters such as size. In one example by Semple et al. (Semple et al. Nature Biotech. 2010 28:172-176; herein incorporated by reference in its entirety), the liposome formulation was composed of 57.1% cationic lipid, 7.1% dipalmitoylphosphatidylcholine, 34.3% cholesterol, and 1.4% PEG-c-DMA. As another example, changing the composition of the cationic lipid could more effectively deliver siRNA to various antigen presenting cells (Basha et al. Mol Ther. 2011 19:2186-2200; herein incorporated by reference in its entirety). In some embodiments, liposome formulations may comprise from about 35 to about 45% cationic lipid, from about 40% to about 50% cationic lipid, from about 50% to about 60% cationic lipid and/or from about 55% to about 65% cationic lipid. In some embodiments, the ratio of lipid to RNA in liposomes may be from about 5:1 to about 20:1, from about 10:1 to about 25:1, from about 15:1 to about 30:1 and/or at least 30:1.

In some embodiments, the ratio of PEG in the lipid nanoparticle (LNP) formulations may be increased or decreased and/or the carbon chain length of the PEG lipid may be modified from C14 to C18 to alter the pharmacokinetics and/or biodistribution of the LNP formulations. As a non-limiting example, LNP formulations may contain from about 0.5% to about 3.0%, from about 1.0% to about 3.5%, from about 1.5% to about 4.0%, from about 2.0% to about 4.5%, from about 2.5% to about 5.0% and/or from about 3.0% to about 6.0% of the lipid molar ratio of PEG-c-DOMG (R-3-[(ω-methoxy-poly(ethyleneglycol) 2000)carbamoyl)]-1,2-dimyristyloxypropyl-3-amine) (also referred to herein as PEG-DOMG) as compared to the cationic lipid, DSPC and cholesterol. In another embodiment the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In one embodiment, the polynucleotide is formulated in a nanoparticle which may comprise at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In another aspect, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in US Patent Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

In one embodiment, the lipid nanoparticle formulation consists essentially of (i) at least one lipid selected from the group consisting of 2,2-dilinoleyl-4-dimethylaminoethyl-[1, 3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of about 20-60% cationic lipid: 5-25% neutral lipid: 25-55% sterol; 0.5-15% PEG-lipid.

In one embodiment, the formulation includes from about 25% to about 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., from about 35 to about 65%, from about 45 to about 65%, about 60%, about 57.5%, about 50% or about 40% on a molar basis.

In one embodiment, the formulation includes from about 0.5% to about 15% on a molar basis of the neutral lipid e.g., from about 3 to about 12%, from about 5 to about 10% or about 15%, about 10%, or about 7.5% on a molar basis. Exemplary neutral lipids include, but are not limited to, DSPC, POPC, DPPC, DOPE and SM. In one embodiment, the formulation includes from about 5% to about 50% on a molar basis of the sterol (e.g., about 15 to about 45%, about 20 to about 40%, about 40%, about 38.5%, about 35%, or about 31% on a molar basis. An exemplary sterol is cholesterol. In one embodiment, the formulation includes from about 0.5% to about 20% on a molar basis of the PEG or PEG-modified lipid (e.g., about 0.5 to about 10%, about 0.5 to about 5%, about 1.5%, about 0.5%, about 1.5%, about 3.5%, or about 5% on a molar basis. In one embodiment, the PEG or PEG modified lipid comprises a PEG molecule of an average molecular weight of 2,000 Da. In other embodiments, the PEG or PEG modified lipid comprises a PEG molecule of an average molecular weight of less than 2,000, for example around 1,500 Da, around 1,000 Da, or around 500 Da. Exemplary PEG-modified lipids include, but are not limited to, PEG-distearoyl glycerol (PEG-DMG) (also referred herein as PEG-C14 or C14-PEG), PEG-cDMA.

In one embodiment, the formulations of the inventions include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin- MC3-DMA), and di((Z)-non-2-en-1-yl) 9-((4-(dimethylamino)butanoyl)oxy)heptadecanedioate (L319), 0.5-15% of the neutral lipid, 5-50% of the sterol, and 0.5-20% of the PEG or PEG-modified lipid on a molar basis.

In one embodiment, the formulations of the inventions include 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of the neutral lipid, 15-45% of the sterol, and 0.5-10% of the PEG or PEG-modified lipid on a molar basis.

In one embodiment, the formulations of the inventions include 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of the neutral lipid, 25-40% of the sterol, and 0.5-10% of the PEG or PEG-modified lipid on a molar basis.

In one embodiment, the formulations of the inventions include about 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.5% of the neutral lipid, about 31% of the sterol, and about 1.5% of the PEG or PEG-modified lipid on a molar basis.

In one embodiment, the formulations of the inventions include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 38.5% of the sterol, and about 1.5% of the PEG or PEG-modified lipid on a molar basis.

In one embodiment, the formulations of the inventions include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 35% of the sterol, about 4.5% or about 5% of the PEG or PEG-modified lipid, and about 0.5% of the targeting lipid on a molar basis.

In one embodiment, the formulations of the inventions include about 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 15% of the neutral lipid, about 40% of the sterol, and about 5% of the PEG or PEG-modified lipid on a molar basis.

In one embodiment, the formulations of the inventions include about 57.2% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.1% of the neutral lipid, about 34.3% of the sterol, and about 1.4% of the PEG or PEG-modified lipid on a molar basis.

In one embodiment, the formulations of the inventions include about 57.5% of a cationic lipid selected from the PEG lipid is PEG-cDMA (PEG-cDMA is further discussed in Reyes et al. (J. Controlled Release, 107, 276-287 (2005), the contents of which are herein incorporated by reference in its entirety), about 7.5% of the neutral lipid, about 31.5% of the sterol, and about 3.5% of the PEG or PEG-modified lipid on a molar basis.

In preferred embodiments, lipid nanoparticle formulation consists essentially of a lipid mixture in molar ratios of about 20-70% cationic lipid: 5-45% neutral lipid: 20-55% cholesterol: 0.5-15% PEG-modified lipid; more preferably in a molar ratio of about 20-60% cationic lipid: 5-25% neutral lipid: 25-55% cholesterol: 0.5-15% PEG-modified lipid.

In particular embodiments, the molar lipid ratio is approximately 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/ neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/ Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/ 10 (mol % cationic lipid/neutral lipid, e.g., DSPC/Chol/ PEG-modified lipid, e.g., PEG-DMG or PEG-cDMA) or 52/13/30/5 (mol % cationic lipid/neutral lipid, e.g., DSPC/ Chol/PEG-modified lipid, e.g., PEG-DMG or PEG-cDMA).

Exemplary lipid nanoparticle compositions and methods of making same are described, for example, in Semple et al. (2010) Nat. Biotechnol. 28:172-176; Jayarama et al. (2012), Angew. Chem. Int. Ed., 51: 8529-8533; and Maier et al. (2013) Molecular Therapy 21, 1570-1578 (the contents of each of which are incorporated herein by reference in their entirety).

In one embodiment, the lipid nanoparticle formulations described herein may comprise a cationic lipid, a PEG lipid and a structural lipid and optionally comprise a non-cationic lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In one embodiment, the cationic lipid may be any cationic lipid described herein such as, but not limited to, DLin-KC2-DMA, DLin-MC3-DMA and L319.

In one embodiment, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In one embodiment, the cationic lipid may be any cationic lipid described herein such as, but not limited to, DLin-KC2-DMA, DLin-MC3-DMA and L319.

In one embodiment, the lipid nanoparticle formulations described herein may comprise a cationic lipid, a non-cationic lipid, a PEG lipid and a structural lipid. As a non-limiting example, the lipid nanoparticle comprise about 50% of the cationic lipid DLin-KC2-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DMG and about 38.5% of the structural lipid cholesterol. As yet another non-limiting example, the lipid nanoparticle comprise about 55% of the cationic lipid L319, about 10% of the non-cationic lipid DSPC, about 2.5% of the PEG lipid PEG-DMG and about 32.5% of the structural lipid cholesterol.

In one embodiment, the polynucleotides of the invention may be formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the lipid nanoparticles may have a diameter from about 10 to 500 nm. In one embodiment, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm. In some embodiments, the cationic lipid nanoparticle has a mean diameter of 50-150 nm. In some embodiments, the cationic lipid nanoparticle has a mean diameter of 80-100 nm.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In one embodiment, the compositions containing the polynucleotides described herein, formulated in a lipid nanoparticle comprising MC3, Cholesterol, DSPC and PEG2000-DMG, the buffer trisodium citrate, sucrose and water for injection. As a non-limiting example, the composition comprises: 2.0 mg/mL of drug substance, 21.8 mg/mL of MC3, 10.1 mg/mL of cholesterol, 5.4 mg/mL of DSPC, 2.7 mg/mL of PEG2000-DMG, 5.16 mg/mL of trisodium citrate, 71 mg/mL of sucrose and about 1.0 mL of water for injection.

The polynucleotides of the present invention may be administered by any route which results in a therapeutically effective outcome. The present invention provides methods comprising administering polynucleotides and in accordance with the invention to a subject in need thereof. The exact amount required will vary from subject to subject, depending on the species, age, and general condition of the subject, the severity of the disease, the particular composition, its mode of administration, its mode of activity, and the like. Compositions in accordance with the invention are typically formulated in dosage unit form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In certain embodiments, compositions in accordance with the present invention may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used.

A polynucleotide pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

The present invention provides pharmaceutical compositions including polynucleotides (e.g., RNA molecules) and polynucleotide compositions and/or complexes optionally in combination with one or more pharmaceutically acceptable excipients.

The present invention provides polynucleotides (e.g., RNA molecules) and related pharmaceutical compositions and complexes optionally in combination with one or more pharmaceutically acceptable excipients. Pharmaceutical compositions may optionally comprise one or more additional active substances, e.g., therapeutically and/or prophylactically active substances. Pharmaceutical compositions of the present invention may be sterile and/or pyrogen-free. General considerations in the formulation and/or manufacture of pharmaceutical agents may be found, for example, in Remington: The Science and Practice of Pharmacy 21st ed., Lippincott Williams & Wilkins, 2005 (incorporated herein by reference in its entirety).

In some embodiments, compositions are administered to humans, human patients or subjects. For the purposes of the present disclosure, the phrase "active ingredient" generally refers to the polynucleotides (e.g., RNA molecules), to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g., non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1. Manufacture of Polynucleotides

According to the present invention, the manufacture of polynucleotides and or parts or regions thereof may be accomplished utilizing the methods taught in WO2014/152027 filed Mar. 15, 2013 entitled "Manufacturing Methods for Production of RNA Transcripts", the contents of which is incorporated herein by reference in its entirety. Purification methods may include those taught in International Application WO2014/152030 and WO2014/152031, each of which is incorporated herein by reference in its entirety.

Detection and characterization methods of the polynucleotides may be performed as taught in WO2014/144039, which is incorporated herein by reference in its entirety.

Characterization of the polynucleotides of the disclosure may be accomplished using a procedure selected from the group consisting of polynucleotide mapping, reverse transcriptase sequencing, charge distribution analysis, and detection of RNA impurities, wherein characterizing comprises determining the RNA transcript sequence, determining the purity of the RNA transcript, or determining the charge heterogeneity of the RNA transcript. Such methods are taught in, for example, WO2014/144711 and WO2014/144767, the contents of each of which is incorporated herein by reference in its entirety.

Example 2. Chimeric Polynucleotide Synthesis

Introduction

According to the present invention, two regions or parts of a chimeric polynucleotide may be joined or ligated using triphosphate chemistry.

According to this method, a first region or part of 100 nucleotides or less is chemically synthesized with a 5' monophosphate and terminal 3'desOH or blocked OH. If the region is longer than 80 nucleotides, it may be synthesized as two strands for ligation.

If the first region or part is synthesized as a non-positionally modified region or part using in vitro transcription (IVT), conversion the 5' monophosphate with subsequent capping of the 3' terminus may follow.

Monophosphate protecting groups may be selected from any of those known in the art.

The second region or part of the chimeric polynucleotide may be synthesized using either chemical synthesis or IVT methods. IVT methods may include an RNA polymerase that can utilize a primer with a modified cap. Alternatively, a cap of up to 130 nucleotides may be chemically synthesized and coupled to the IVT region or part.

It is noted that for ligation methods, ligation with DNA T4 ligase, followed by treatment with DNAse should readily avoid concatenation.

The entire chimeric polynucleotide need not be manufactured with a phosphate-sugar backbone. If one of the regions or parts encodes a polypeptide, then it is preferable that such region or part comprise a phosphate-sugar backbone.

Ligation is then performed using any known click chemistry, orthoclick chemistry, solulink, or other bioconjugate chemistries known to those in the art.

Synthetic Route

The chimeric polynucleotide is made using a series of starting segments. Such segments include:

(a) Capped and protected 5' segment comprising a normal 3'OH (SEG. 1)

(b) 5' triphosphate segment which may include the coding region of a polypeptide and comprising a normal 3'OH (SEG. 2)

(c) 5' monophosphate segment for the 3' end of the chimeric polynucleotide (e.g., the tail) comprising cordycepin or no 3'OH (SEG. 3)

After synthesis (chemical or IVT), segment 3 (SEG. 3) is treated with cordycepin and then with pyrophosphatase to create the 5' monophosphate.

Segment 2 (SEG. 2) is then ligated to SEG. 3 using RNA ligase. The ligated polynucleotide is then purified and treated with pyrophosphatase to cleave the diphosphate. The treated SEG.2-SEG. 3 construct is then purified and SEG. 1 is ligated to the 5' terminus. A further purification step of the chimeric polynucleotide may be performed.

Where the chimeric polynucleotide encodes a polypeptide, the ligated or joined segments may be represented as: 5'UTR (SEG. 1), open reading frame or ORF (SEG. 2) and 3'UTR+PolyA (SEG. 3).

The yields of each step may be as much as 90-95%.

Example 3: PCR for Production of DNA Template

PCR procedures for the preparation of cDNA are performed using 2×KAPA HIFI™ HotStart ReadyMix by Kapa Biosystems (Woburn, Mass.). This system includes 2×KAPA ReadyMix12.5 µl; Forward Primer (10 uM) 0.75 µl; Reverse Primer (10 uM) 0.75 µl; Template cDNA—100 ng; and dH$_2$O diluted to 25.0 µl. The reaction conditions are at 95° C. for 5 min. and 25 cycles of 98° C. for 20 sec, then 58° C. for 15 sec, then 72° C. for 45 sec, then 72° C. for 5 min. then 4° C.

The reaction is cleaned up using Invitrogen's PURELINK™ PCR Micro Kit (Carlsbad, Calif.) per manufacturer's instructions (up to 5 µg). Larger reactions will require a cleanup using a product with a larger capacity. Following the cleanup, the cDNA is quantified using the NANODROP™ and analyzed by agarose gel electrophoresis to confirm the cDNA is the expected size. The cDNA is then submitted for sequencing analysis before proceeding to the in vitro transcription reaction.

Example 4. IVT and IFN-β Analysis of Short Model RNA-1

IVT reactions can be "spiked" with specific nucleotides, resulting in minimal cytokine response contaminants and better yields. In one process, the GTP ratio to other NTPs was increased, resulting in a higher total NPT load and an increased NTP:Mg$^{2+}$ molar ratio, as shown in Table 1. These specific nucleotides are refried to as short model RNAs. The goal of short model RNAs was to recapitulate the same cytokine signal/effect of equimolar (prior art) vs methods of the invention observed in full length RNAs. The construct was small enough to detect full length impurities by LC/MS which was not currently feasible with full length RNA.

TABLE 1

| Nucleotide Formulations | | | |
|---|---|---|---|
|  | Equimolar | Alpha | GDP alpha |
| [GDP] mM | 0 | 0 | 30 |
| [GTP] mM | 7.5 | 30 | 15 |
| [ATP] mM | 7.5 | 15 | 15 |
| [CTP] mM | 7.5 | 7.5 | 7.5 |
| [UTP] mM | 7.5 | 7.5 | 7.5 |
| Total [Nuc] mM | 30 | 60 | 75 |
| [Mg2+] mM | 40 | 40 | 40 |
| Nuc: Mg2+ | 0.75 | 1.50 | 1.88 |
| Effective [phosphate] | 90 | 180 | 195 |
| T7 (U/µl reaction) | 7 | 14 | 14 |

In order to determine whether a short model transcript prepared using two different IVT processes mimic the in vitro (BJ fibroblast) IFNbeta response that was observed for full length transcripts, independent of experimental process (i.e. crude IVT, ultrafiltered, or dT purified) study was set up. A surrogate RNA, short model RNA-1, produced under the same IVT conditions as the target RNA and from the same DNA template duplex, was generated. The cytokine response mimicked that of full length RNA in an IFN-β assay in BJ fibroblasts (FIG. 1). The short model transcript prepared using the equimolar IVT process has a higher IFNbeta response than material prepared using the alpha IVT process. The cytokine response was preserved after ultrafiltration and dT purification.

Figure 2:
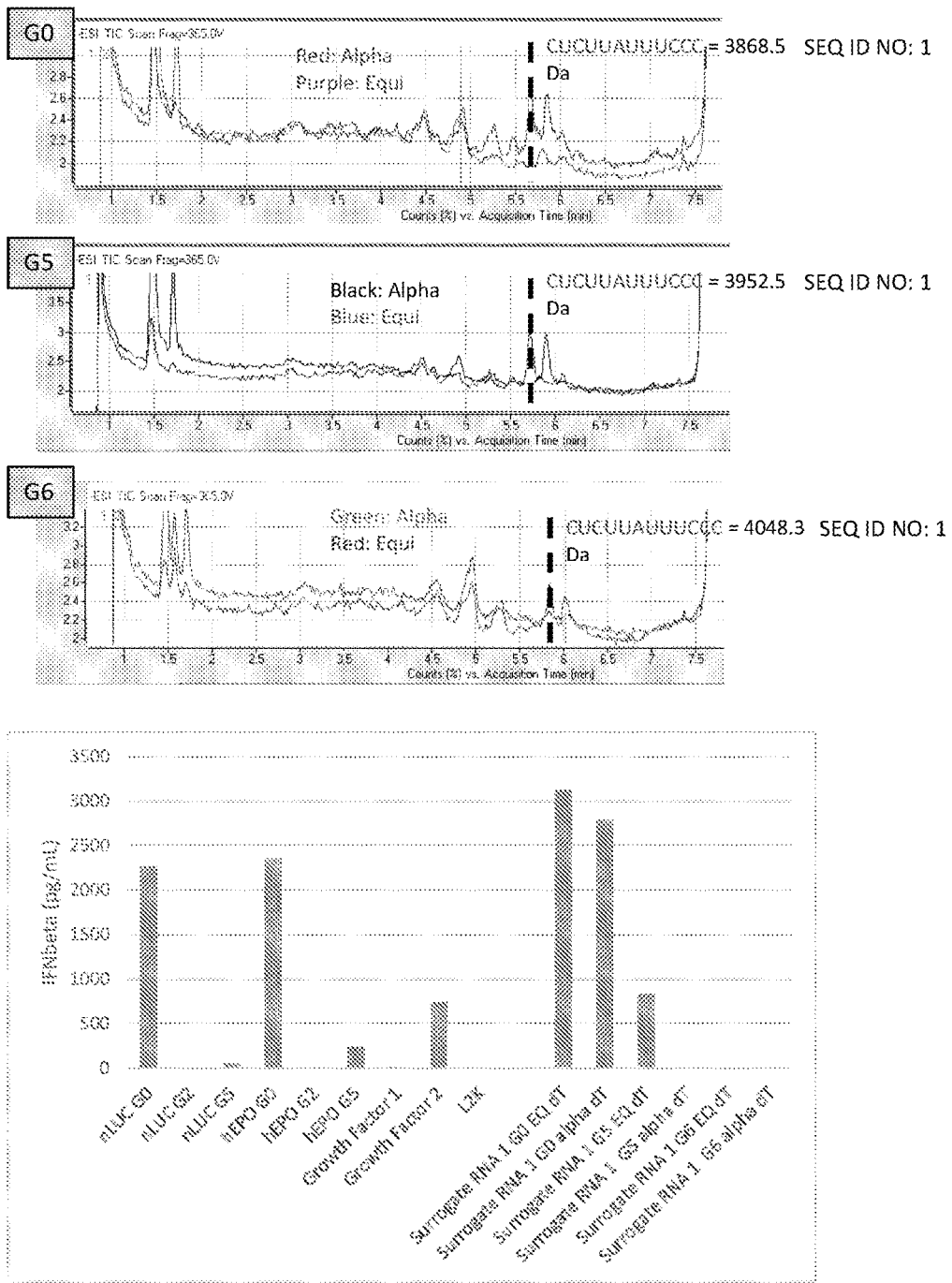
FIG. 2 shows the results of an LCMS analysis of a short model transcript. The model demonstrates that the abortive species are present in all three chemistries. The top trace shows unmodified short model RNA-1, the middle trace shows short model RNA with all uridines modified to pseudouridine and all cytidines modified with 5'O-methyl, and the bottom trace shows short model RNA1 with some uridine and cytidine residues modified.

Furthermore, impurity profiling of short model RNA-1 (all uridines modified to pseudouridine and all cytidnes modified by 5'O-methyl), showed the presence of reverse complements (dsRNA) in the equimolar process but not in Alpha reaction. Nine different species were identified—the overlapping peaks between the two represent abortive species, while the peaks only seen in the equimolar formulation are reverse complementary species. The screen was performed on species with varying amounts of uridine and cytidine modifications, and reverse complementary and abortive species were found in all three (FIG. 2). The abortive transcripts are sense and the reverse complementary are antisense transcripts. IFN-β levels also varied between the three (FIG. 2). The top is G0=Standard A, G, C, U, Mid is G5=Standard A,G,C and 1-methylpseudoU and Bottom is G6=Standard A,G,C and 5-methoxyuridine. Short model transcript prepared by 2 different processes in 3 different chemistries have similar impurity profiles by LCMS, despite differences in the BJF assay, which seems to be sensitive to different chemistries.

Figure 3:
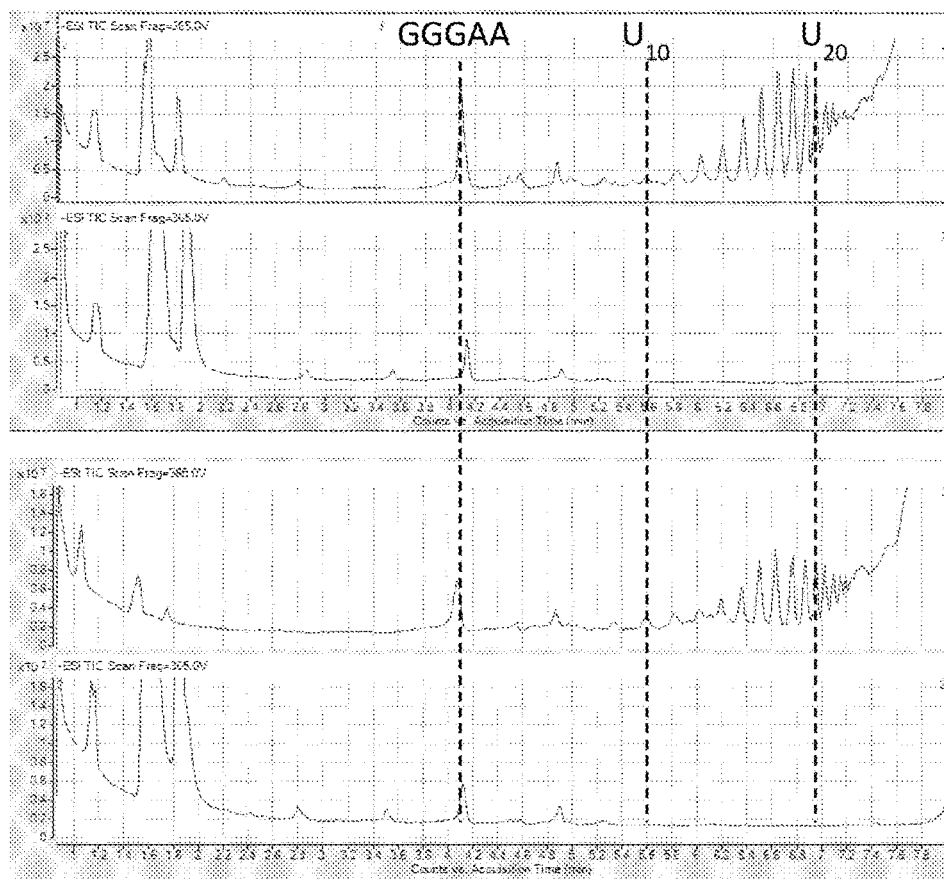
FIG. 3 shows the results of an LCMS analysis of a model transcript. The model demonstrates the impurity profiles of model RNA-4 and hEPO prepared by IVT.

An LCMS analysis of a model transcript and intact transcript were prepared at 25 C for 6 h IVT. A short transcript and full length transcript were prepared using the equimolar and alpha processes at 25 C for 6 h (not our normal IVT, which is 37 C 2 h). Low temperature IVT reactions (<30 C) produce a larger abundance of reverse complement RNAs than 37 C. The impurity profiles of the samples were analyzed by LCMS. Samples prepared using both processes both contained abortive/truncated products. The transcripts prepared using equimolar process contained polyU species of varying lengths. Alpha process still mitigates the formation of reverse complements even at 25 C where abundance was greater than standard conditions using equimolar processes (FIG. 3).

Detection of Complementary/Antisense RNA

Immunostimulatory impurities appear to be driven by RNA-templated RNA transcription, as T7 polymerizes off of the nascent transcribed RNA. The resulting complementary/antisense RNA (dsRNA) that was generated shows mixed bases, a polyU component, and a 5' triphosphate (5'ppp), which initiates with any base. An RNA-templated transcription was performed. Reverse phase purified hEPO G5 (cold) was incubated at 4 mg/mL (consistent with a typical yield of an in vitro transcription reaction), with all the IVT components, except DNA template, which was determined to be below threshold required for in vitro transcription by qPCR, to explore the RNA-templated transcription phenomenon. The materials were analyzed by UPLC and in vitro BJF IFNbeta assay. UPLC analysis demonstrated that aberrant RNA transcription products, and most notably polyU species are produced via RNA-templated transcription (in the absence of DNA template). The reaction performed with RNA and all IVT components was IFNbeta hot, while the reaction performed without RNA was cold. (FIG. 4).

Figure 5A:
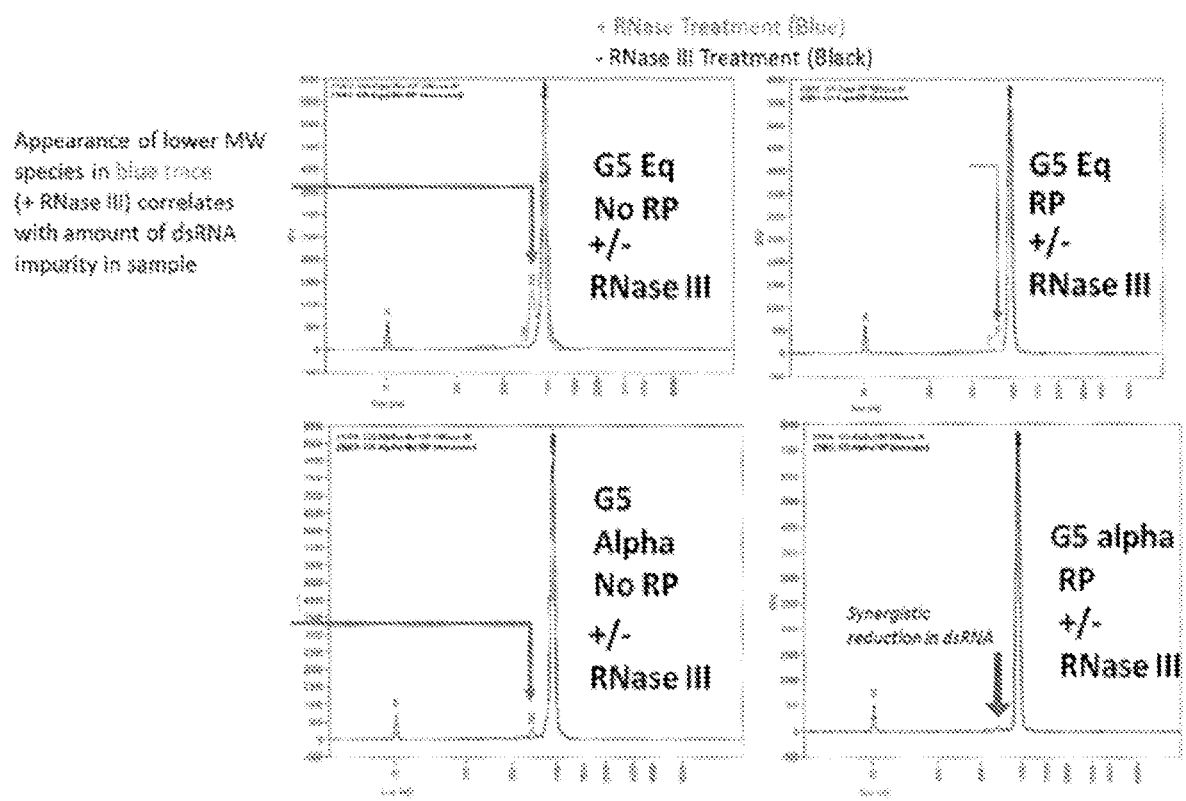
FIGS. 5A and 5B show the impact of reverse-phase (RP) and IVT with an excess of GTP on the amount of RNase III substrate. Both alpha process and RP purification reduce RIII substrate. An additive effect of combining both is shown.

Double-stranded RNA can be cleared from reverse-phase (RP) purified transcribed RNA. A Capillary Electrophoresis analysis of RNase III treated hEPO G5 material was performed. hEPO G5 was prepared using either equimolar or alpha conditions and a portion was purified by RP. The samples were then treated with RNase III and analyzed by capillary electrophoresis. Material prepared by alpha process contained less RNase III substrate than that prepared by equimolar process. RP purification clears most of the RNase III substrate from equi and alpha material Alpha process and Reverse Phase purification appear to provide a synergistic reduction in RNase III substrate (eg dsRNA) (FIG. 5A). A Capillary Electrophoresis analysis of RNase III treated hEPO G0 material was performed. hEPO G0 was prepared using equimolar process and a portion was purified by RP. The samples were then treated with RNase III and analyzed by capillary electrophoresis (blue: treated; black: untreated). Material that was RP purified contained less RNase III substrate than material that was not RP purified (current state of the art) (FIG. 5B).

RNase III is a dsRNA specific nuclease. RNA preps are subjected to RNase III treatment for a fixed time. RNA Purity/impurity profile are compared pre and post RNase III treatment and are measured by HPLC or capillary electrophoresis. The amount of full length product degraded was proportional to the level of double stranded RNA impurities present in the RNA prep. The amount degraded as indicated by a change in apparent size/retention time/was considered to be amount of RNase III substrate. Samples devoid of dsRNA should show nearly identical purity pre and post RNase III treatment. Samples containing significant quantities of dsRNA will show the formation of substantial cleavage product and depletion of full length RNA present in the untreated feedstock as seen by HPLC or capillary electrophoresis. (Ex If 80% of the original mRNA remains post RNase III treatment, 20% was a substrate for RNase III.

Figure 5B:
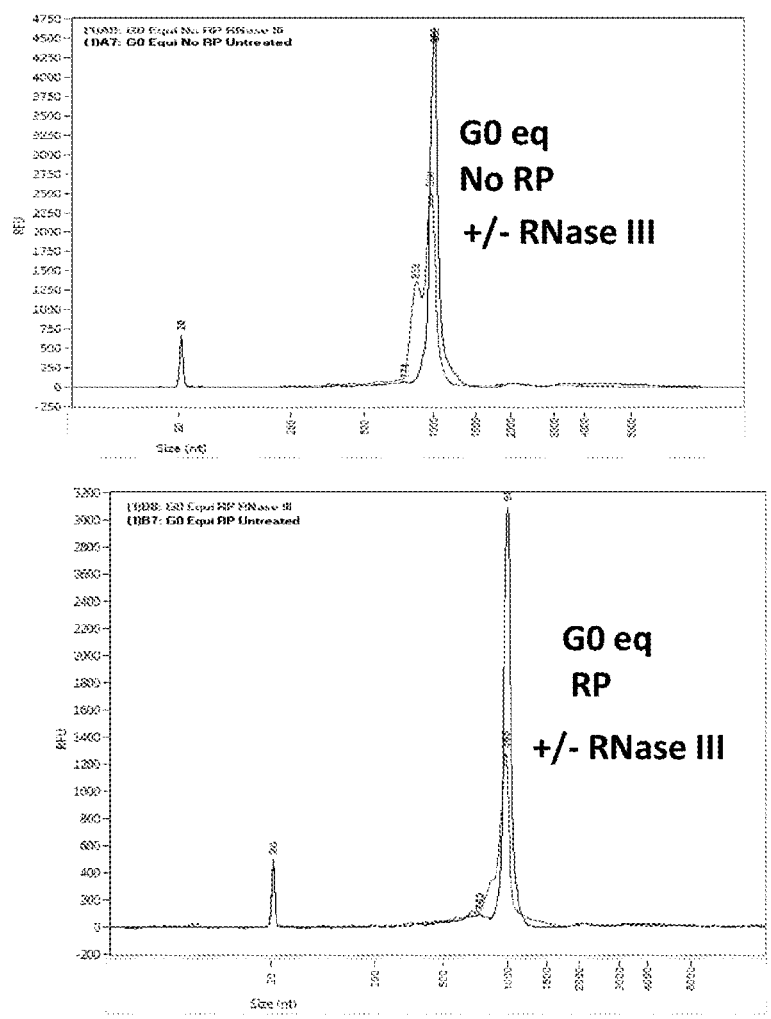
Figure 6:
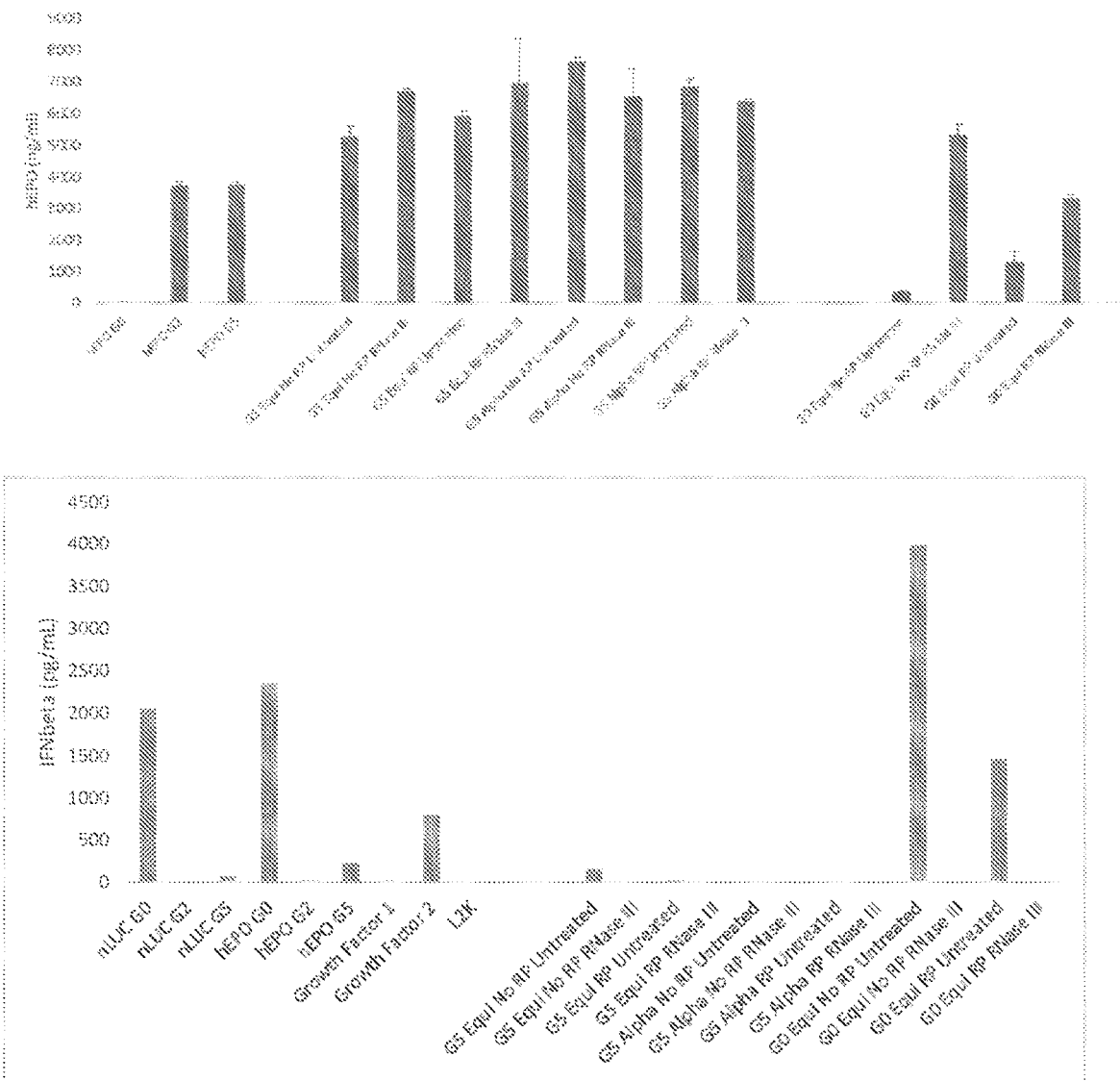
FIG. 6 shows transfection data from hEPO protein expression and IFN-β.

An IFNbeta and hEPO expression analysis of samples from FIGS. 5A and 5B was performed. Treated and untreated samples were analyzed to determine how RNase III treatment affect IFNbeta response and hEPO expression in BJ Fibroblasts (in vitro). It was found that hEPO A100 G5 equimolar material expresses similarly for untreated and RIII treated samples. Cytokine level for equi treated −RP sample reduced after treatment with RIII hEPO A100 G5 alpha material all expressed similarly and had zero/low IFNbeta response. TL material does not express. However, RIII treatment brought CK level down for both + and −RP samples. G0 hEPO A100 material saw the greatest effects from RNase III treatment. After RNase III treatment, both + and −RP purified samples saw an increase in expression and a decrease in IFNbeta level (FIG. 6).

Figure 7:
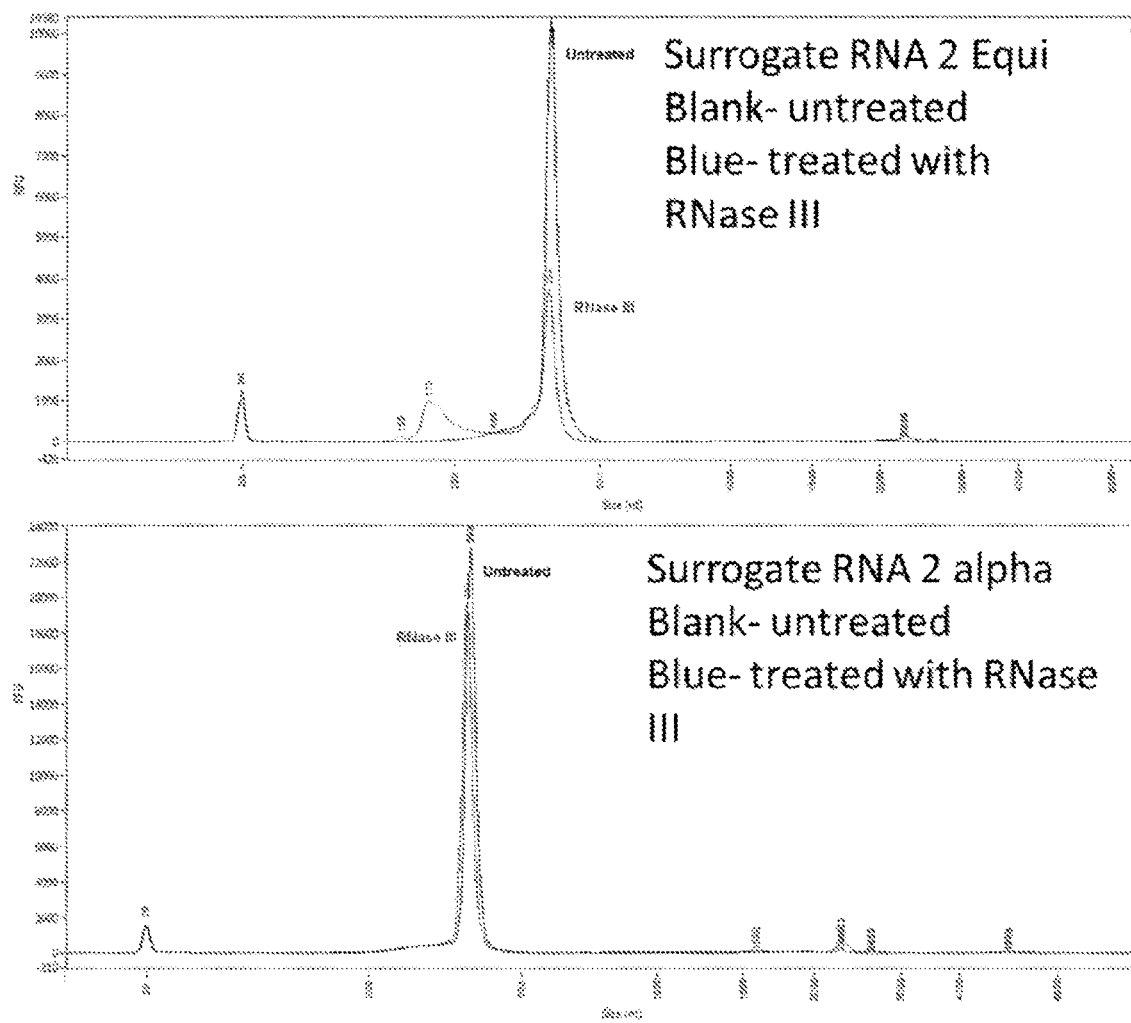
FIG. 7 is a Capillary Electrophoresis analysis of a short transcript transcribed using different processes and treated with RNase III. The data show the effect of model RNAs treated with RNase III.
Figure 8A:
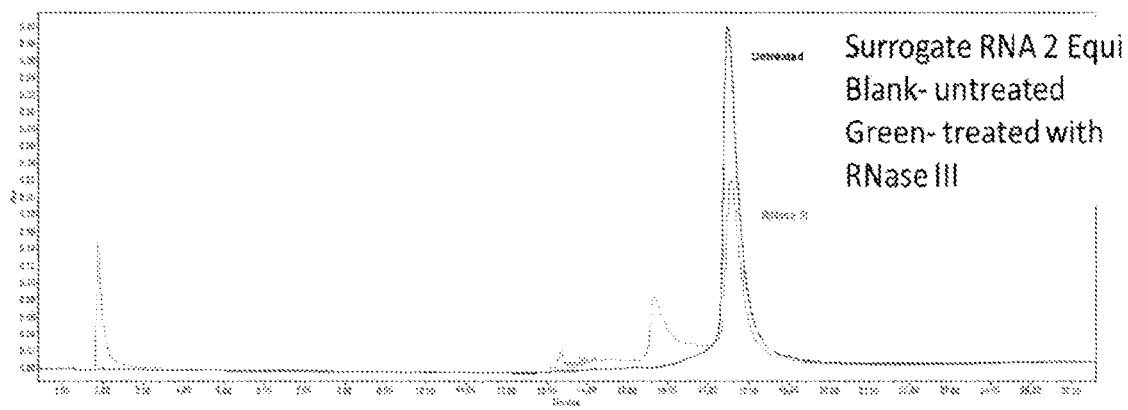
FIGS. 8A and 8B show the results of the RP-IP purity method.
Figure 8B:
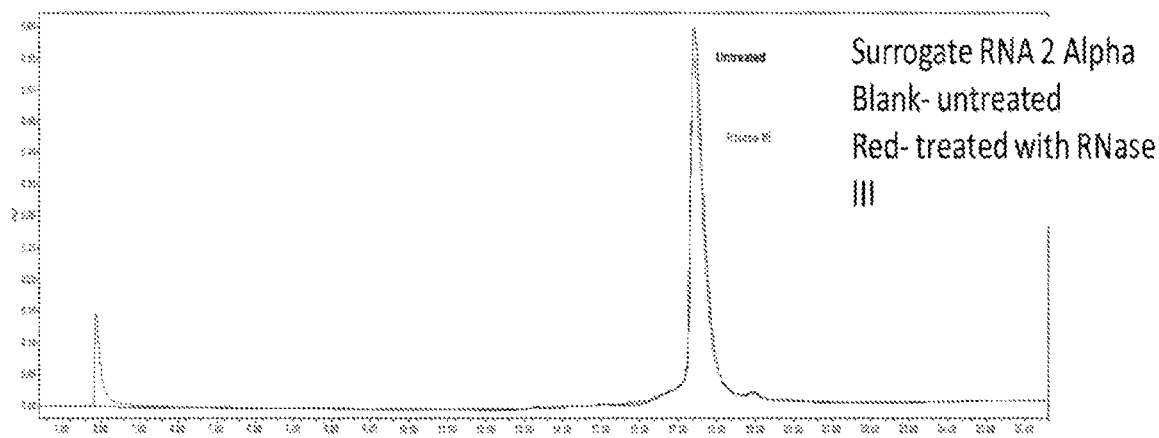
Figure 9:
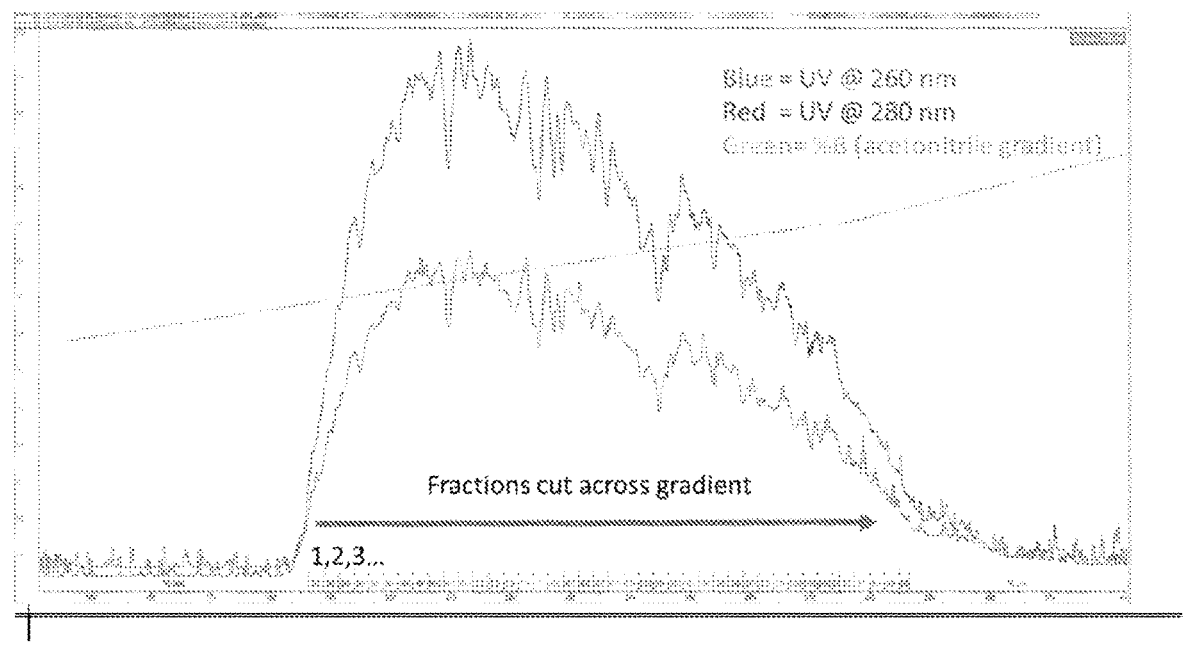
FIG. 9 is a RP Fractionation of hEPO treated with and without RNase III.

A Capillary Electrophoresis analysis of a short transcript transcribed using different processes and treated with RNase III was performed. The inquiry was whether a short, model transcript may be used to characterize the effect of RNase III treatment? Surrogate RNA construct was transcribed using equimolar or alpha processes then treated with RNase III and analyzed by capillary electrophoresis. Equimolar material appeared to contain the most RNase III substrate, while alpha process material did not contain any substrate, according to CE. With RNase III treatment, the model RNA peak shifts 5-7 nucleotides on the fragment analyzer. The equimolar IVT forms a drastic second peak 216 nucleotides shorter than the main peak, which was also observed with the ORF containing mRNA (FIG. 7). Therefore, using model RNAs and LC/MS, one can characterize precisely what component was cut, and by deduction, what component remains. The HPLC purity method showed polyU upon isolation and enrichment of cleavage products (FIG. 9). An RP analysis of RNA Surrogate 2 EQ transcript treated with RNase III (same construct as top figure in FIG. 7 . . . alternative analysis) was performed. Several species were observed by RP analysis after treatment of Surrogate RNA transcript with RNase III. Since this RP method was a tail-selective method, we hypothesize that these early eluting peaks are short oligos and/or tail variants (FIG. 8A). An RP analysis of RNA Surrogate 2 alpha construct transcribed using alpha process transcript treated with RNase III was performed. We did not observe any evolution of additional impurity peaks and appreciable changes to the overall purity in the RP trace for Surrogate RNA alpha material treated with RIII. Thus, we can conclude that alpha process does not make the same dsRNA species as equimolar process (FIG. 8B).

dsRNA Abundance by RNase III and Cytokine Data from RP Fractions

A RP Fractionation of hEPO treated with and without RNase III was performed. hEPO G5 mRNA transcribed via both equimolar and alpha processes were purified by reverse phase HPLC. Fractions were collected across the elution gradient. Fractions were treated with RNase III subsequently analyzed by capillary electrophoresis comparing untreated RNA and RNase III treated (overlaid). The fractions of RNA were also transfected into BJ Fibroblasts and IFN-β induction was assessed pre and post RNase III treatment (FIG. 9).

Figure 10A:
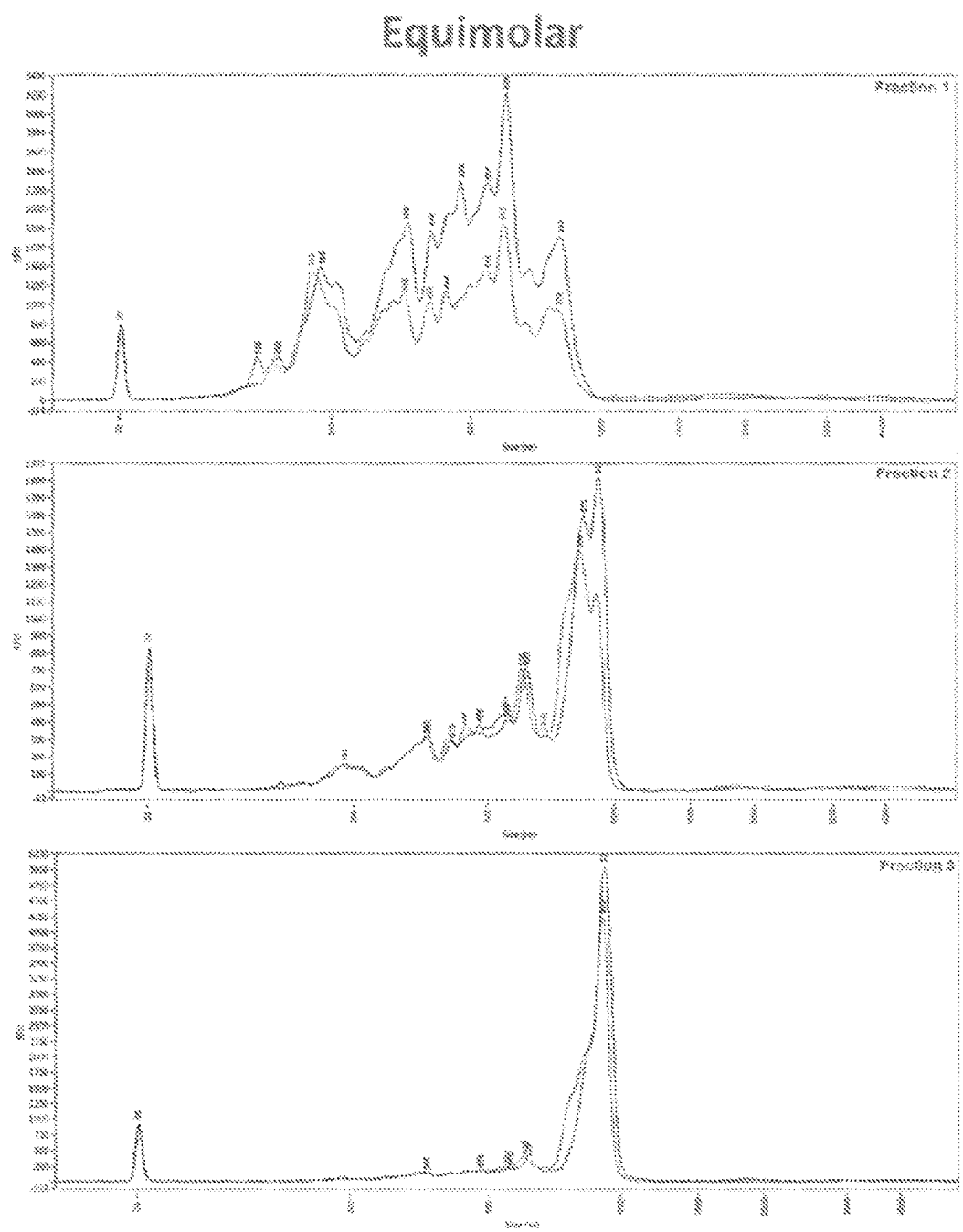
FIGS. 10A-10D show hEPO fraction RNase III fragment analyzer data following equimolar (FIGS. 10A, 10B, and 10C) reactions. The hEPO was modified so that its uridine bases were 1-methylpseudouridine. Treatment with RNase III did not show appreciable purity differences using process with excess GTP. With equimolar there is considerable substrate.
Figure 10B:
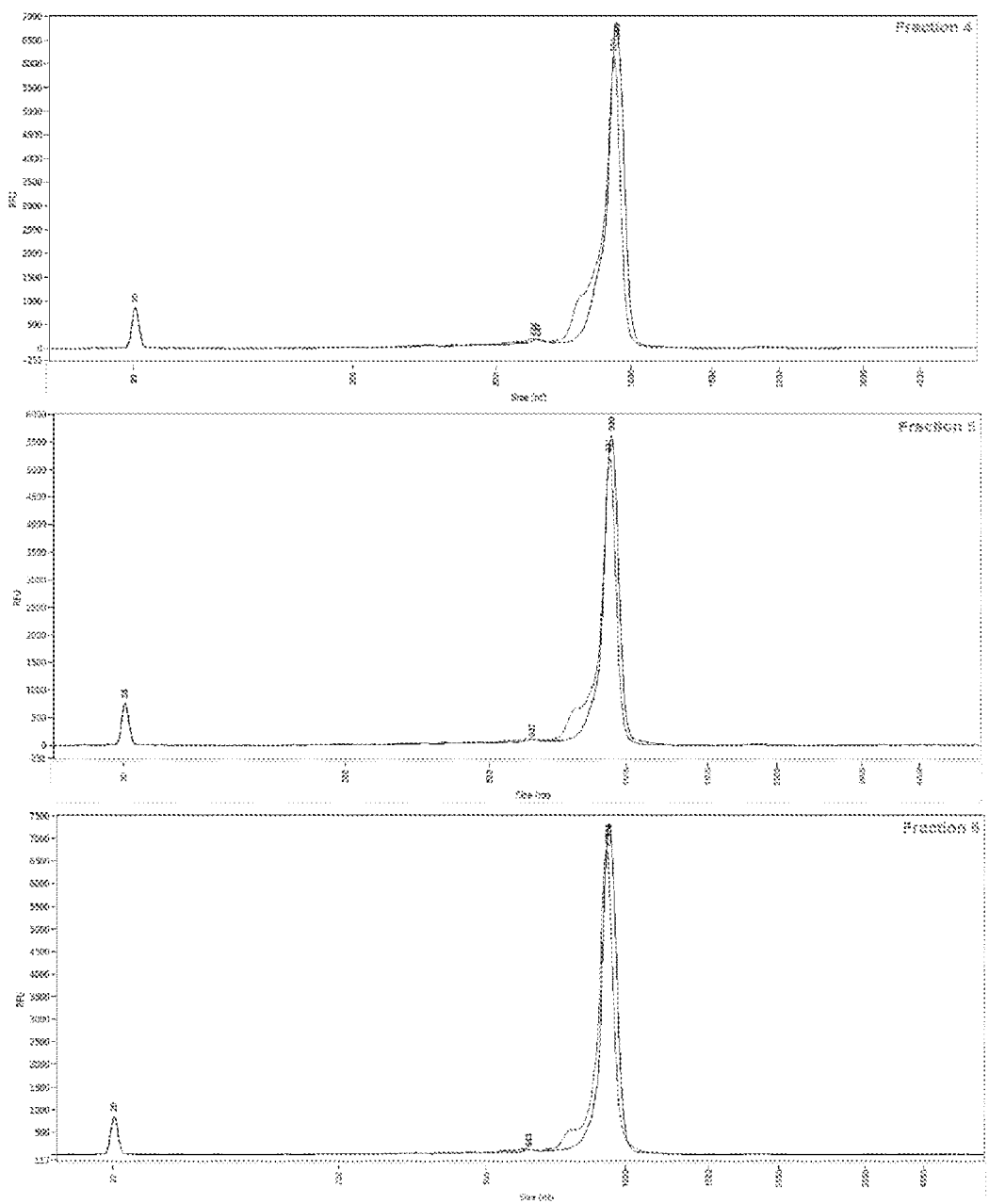
Figure 10C:
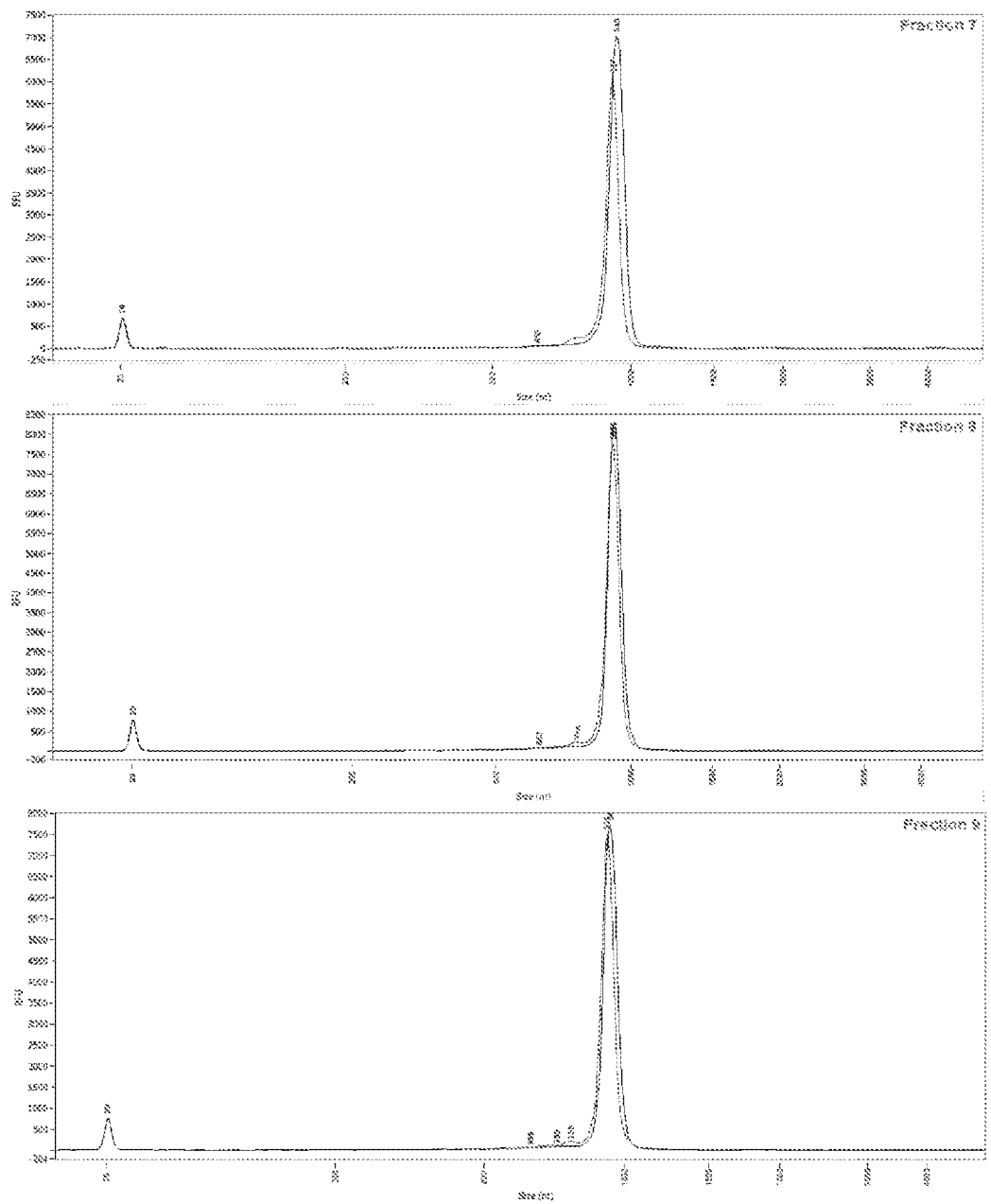
Figure 10D:
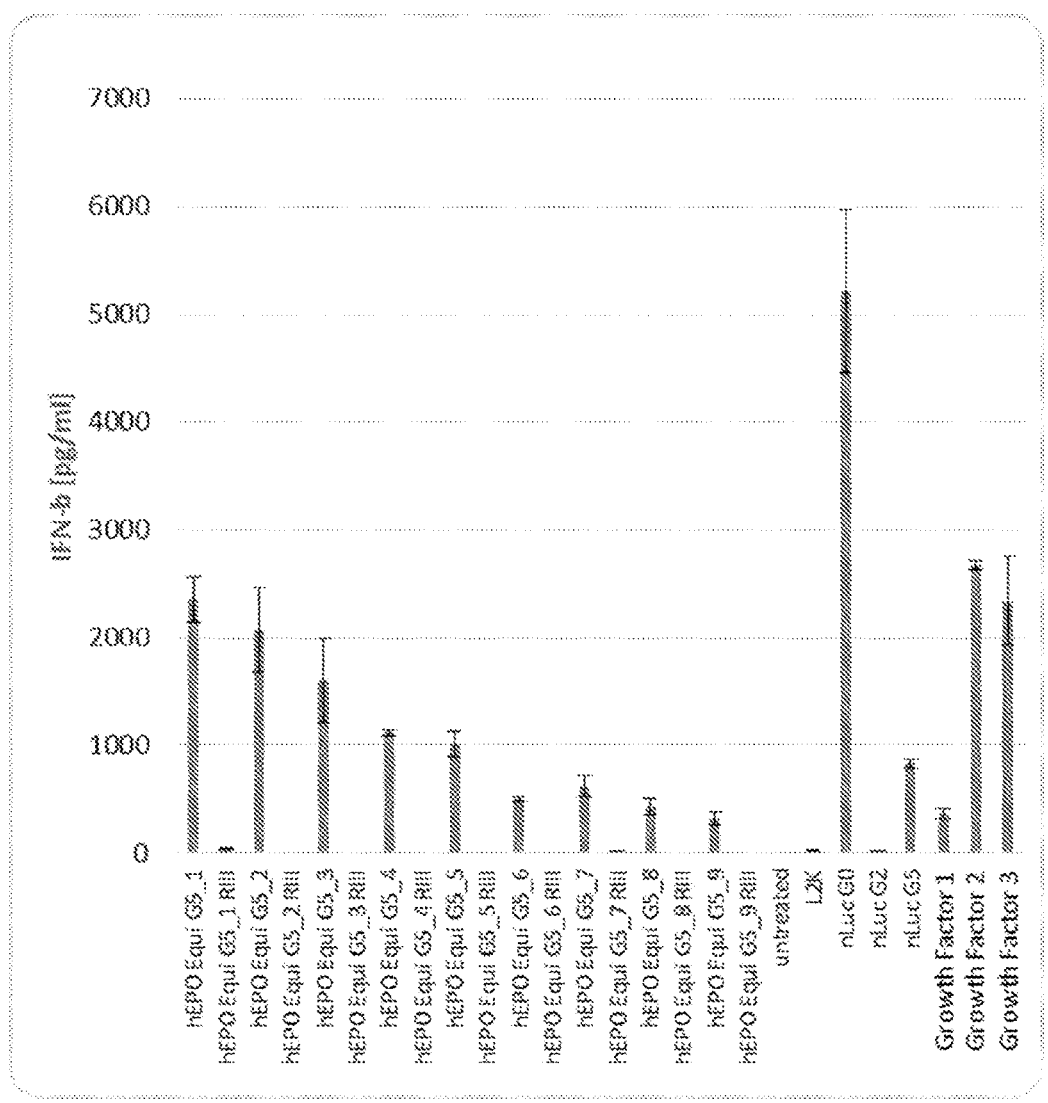

A Capillary Electrophoresis analysis of RP fractionated hEPO EQ +/−RIII treatment was performed. hEPO EQ was treated with RNase III then RP purified, fractionated, and analyzed by CE (blue: RIII treated; black: untreated) Early equimolar fractions (fractions 1-6) containing RNA impurities denote appreciable abundance of dsRNA/RNase III substrate. dsRNA was enriched in early fractions This was confirmed by high INF-B levels. Equimolar fractions 7-9 denote lower levels of dsRNA/RNase III substrate by CE, which was also confirmed by decreasing levels of IFN-β. RNase III treatment of each fraction reduces IFN-β induction to basal levels, which again confirms IFN-β impurities are comprised of dsRNA (FIG. 10A-C). In vitro IFNbeta analysis of hEPO EQ G5 untreated or after RNase III treatment (FIG. 10D).

A Capillary Electrophoresis analysis of RP fractionated hEPO Alpha +/−RIII treatment was performed. hEPO alpha was treated with RNase III then RP purified, fractionated, and analyzed by CE (blue: RIII treated; black: untreated)

Figure 11A:
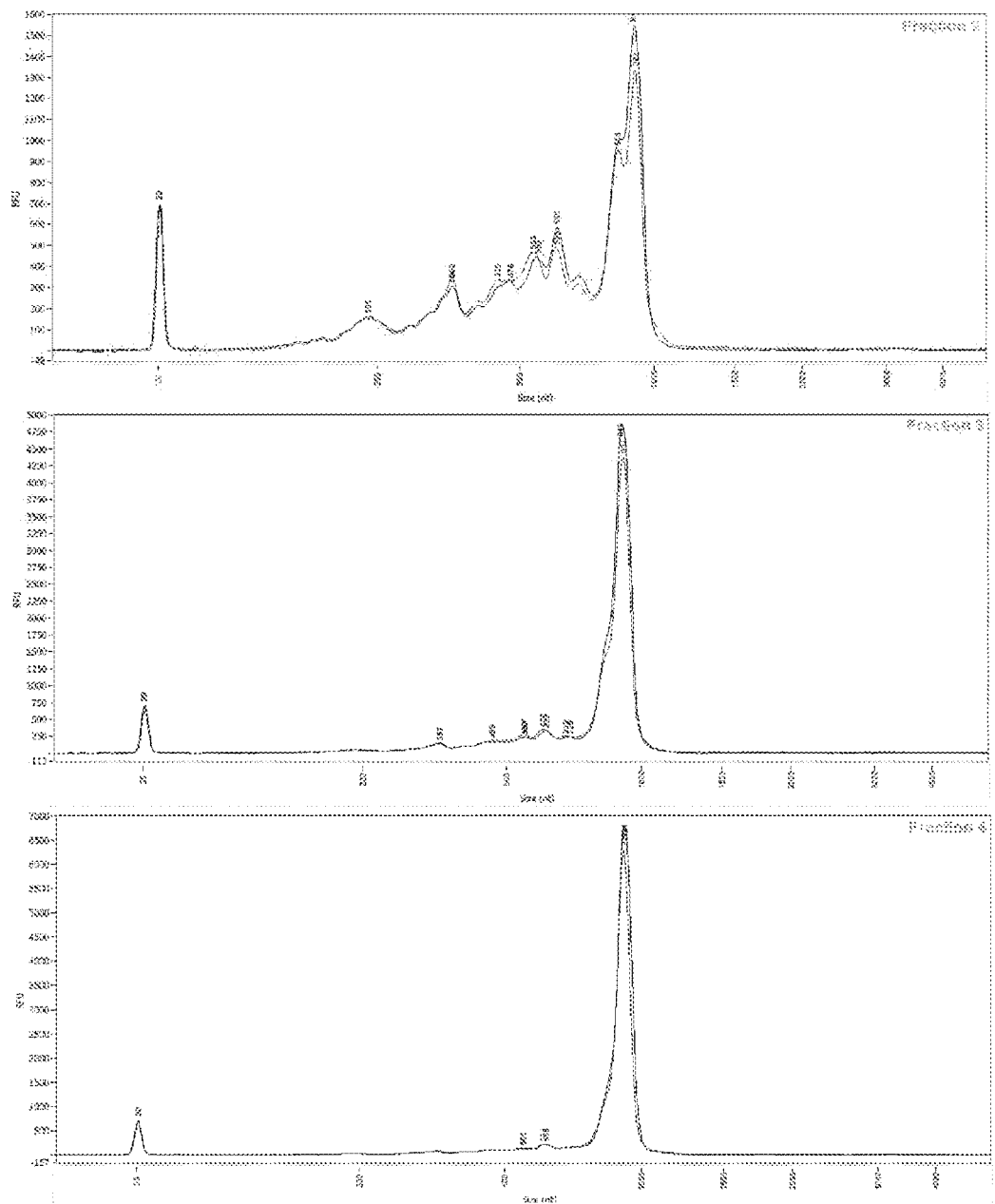
Figure 11B:
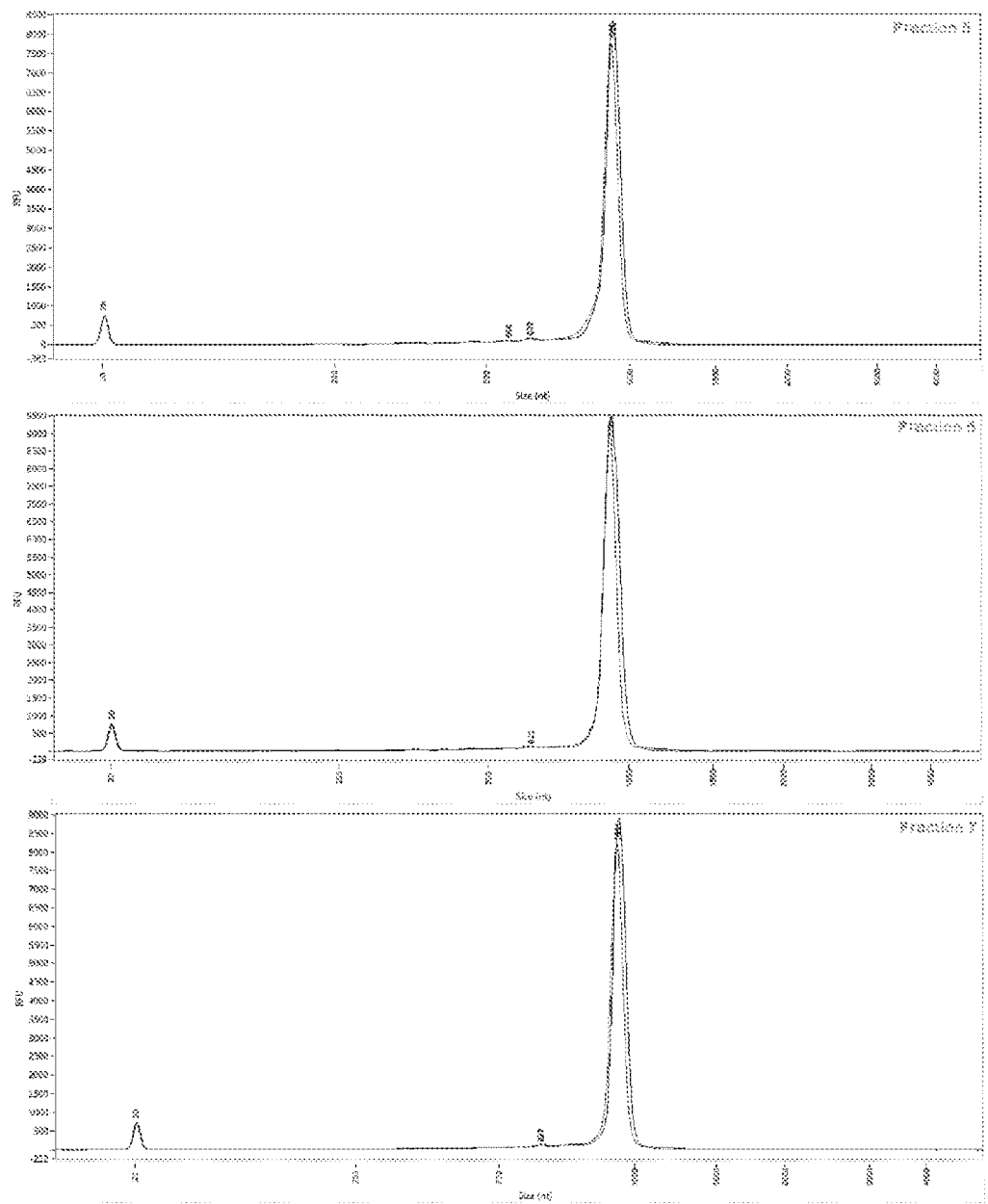
Figure 11C:
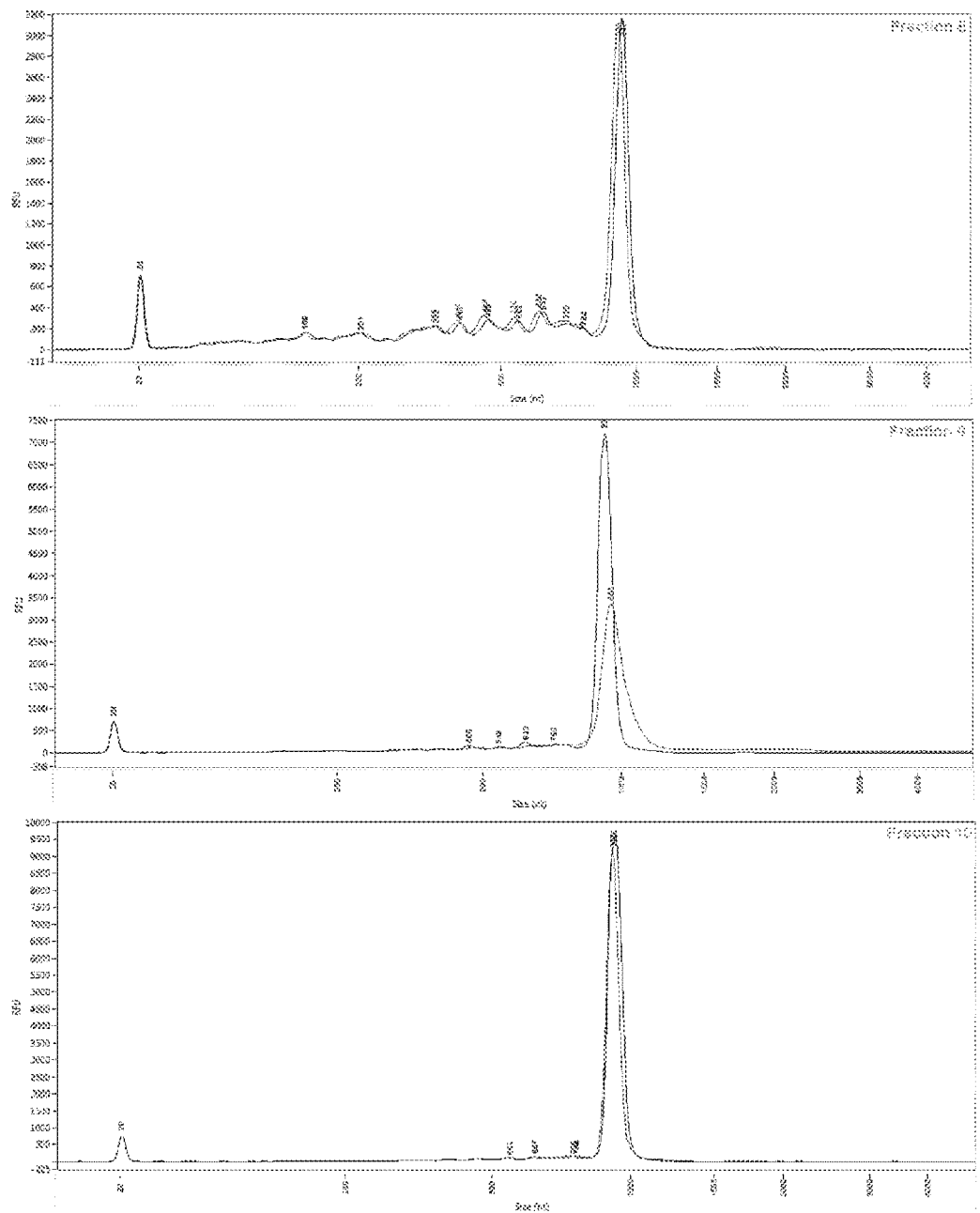
Figure 11C:
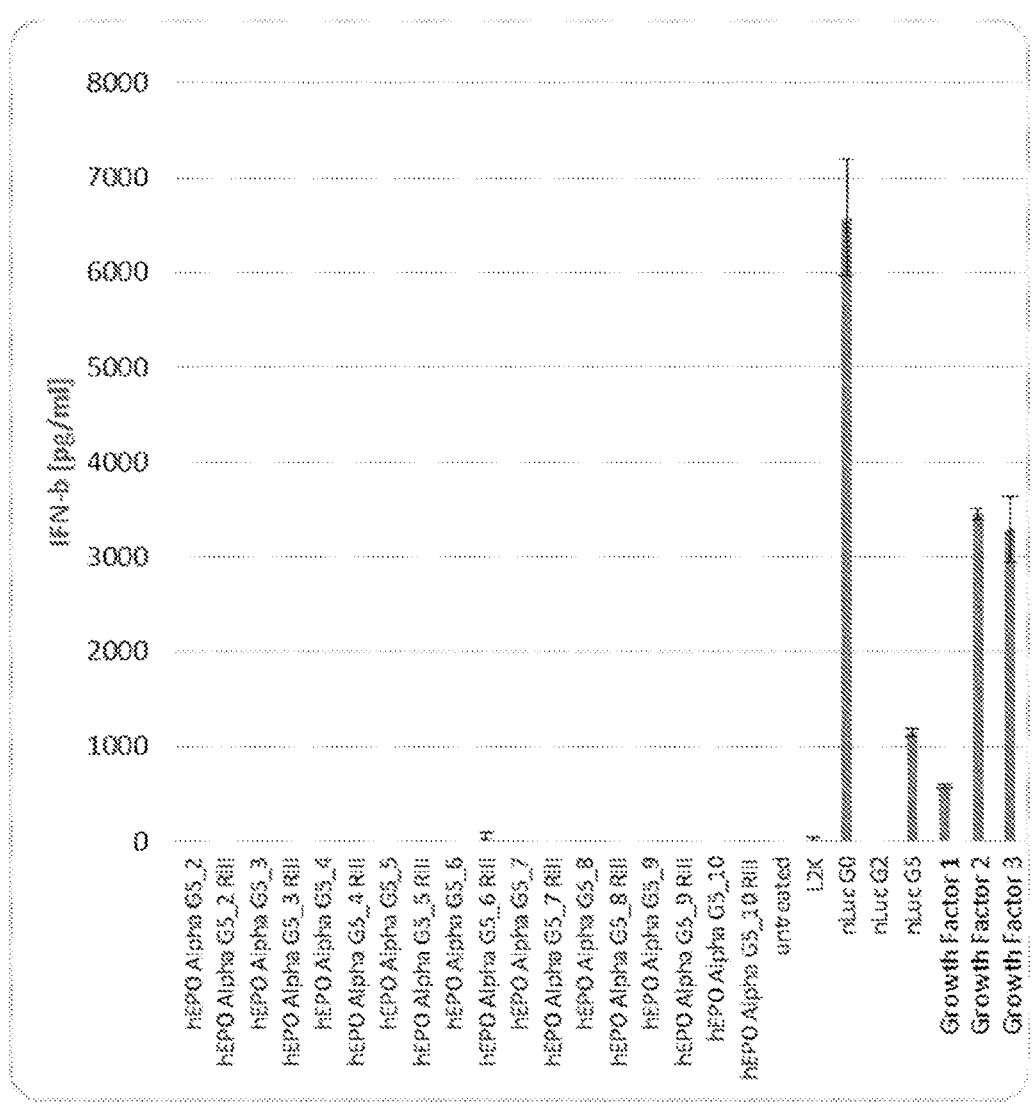

(FIG. 11A-C). In vitro IFNbeta analysis of hEPO Alpha G5 untreated or after RNase III treatment (FIG. 11D). All fractions denote trace levels of dsRNA (RNase III substrate) by both capillary electrophoresis as overlays electropherograms are virtually identical. This was confirmed by basal levels of IFN-β in both treated and untreated fractions. RNA transcribed with alpha process was devoid of dsRNA, despite non-full length/truncated RNA impurities being present in early fractions.

ELISA Detection of dsRNA Abundance

Figure 12:
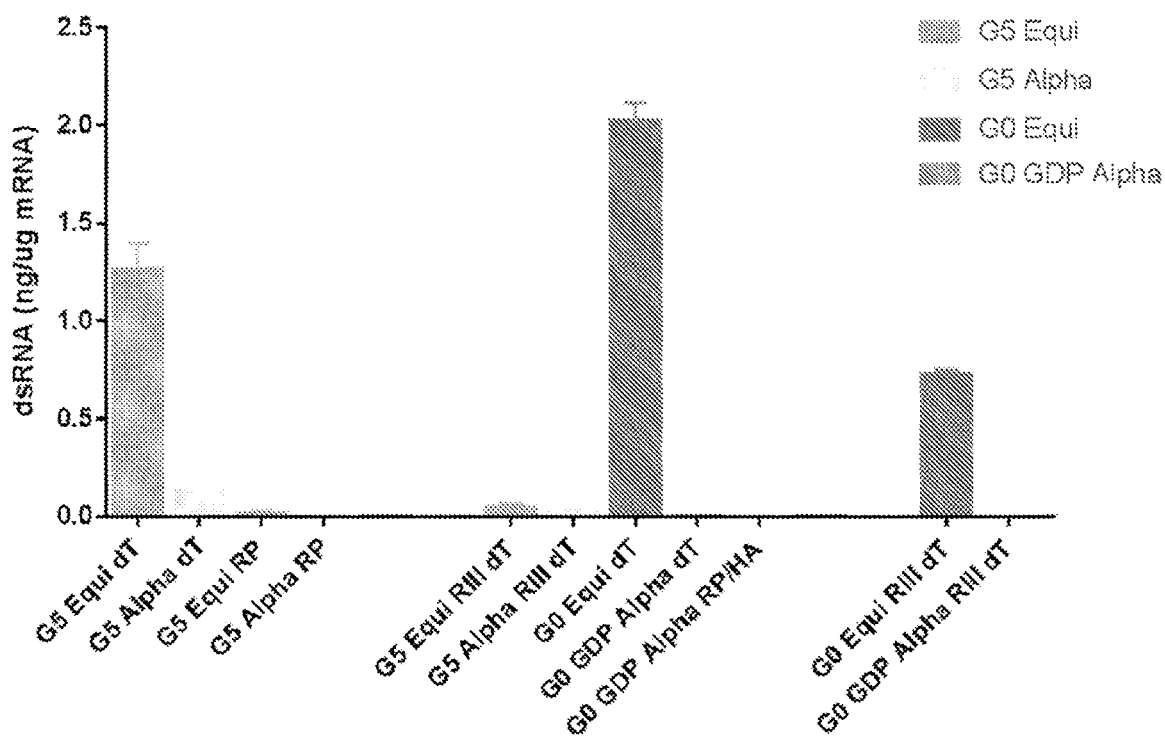
FIG. 12 shows the results of a J2 anti-dsRNA ELISA assay.
Figure 13:
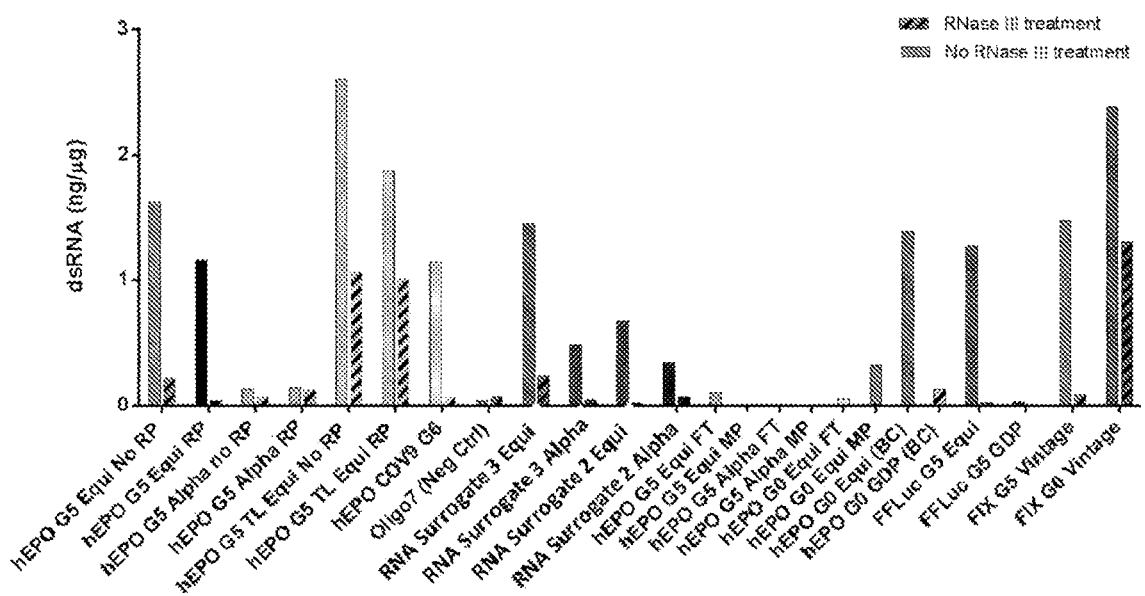
FIG. 13 shows that dsRNA is removed by RNase III treatment.

The J2/K2 dsRNA ELISA was developed to measure dsRNA abundance. Plates were coated with J2 monoclonal (IgG) antibodies and then blocked. The RNA of interest was then added at given concentrations and incubated for an hour. The K2 monoclonal antibody was added (IgM), and an HRP-conjugated anti-IgM goat polyclonal antibody was added. TMB was added to develop the signal. The assay detects duplexes greater than 40 base pairs in length. J2 can assist in RIII endpoint determination. A knockdown of dsRNA was observed with RP or RNase III treatment (FIG. 12). The J2 assay suggests that there was considerably more dsRNA in equimolar material than alpha. The RP process removes dsRNA material from EQ samples, to a similar extent as RIII treatment. The alpha reaction mRNA had less dsRNA in feedstock compared to the equimolar IVT product. Also, a knockdown in dT purified RNase III materials was observed to be greater than TrisRP. The assay also illustrated that dsRNA was removed by RNase III treatment (FIG. 13). While dsRNA levels detected by J2 vary based on construct/process/chemistry, RNase III treatment appears to reduce most dsRNA levels to baseline. LCMS analysis after Nuclease P1 treatment showed additional NTPs present in FFB mRNA, as reverse complements initiated with non-G were present in higher abundance in the equimolar group, as compared to the alpha reaction group (Table 2).

TABLE 2

| | pppA ng/mL | pppG ng/mL | pppC ng/mL | pppU ng/mL |
|---|---|---|---|---|
| G5 hEPO Equimolar uncapped | 31 | 172 | 53 | BQL |
| G5 hEPO Formulation of invention Uncapped | 12 | 159 | BQL | BQL |

Mitigation of RNA Templated Transcription in Low Temperatures IVT's

Figure 14:
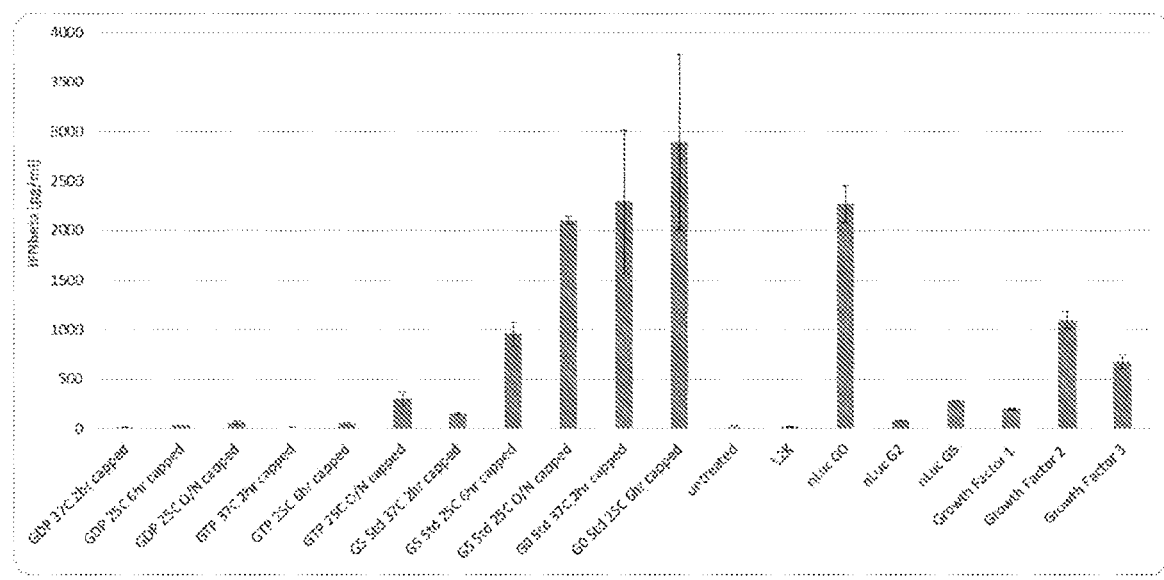
FIG. 14 shows the results of an IVT characterization study, illustrating that the IVT with an excess of GTP is less sensitive to low temperature-induced cytokine spikes.
Figure 15:
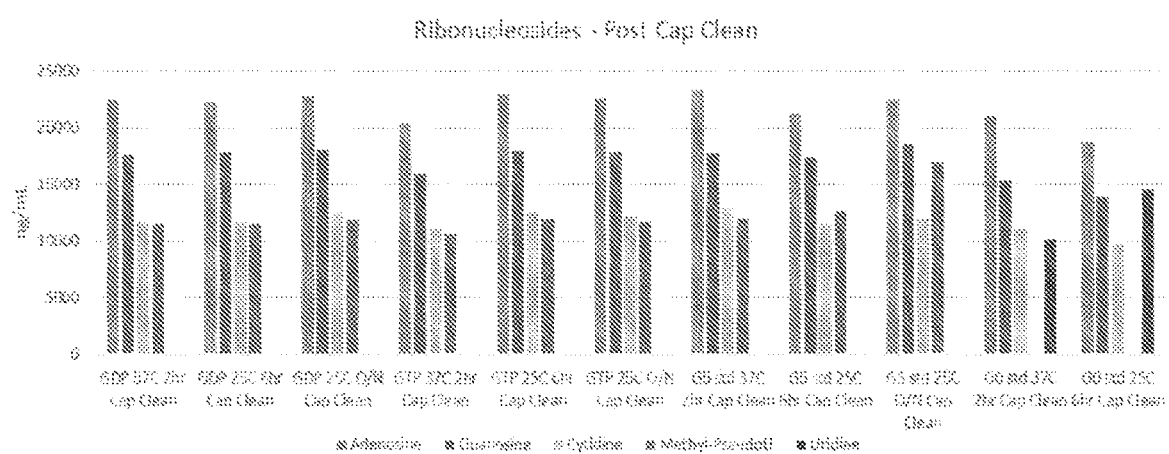
FIG. 15 shows the nuclease P1 results of the IVT characterization study.

An IFNbeta response for hEPO construct prepared using different processes and chemistries was performed. As shown in the IVT characterization study, alpha reaction was less sensitive to low temperature-induced cytokine spikes (FIG. 14). Standard Equimolar IVT when performed at 25 C generate enhanced IFN-β inducing impurity abundance. A Total Nucleotide analysis was performed on hEPO constructs prepared using different processes. Alpha process conditions (GDP and GTP) both mitigate extraneous IFN-β inducing impurity formation when performing IVT at both 37 C and 25 C. Nucleotide distribution was consistent across the control regions in the Nuclease P1 study (grey boxes) and the same hEPO plasmid shows consistent cleavage (FIG. 15). With equimolar IVT processes run at 25 C, abundance of Uridine/1-methyl pseudo U was in higher abundance than at 37 C presumably due to evolution of Poly U, Alpha processes (GDP and GTP) shows consistent nucleotide distribution even at 25 C further supporting mitigation of impurity formation. The differences in bar height are likely due to concentration differences. The U content increased over time with 25° C. standard IVTs. The molar corrected nucleotide composition was given in Tables 3 and 4. G and U are theoretical values, while A and overrepresented and C was underrepresented. There was less deviation across temperature conditions with alpha reaction, and the highest deviation was observed in the U for standard IVTs.

TABLE 3

| | % A | % G | % C | % U |
|---|---|---|---|---|
| GDP 37 C. 2 hr | 35.5 | 27.9 | 18.3 | 18.3 |
| GDP 25 C. 6 hr | 35.2 | 28.1 | 18.4 | 18.2 |
| GDP 25 C. O/N | 34.8 | 27.7 | 19.3 | 18.2 |
| GTP 37 C. 2 hr | 35.2 | 27.5 | 18.9 | 18.4 |
| GTP 25 C. 6 hr | 35.2 | 27.5 | 19.1 | 18.3 |
| GTP 25 C. O/N | 35.1 | 27.7 | 19.0 | 18.2 |
| G5 37 C. 2 hr | 35.4 | 26.8 | 19.5 | 18.3 |
| G5 25 C. 6 hr | 33.8 | 27.7 | 18.3 | 20.1 |
| G5 25 C. O/N | 32.1 | 26.5 | 17.1 | 24.3 |
| G0 37 C. 2 hr | 36.5 | 26.7 | 19.1 | 17.6 |
| G0 25 C. 6 hr | 33.0 | 24.4 | 17.1 | 25.6 |
| Theoretical | 31.7% | 27.3% | 22.4% | 18.6% |

TABLE 4

| | Standard Deviation | | | |
|---|---|---|---|---|
| | A | G | C | U |
| GDP | 0.34 | 0.23 | 0.53 | 0.04 |
| GTP | 0.07 | 0.15 | 0.06 | 0.09 |
| G5 Std | 1.66 | 0.60 | 1.20 | 3.08 |
| G0 Std | 2.53 | 1.65 | 1.43 | 5.61 |

"Forced" RNA Templated Transcription

Figure 16A:
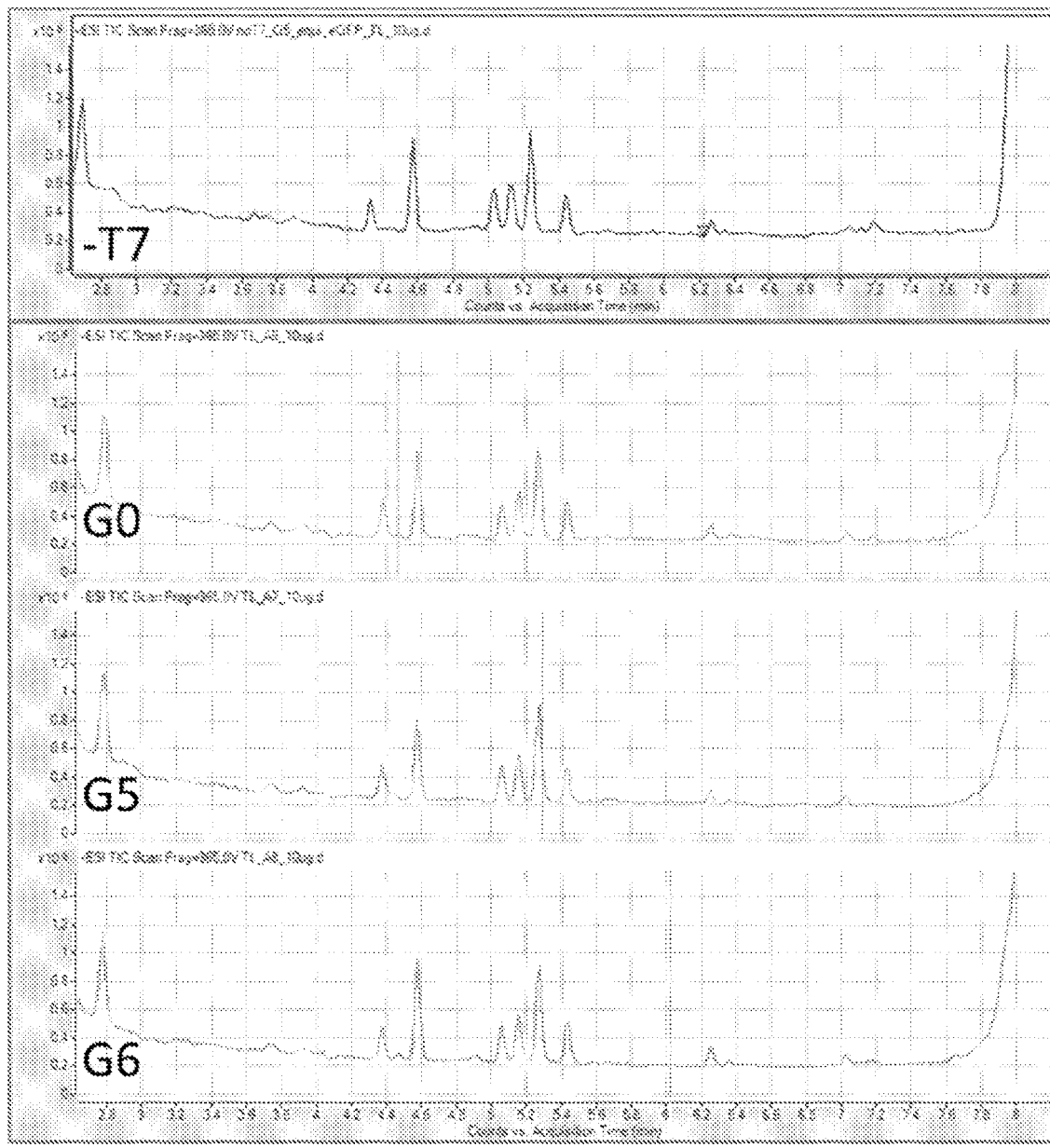
FIGS. 16A to 16B show an impurity analysis by LCMS of RNA-based IVT in different chemistries using G5 in Equimolar process (FIG. 16A) and alpha process (FIG. 16B).

An impurity analysis was performed by LCMS of RNA-based IVT in different chemistries using G5 eGFP EQ. IVTs were set up (in different chemistries) using 4 mg/mL eGFP G5 equi RNA and no DNA template. polyU species are generated from RNA-templated transcription. RNA-templated transcription occurs independent of chemistry. Reverse phase purified eGFP G5 (cold) was incubated at 4 mg/mL (consistent with a typical yield of an in vitro transcription reaction), with all the IVT components except DNA template, which was determined to be below threshold required for in vitro transcription by qPCR, to explore the RNA-templated transcription phenomenon. The materials were analyzed by LC/MS (FIG. 16A (Equimolar process), 16B (alpha process)).

Figure 16B:
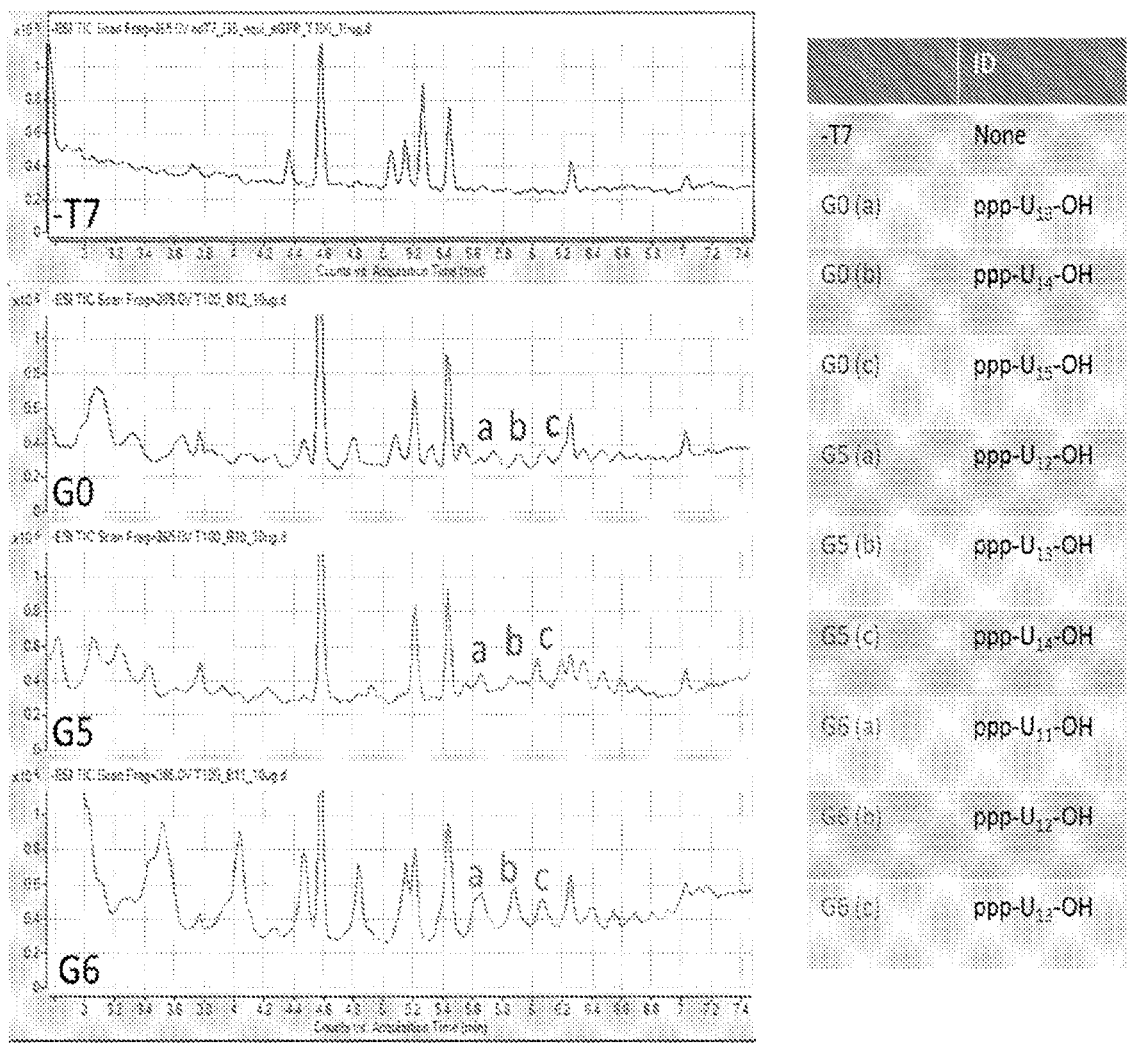
Figure 17:
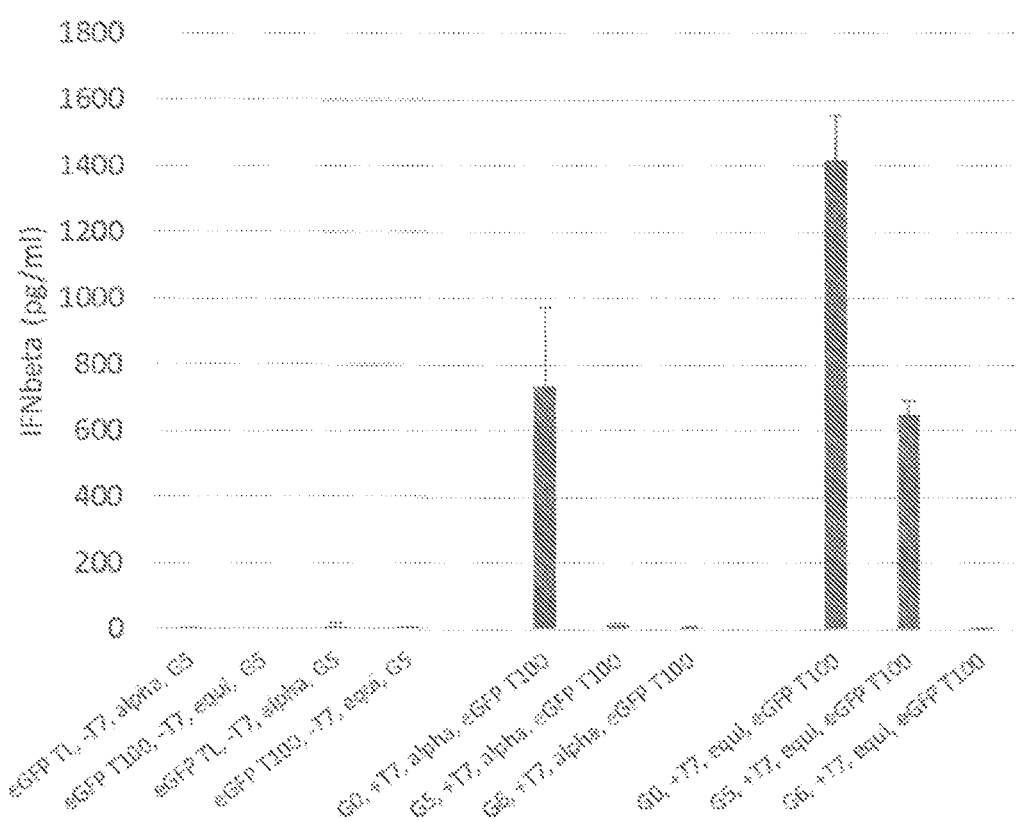
FIG. 17 shows IFN-β in BJ fibroblasts under the different IVT conditions.

A IFNbeta analysis for RNA-templated IVT products was performed. Material was from FIG. 16. After RNA-based IVT, samples were analyzed in vitro to determine if there was a correlation between LCMS analysis (polyU species) and IFNbeta response. Alpha (A100) RNA-based IVTs produce material that has a lower CK response than equimolar material. (G0 or G5); Suggestive again that alpha process mitigates the formation of RNA templated transcription products. All G6 was cold; (intrinsically cold despite formation of impurities) (FIG. 17).

Figure 18:
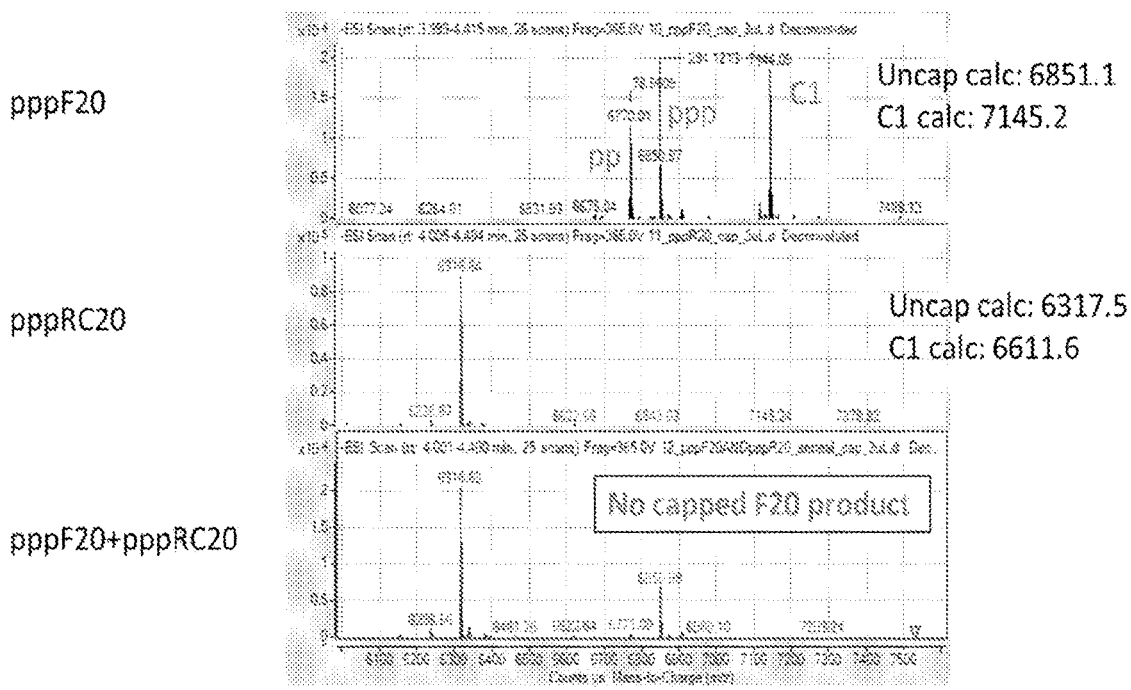
FIG. 18 shows that dsRNA cannot be capped by vaccinia.

A dsRNA cannot be capped by vaccinia was performed to determine whether dsRNA can be capped. Forward and reverse complement oligos both with 5' triphosphates were annealed then were subjected to capping process using vaccinia to determine whether dsRNA could be capped.

pppF oligo (contains 5'pppG) can be capped to cap1 using vaccinia. pppRC oligo (contains 5'pppU) cannot be capped using vaccinia. dsRNA with pppF+pppRC cannot be capped using vaccinia (FIG. 18).

Figure 19:
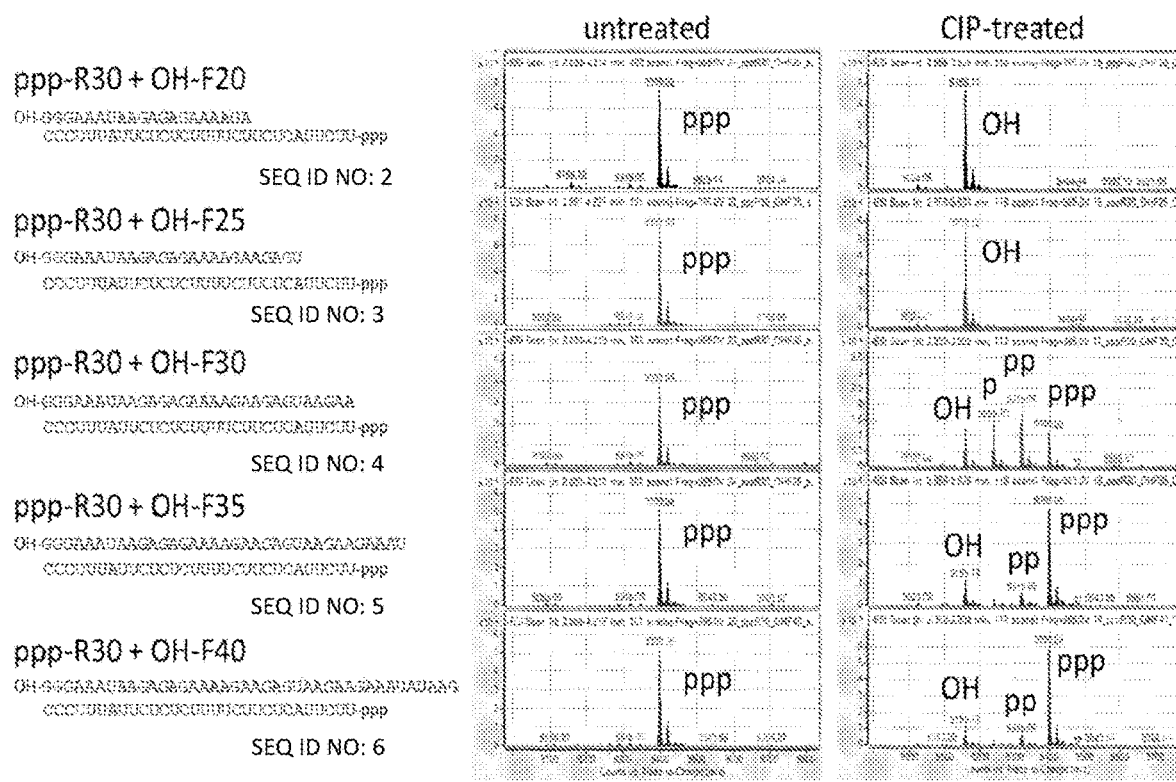
FIG. 19 shows the effects of OP treatment on different dsRNA species.

A Dephosphorylation of dsRNA using CIP was performed to determine if calf intestinal phosphatase dephosphorylate dsRNA with different 5'/3' overhangs? Various F and RC oligos were annealed then treated with CIP and analyzed by LCMS for dephosphorylation efficiency. dsRNA with 5' overhangs can be fully dephosphorylated. perfect duplex dsRNA can be partially dephosphorylated. dsRNA with 3' overhangs cannot be fully dephosphorylated. This demonstrates why phosphatase was not 100% effective at reducing CK response (FIG. 19).

Figure 20:
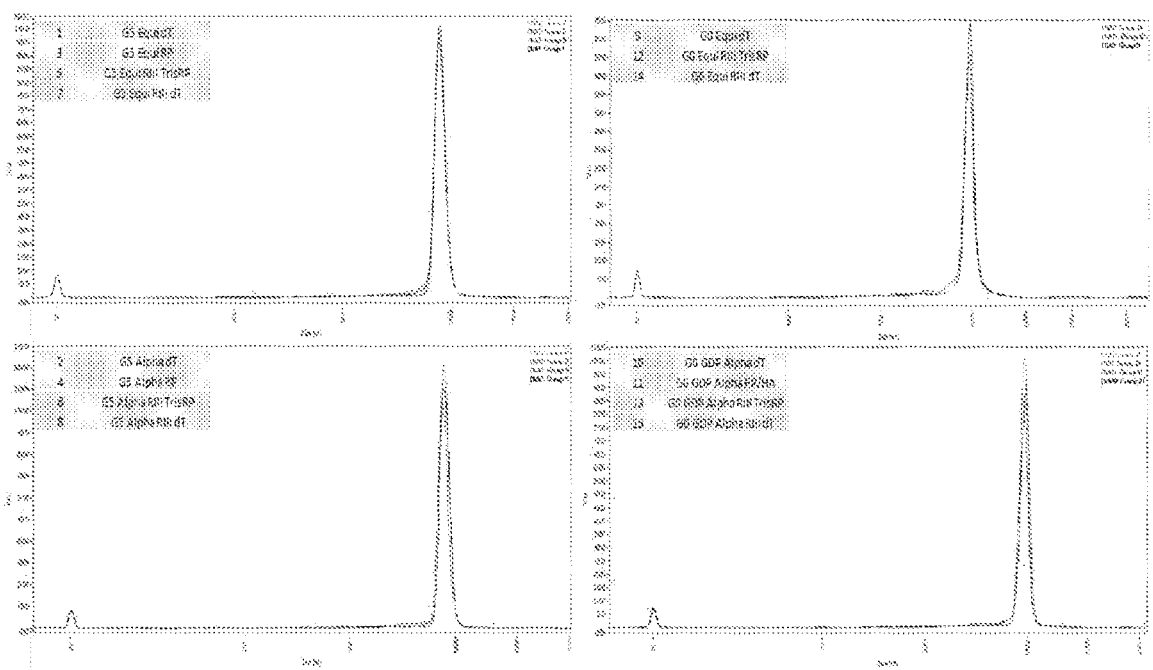
FIG. 20 shows FA purity data from the in vivo experiments.

A CE Purity of mRNAs dosed in aforementioned in vivo study denoted in electropherograms was performed. (FIG. 20). Structure may play a role, as the 5'UTR may impact the effectiveness of alpha reaction (FIG. 20).

In Vivo Studies

RIII treatment showed distinct cytokine knockdown in mice, both with unmodified and completely modified (all uridine was 1-methylpseudouridine,) species. It may be used as a standalone method to knockdown cytokines to near basal levels. Female mice (n=5 per group) were injected once with 0.5 mg/kg of selected test materials.

Figure 21:
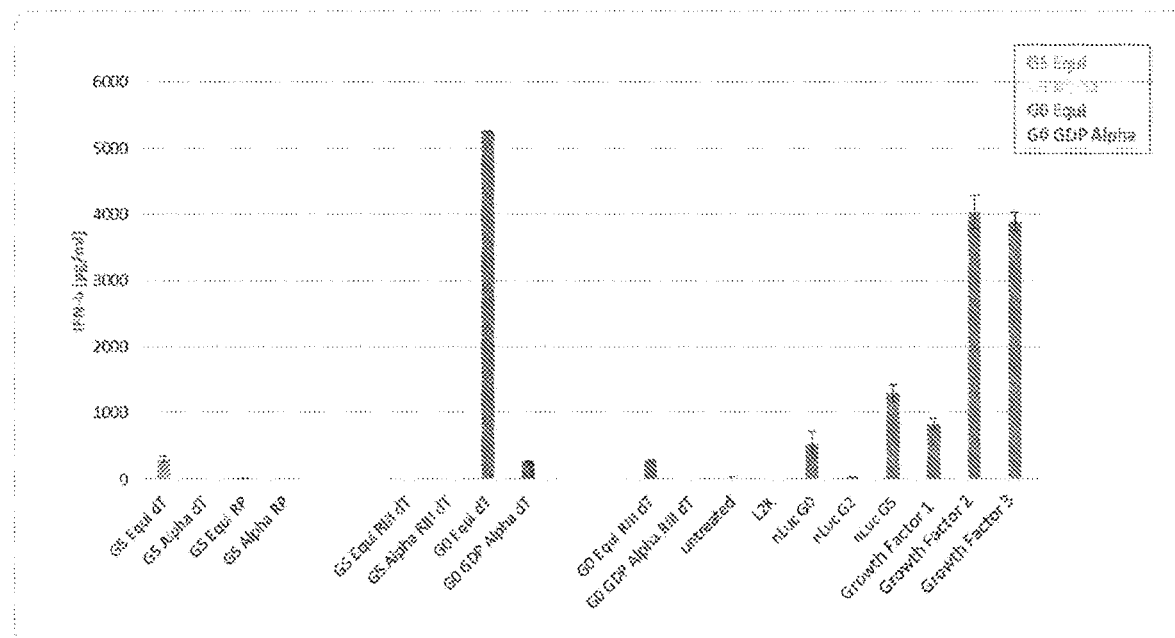
FIG. 21 shows IFN-β induction in BJ fibroblasts.

An IFNbeta analysis of G0 and G5 hEPO mRNA transcribed using different IVT processes and purification permutations was performed to determine what the IFNbeta response for material generated with different chemistries, processes, and treatments (in vitro; BJ Fibroblasts). +RIII, +RP, and alpha processes have similar effects (reduction) on IFNbeta response in vitro in G5. G0 demonstrates that alpha +RIII was superior to equi +RIII (FIG. 21).

Figure 22:
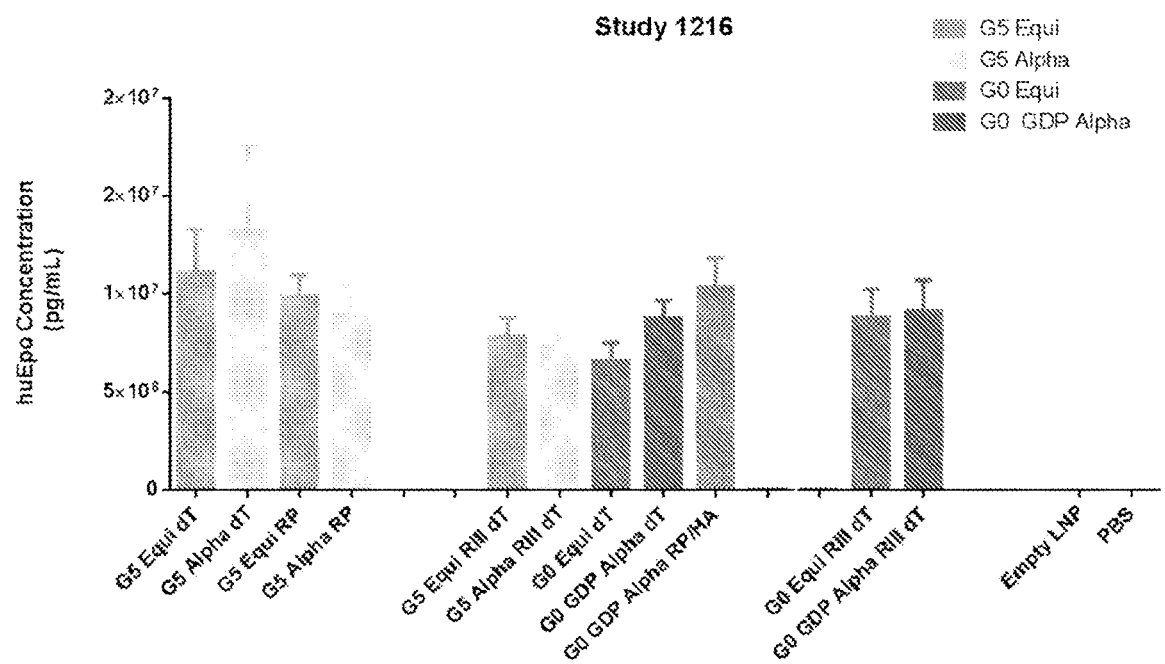
FIG. 22 shows in vivo expression of hEPO.
Figure 23A:
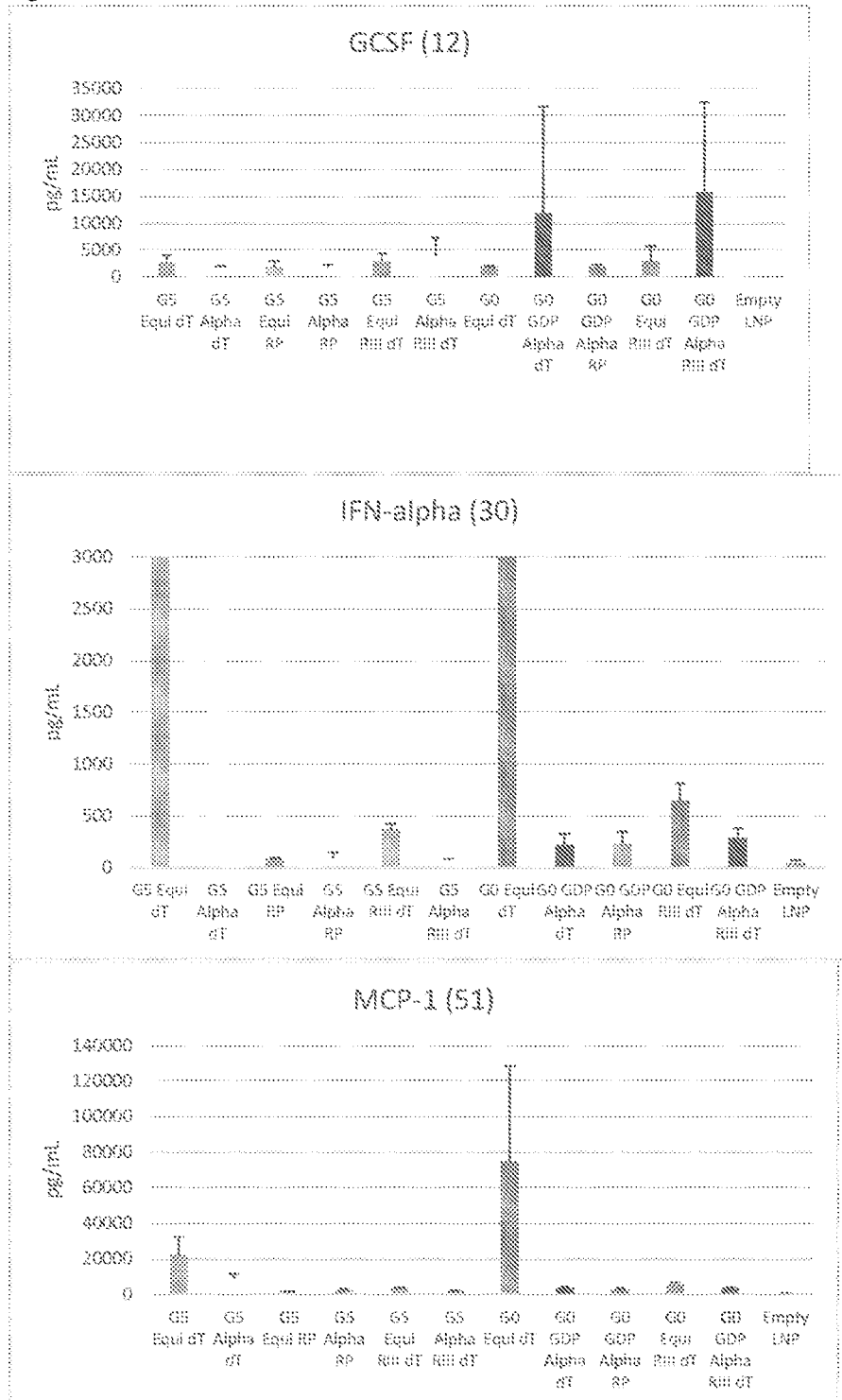
FIGS. 23A to 23D show cytokine Luminex data from the in vivo experiments.
Figure 23B:
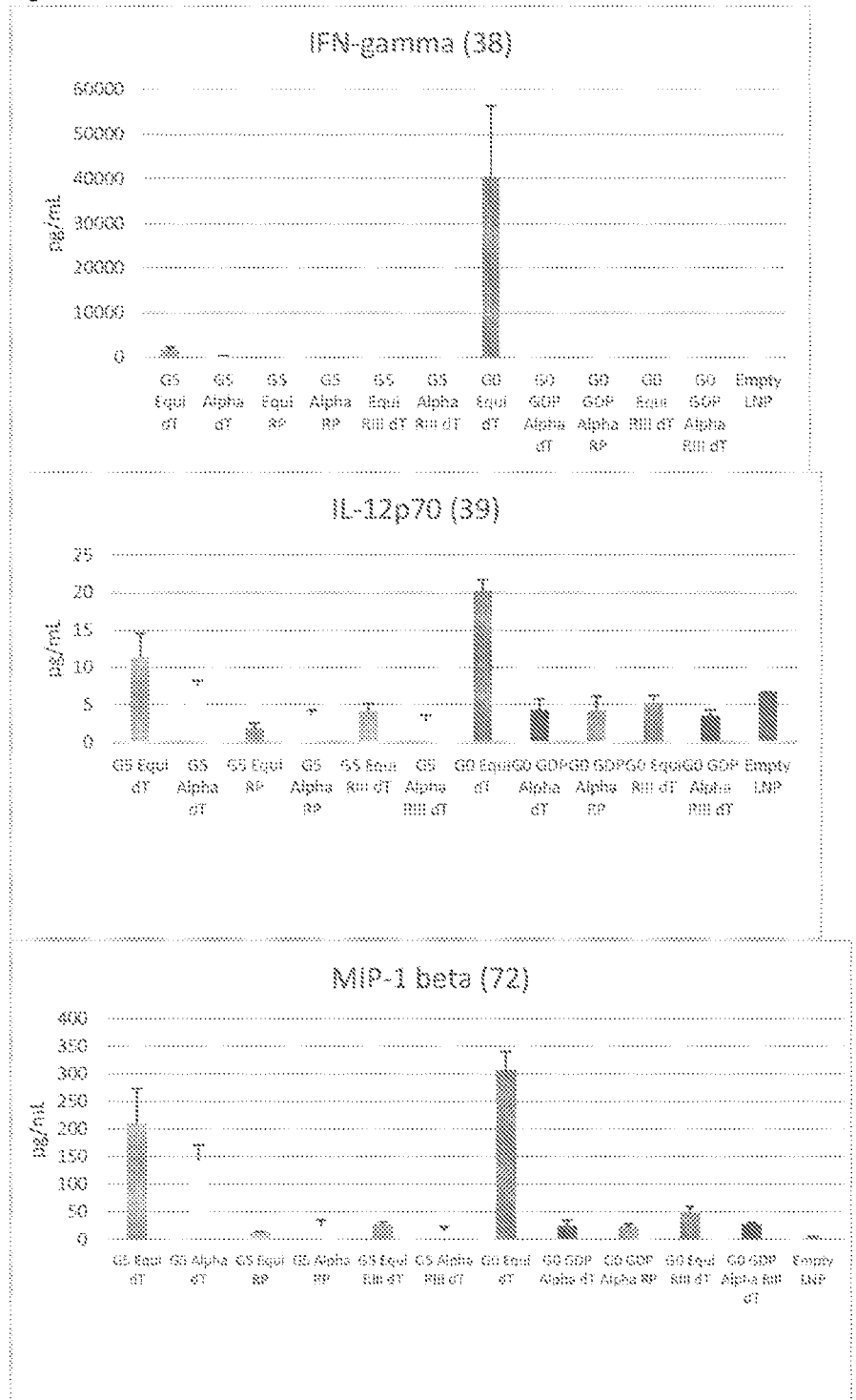
Figure 23C:
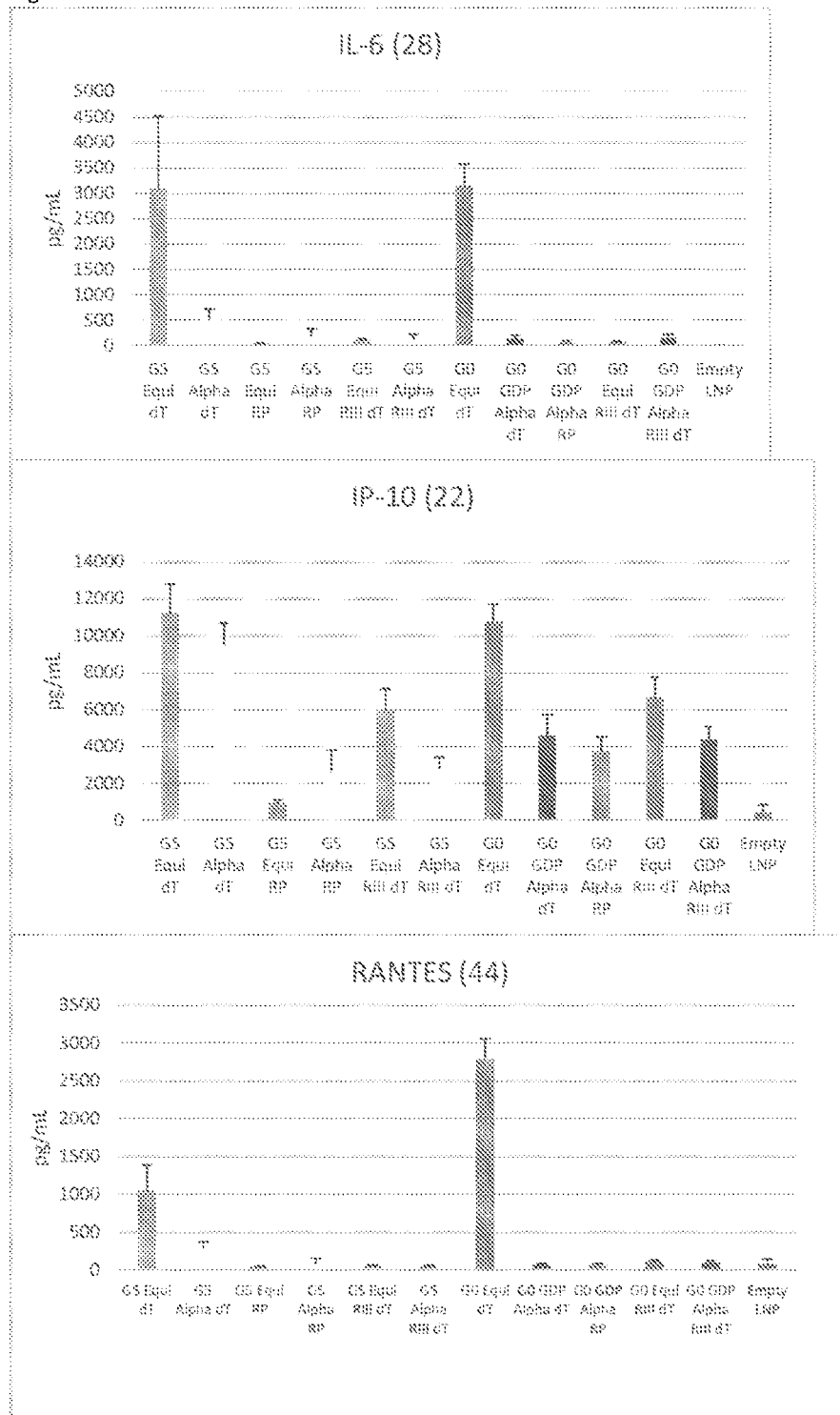
Figure 23D:
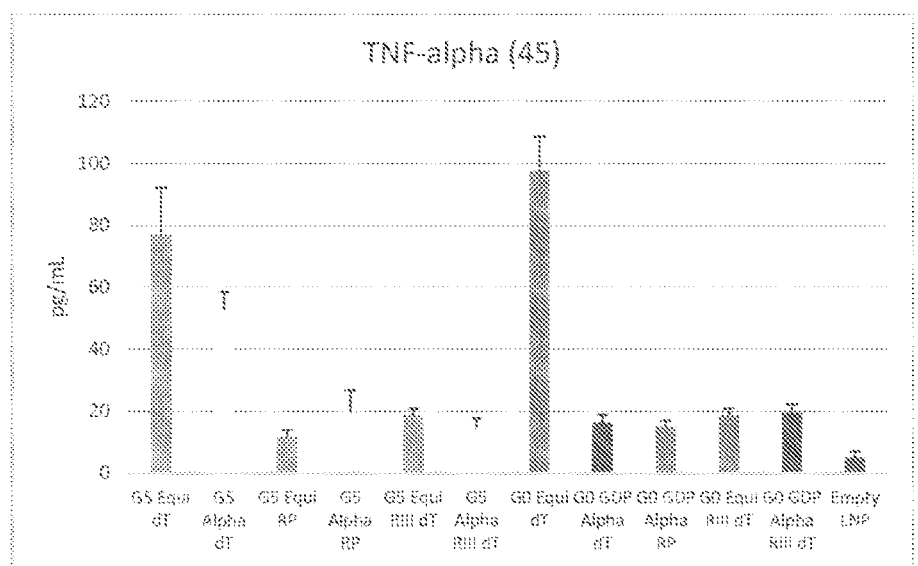

An In vivo (Balb-C mice) expression of hEPO prepared using G0 or G5 chemistries, equimolar or alpha processes, and RNase III treatment via ELISA was performed to determine how expression affected by hEPO prepared using various processes (chemistry, IVT process, RIII treatment). Same material as FIG. 12, 20, 21, 22. There are no significant differences in hEPO expression using RNA generated by different processes (FIG. 22).

A Cytokine (luminex) panel for in vivo (Balb-C mice) G0 and G5 hEPO mRNA transcribed using different IVT processes and purification permutations with and without RNase III treatment was performed to determine with the same material as FIG. 12, 20, 21, 22. Cytokine analysis after treatment of Balb-C mice with 0.5 mpk formulated RNA. Untreated alpha material has a similar CK response as EQ material (G5) in IP10. Alpha process in conjunction with RNase III treatment overall appears to confer less. immunostimulatory activity than the equimolar comparator (+RNase III), especially in G0. RIII treatment reduces CK response (FIG. 23A-23D).

Figure 24:
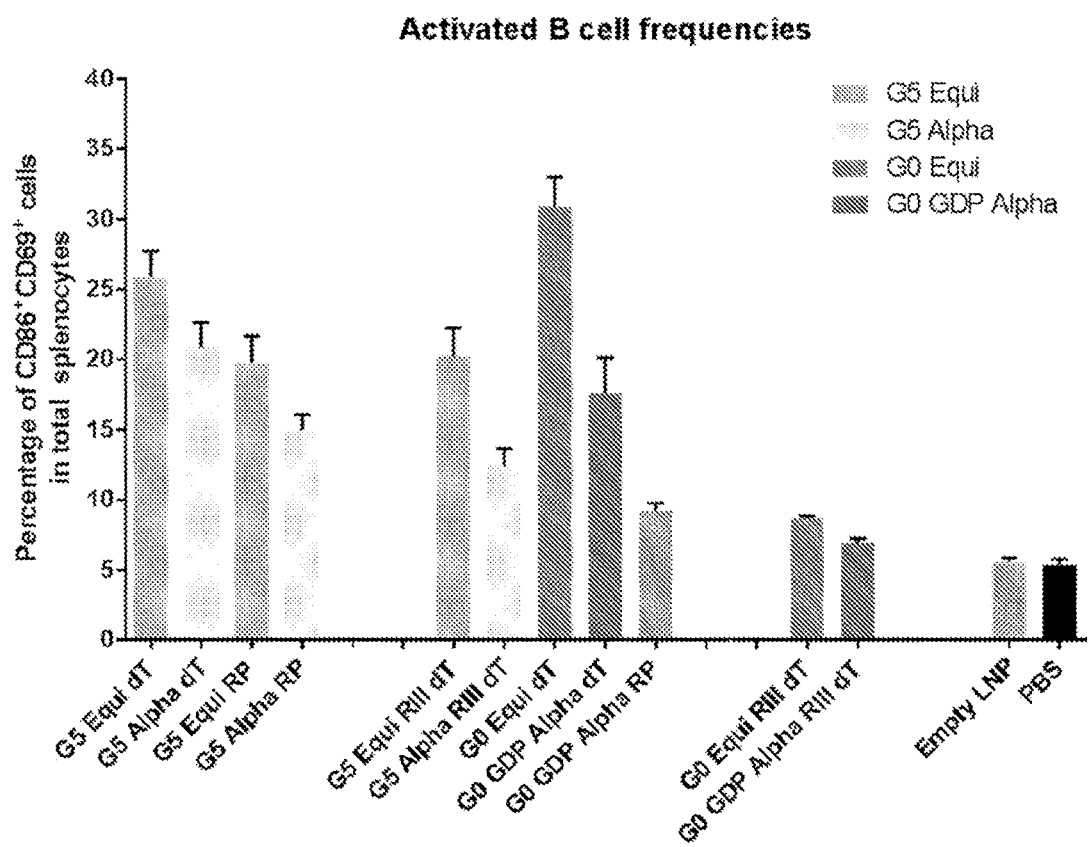
FIG. 24 shows in vivo B-cell activation frequencies.

A B cell activation from spleens of Balb-C mice treated with hEPO prepared using G0 or G5 chemistries, equimolar or alpha processes, and RNase III treatment was performed, Activated B cells (CD86+ CD69+) were analyzed for their response after treatment with hEPO prepared using various processes. B cell activation roughly correlates to cytokine (luminex) panel. RIII treatment reduces the CK response, with respect to the untreated controls (FIG. 24).

An In vitro analysis of short 5' triphosphorylated oligos was performed to determine whether short 5' triphosphorylated oligos stimulate an IFNbeta response in vitro (BJF, IFNbeta). ssRNA and dsRNA <12 nucleotides or base-pairs do not stimulate IFNbeta in BJFs (FIG. 25).

Figure 26:
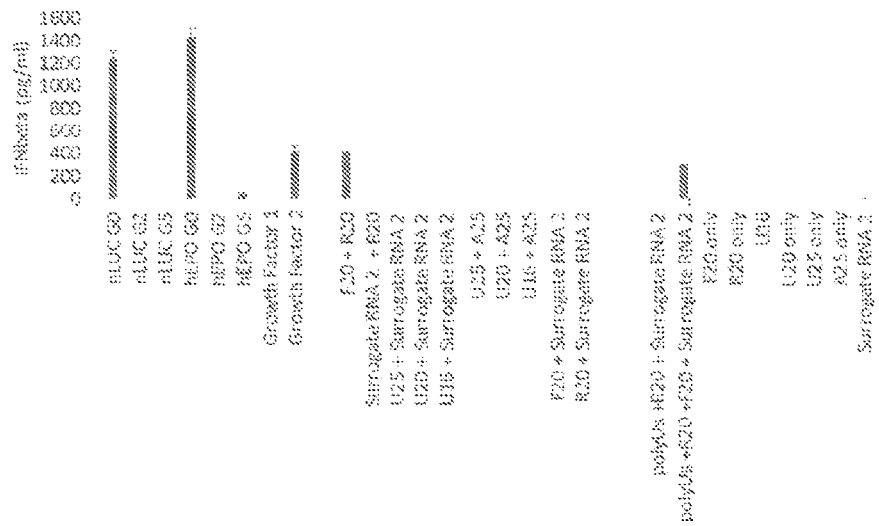
FIG. 26 shows the results of an IFN-β assay, analyzing 20mer and polyU/A dsRNAs.

An In vitro analysis of polyU and dsRNA standards was performed to determine whether using 5' triphosphorylated oligo standards, what stimulates an IFNbeta response in BJFs. pppF+pppRC dsRNA >20 bp was immunostimulatory. 5' triphosphorylated polyU was not immunostimulatory as ssRNA or dsRNA <25 nt or bp (FIG. 26).

Figure 27:
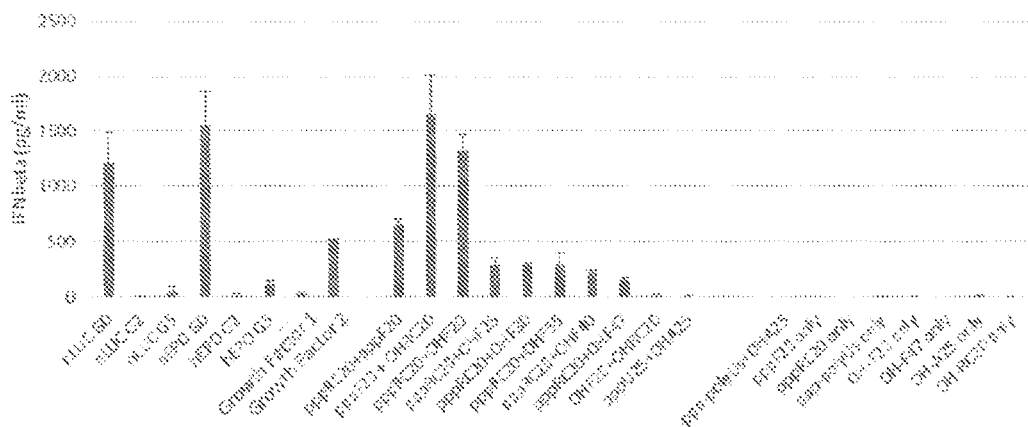
FIG. 27 shows an analysis of 3' overhang with respect to IFN-β response.

An In vitro analysis of dsRNA standards with 3' overhang was performed to determine whether there a 3' overhang length dependence on IFNbeta response for dsRNA standards. The longer the 3' overhang, the lower the IFNbeta response (FIG. 27).

Figure 28:
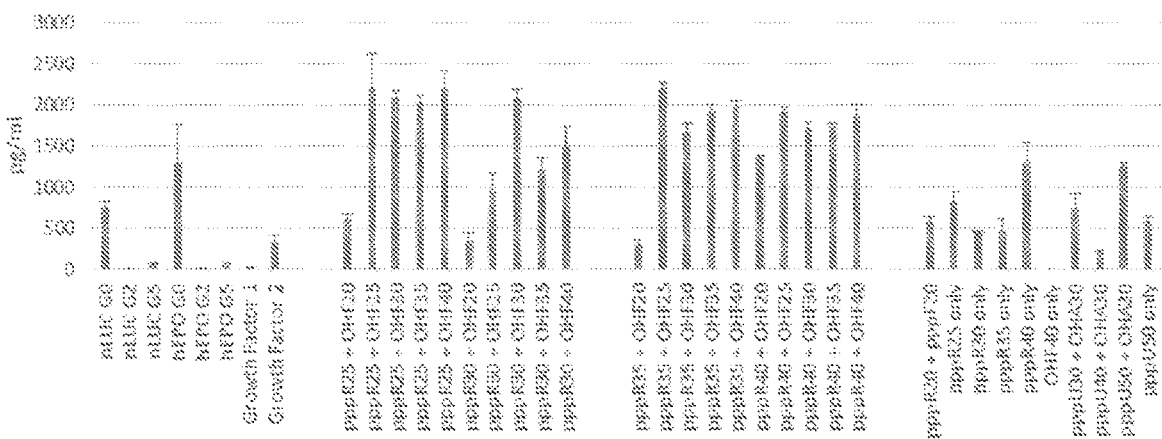
FIG. 28 shows the results of a cytokine assay testing dsRNA standards with 5' overhang, perfect duplex, and 3' overhang of varying lengths.

An In vitro analysis of dsRNA standards with 5' overhang, perfect duplex, and 3' overhang of varying lengths was performed to determine whether an overhang length/identity dependence on IFNbeta response. ssRNA pppRC oligos are hot. dsRNA with 5' overhang (and ~20 bp duplex) are less immunostimulatory than perfect duplex. dsRNA with 3' overhang have equivalent or less immunostimulation than perfect duplex. The longer the dsRNA duplex, the higher the CK response (FIG. 28).

Figure 29:
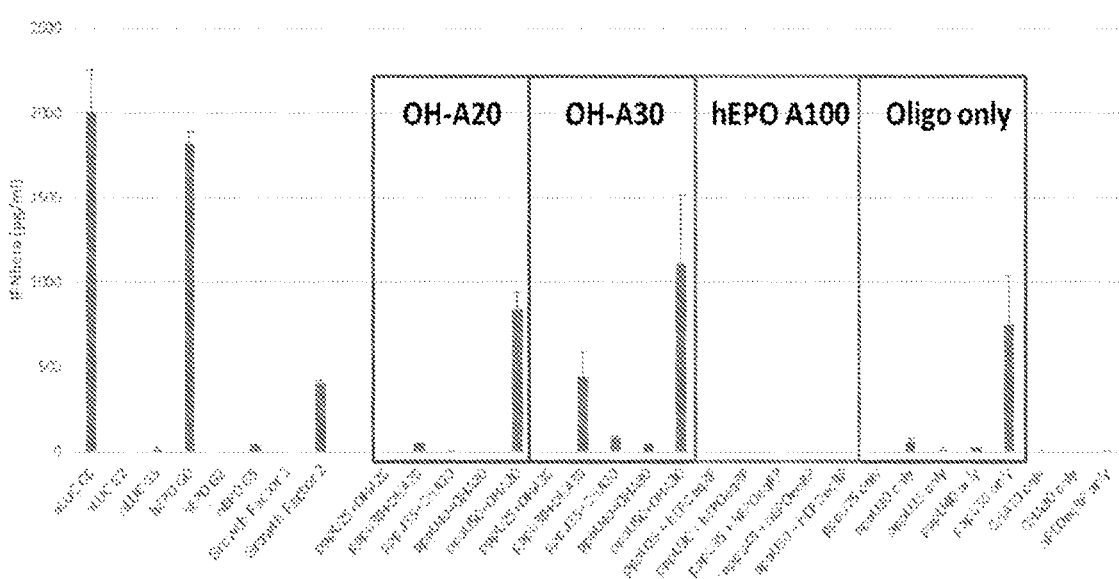
FIG. 29 is a graph depicting in vitro analysis of polyU species.

An In vitro analysis of polyU species was performed to determine what was required for polyU species to simulate an IFNbeta response. ssRNA polyU standards with 5' triphosphate are slightly immunostimulatory. As dsRNA with OH-F30 (30 bp duplex), there was an additive CK response. However, polyU standards are not immunostimulatory in the presence of full length mRNA (A100) (FIG. 29).

Figure 30:
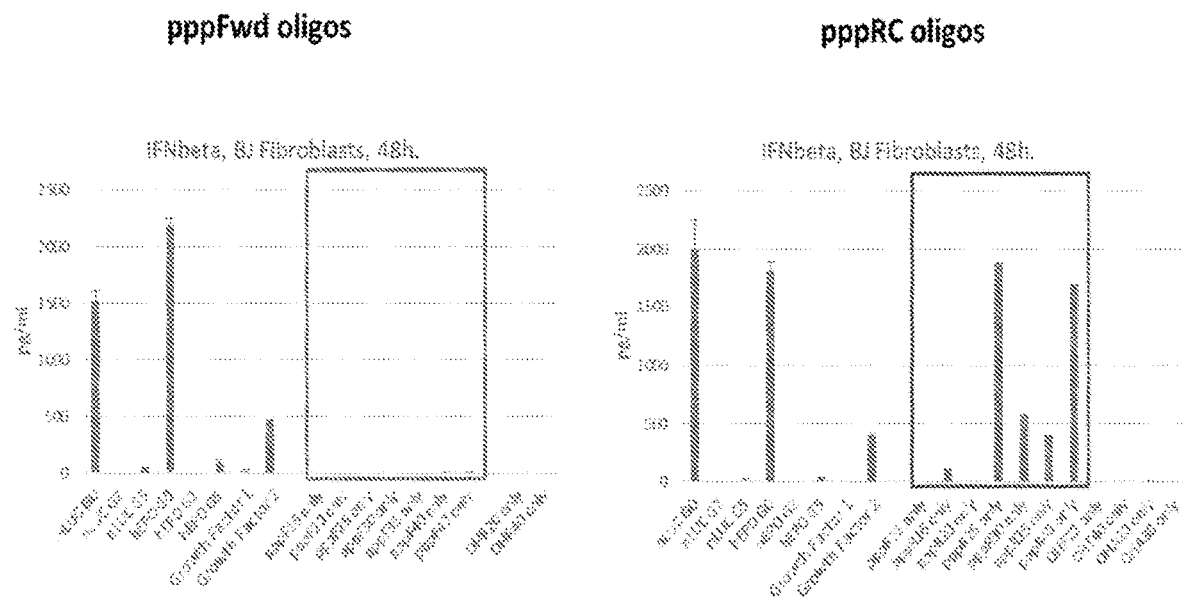
FIG. 30 is a graph depicting in vitro analysis of ssRNA oligo standards.

An in vitro analysis of ssRNA oligonucleotide standards was performed to determine what was the IFNbeta response for ssRNA standards. (F or forward oligos represent abortive or truncated species; R or RC or reverse complement oligos represent reverse complement species generated by RNA-templated transcription). Forward oligos with 5' triphosphate are do not stimulate IFNbeta. Reverse complement oligos with 5' triphosphate stimulate IFNbeta at >25 nt in length (FIG. 30).

Figure 31:
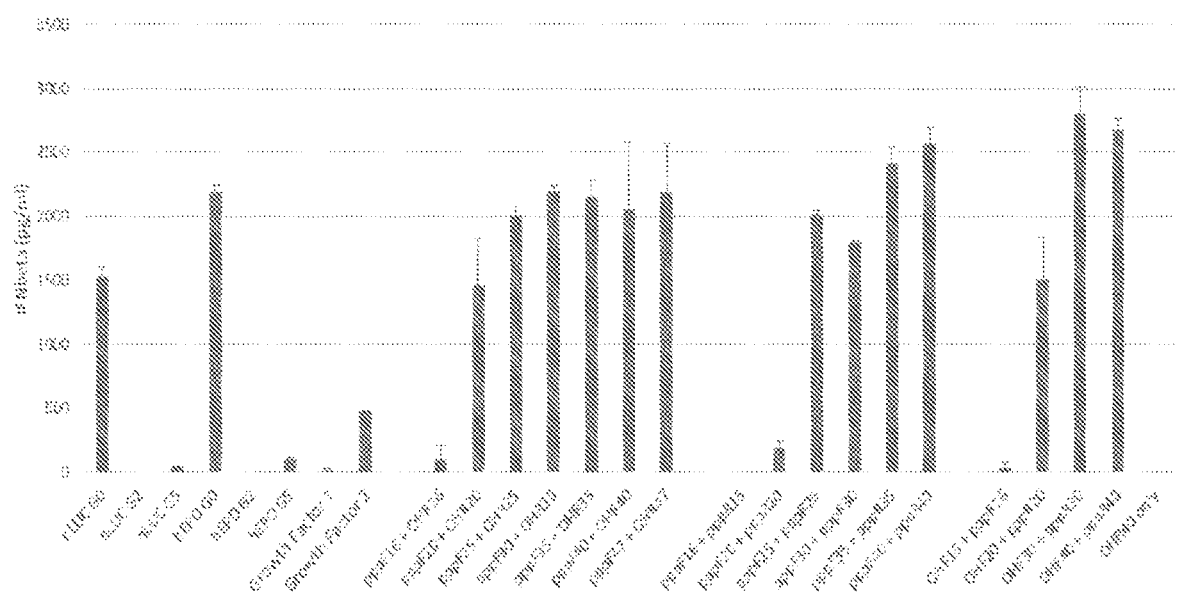
FIG. 31 is a graph depicting in vitro analysis of dsRNA oligos standards with different 5' functionalities.

An in vitro analysis of dsRNA oligos standards with different 5' functionalities was performed to determine whether the 5' functionality (triphosphate vs hydroxyl) affect IFNbeta response. 5' triphosphate on F oligo and 5' hydroxyl on RC oligo simulates IFNbeta at >20 bp. 5' triphosphate on F oligo and 5' triphosphate on RC oligo simulates IFNbeta at >25 bp. 5' hydroxyl on F oligo and 5' triphosphate on RC oligo stimulates IFNbeta at >20 bp. Only one trisphosphate was necessary to simulate IFNbeta at >20 bp (FIG. 31).

Figure 32:
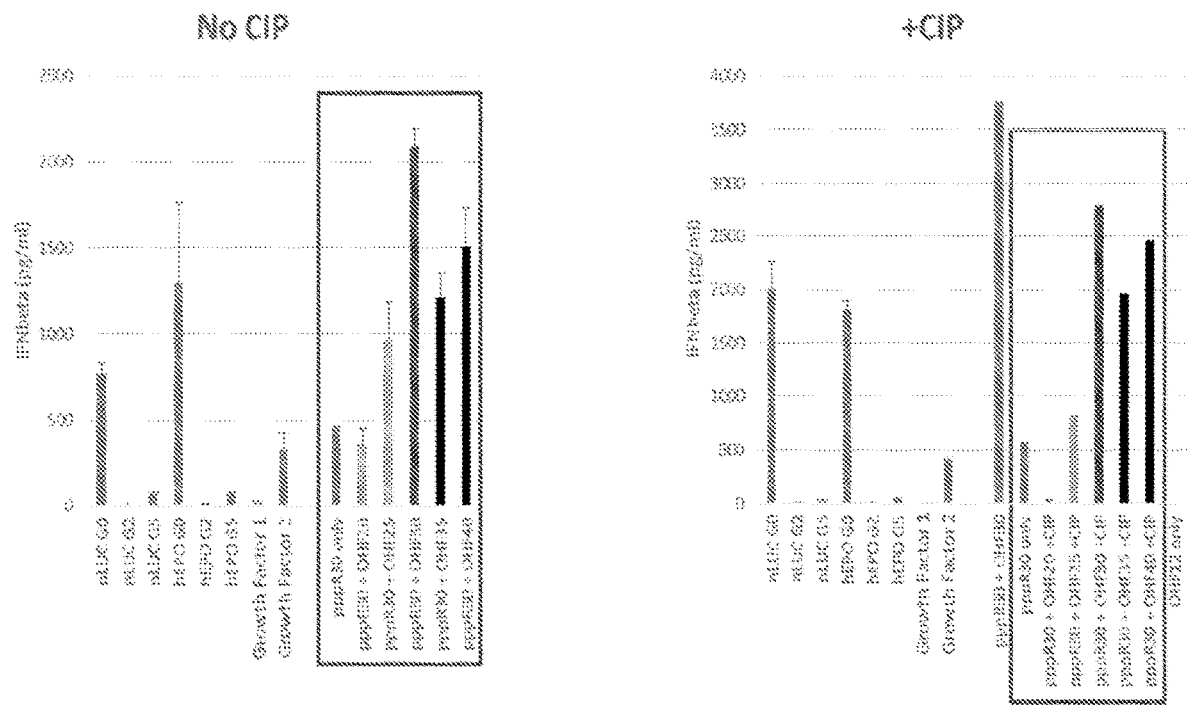
FIG. 32 is a graph demonstrating that phosphatase cannot dephosphorylate dsRNA.

An IFNbeta analysis of CIP-treated dsRNA oligo standards was performed. dsRNA oligo standards of varying overhang lengths were treated with CIP and IFNbeta response was analyzed. Samples in which dephosphorylation (i.e. 5' overhang) was observed by LCMS (FIG. 19) did not stimulate IFNbeta much as the untreated sample. Samples that were not dephosphorylated by CIP (i.e. perfect duplex and 3' overhang) had no change in IFNbeta response +/−CIP (FIG. 32).

Figure 33:
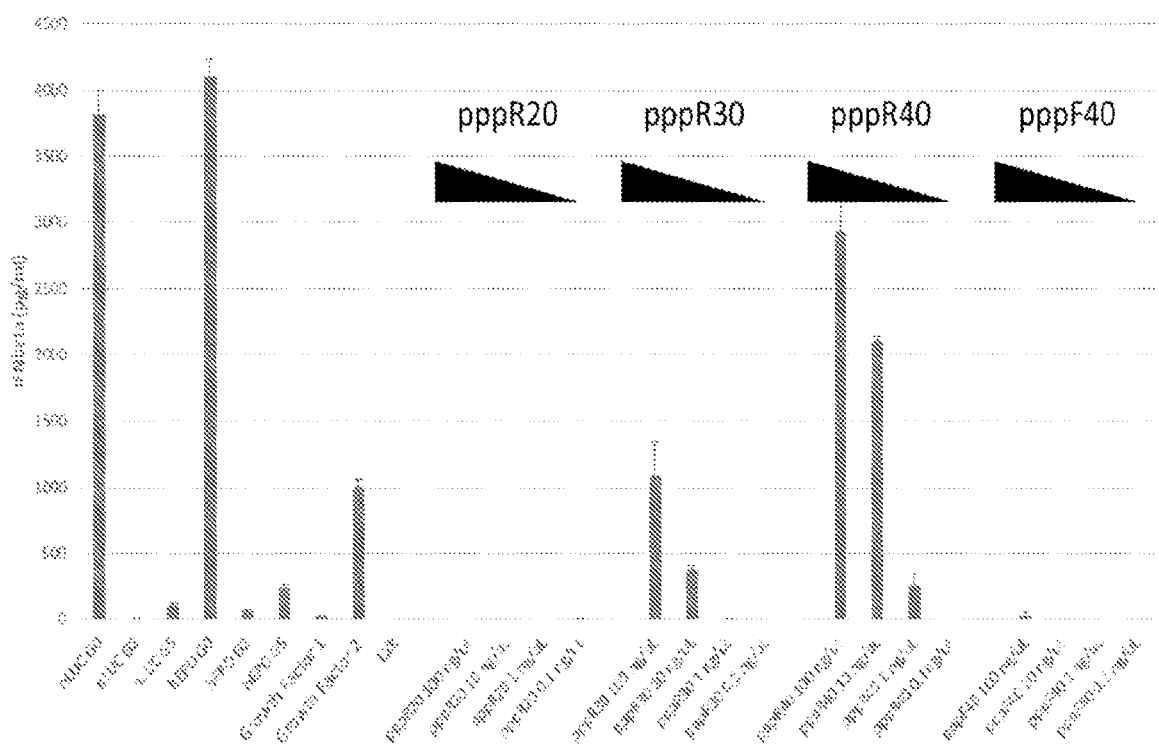
FIG. 33 is a graph demonstrating the ssRNA Impurity Dose Response (IFNbeta in BJ Fibroblasts).

A ssRNA Impurity Dose Response (IFNbeta in BJ Fibroblasts) was performed to determine what was the dose dependence of ssRNA impurity standards in vitro (BJF, IFNbeta). How much of any one type of impurity was required to stimulate a response. <20 mer ssRNA (RC) was not hot. >30 mer ssRNA (RC) stimulated IFNbeta at about >1 ng/uL (or >2.5 ng/transfection). There was an apparent length dependence to ssRNA CK response (RC). The longer the oligo, the higher the CK response (FIG. 33).

Figure 34:
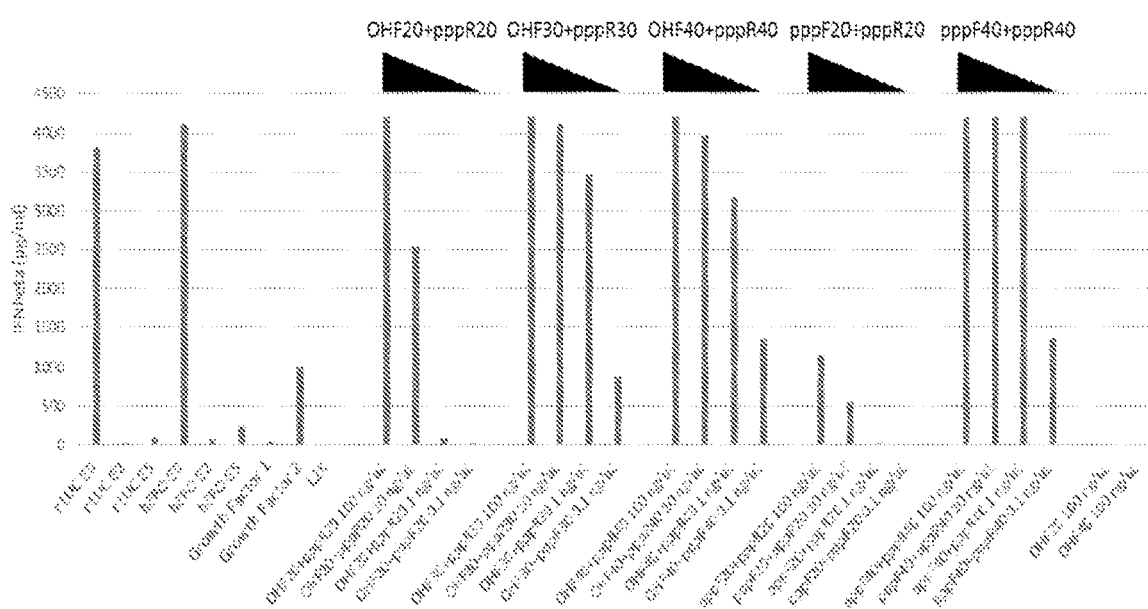
FIG. 34 is a graph demonstrating the dsRNA Impurity Dose Response (IFNbeta in BJ Fibroblasts).

A dsRNA Impurity Dose Response (IFNbeta in BJ Fibroblasts) was performed to determine whether the dose dependence of dsRNA impurity standards in vitro (BJF, IFNbeta). 20-30 bp dsRNA stimulates IFNbeta at ~1 ng/uL (>2.5 ng/transfection). >30 bp dsRNA stimulates IFNbeta at ~0.1 ng/uL (>0.25 ng/transfection). >1000× dilution of >30 bp dsRNA was required to silence IFNbeta response . . . indicating that just a few molecules of these impurities was enough to stimulate a response. There was an apparent length dependence to dsRNA CK response . . . the longer the duplex, the higher the CK response (FIG. 34).

Figure 35:
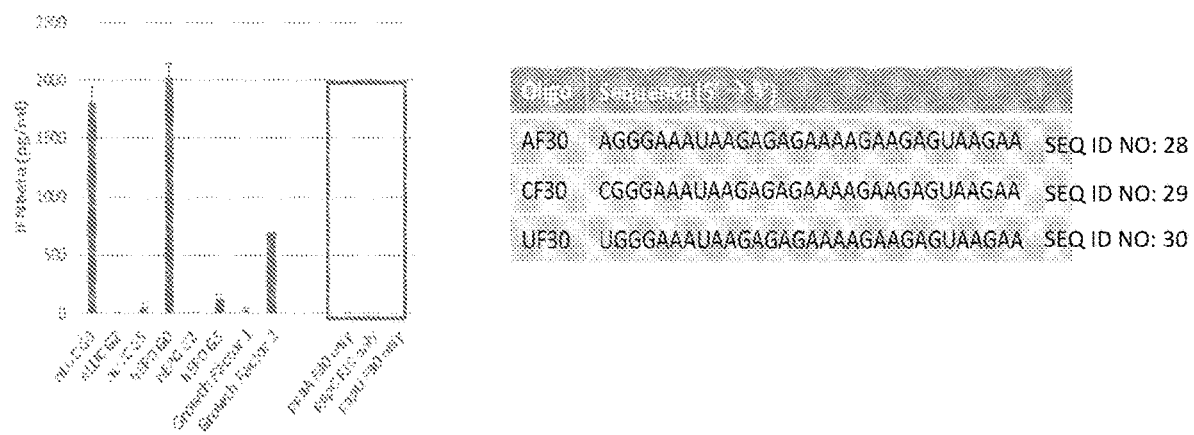
FIG. 35 is a graph demonstrating the IFNbeta Response for modified 5' nucleotide on Forward Oligo Standards.

An IFNbeta Response for modified 5' nucleotide on Forward Oligo Standards was performed to determine whether the 5' nucleotide (trisphosphorylated) affect CK response. When a 5'A/C/U was added to the F oligos, was a CK response induced. 5' non-G does not change IFNbeta response (still cold). This suggests that there was a sequence dependence (since RCs are hot) (FIG. 35).

Figure 36:
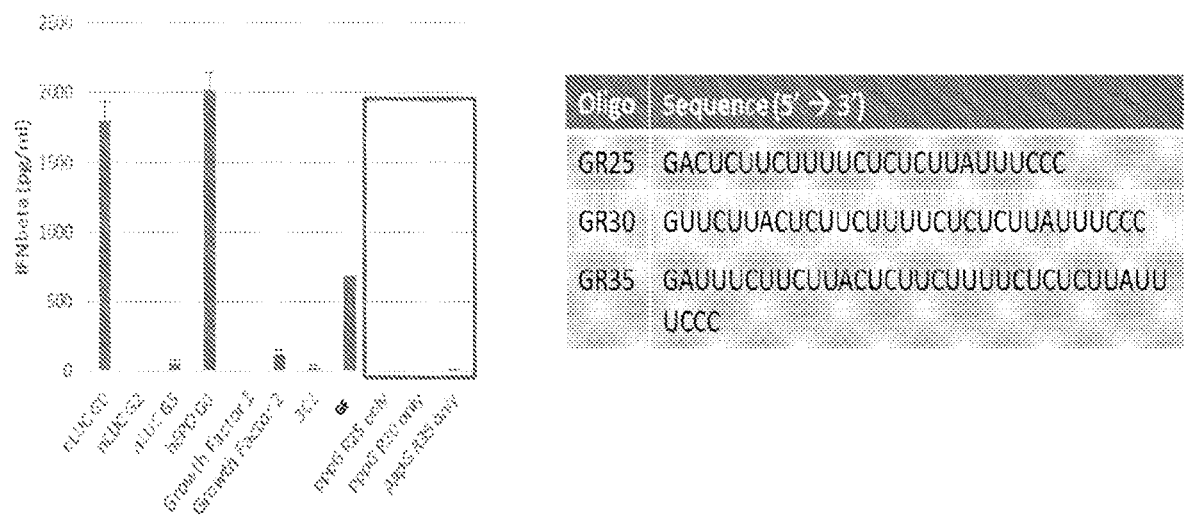
FIG. 36 is a graph demonstrating the IFNbeta Response for modified 5' nucleotide on Reverse Complement Oligo Standards.

An IFNbeta Response for modified 5' nucleotide on Reverse Complement Oligo Standards was performed to determine whether the 5' nucleotide (trisphosphorylated) affect CK response. When a 5'G was added to the RC oligos, was a CK response induced. 5' pppG on RC oligos SILENCES IFNbeta response. This suggests that no matter what the sequence identity was, a 5' G will silence the CK response (FIG. 36).

Figure 37:
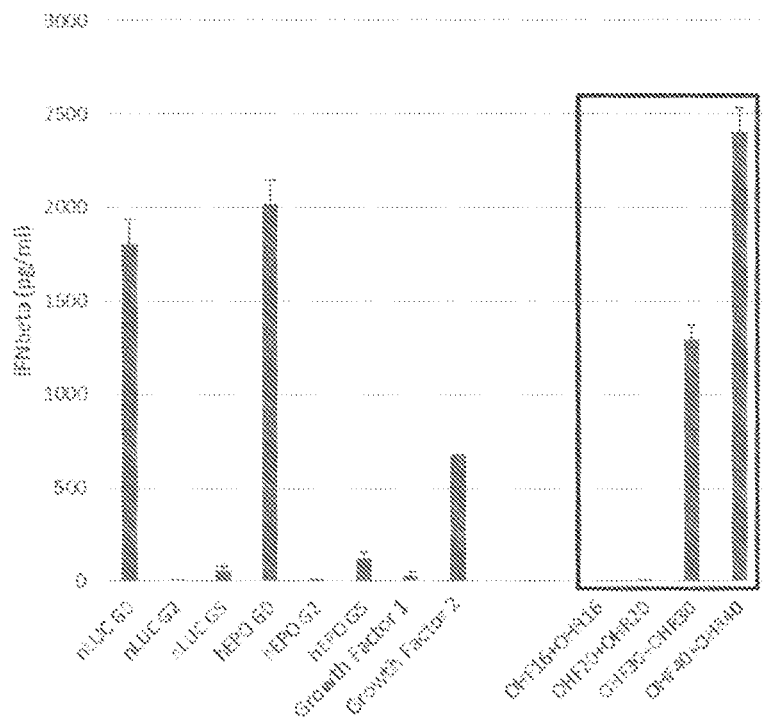
FIG. 37 is a graph demonstrating the IFNbeta Response for 5' hydroxyl functionalized dsRNA.

An IFNbeta Response for 5' hydroxyl functionalized dsRNA was performed to determine how much does the 5' functionality (ppp vs OH) affect cytokine response in dsRNA. 5' ppp-F/5'ppp-RC duplex to 5'OH-F/5'OH-RC were tested. There was an IFNbeta response for >30 bp dsRNA with either 5' ppp or 5' OH. This suggests that dsRNA >30 bp, no matter what the 5' functionality was, stimulated a IFNbeta response in BJFs (FIG. 37).

Implications

RNA templated transcription as an IVT byproduct was reduced greatly and nearly eliminated with the alpha reaction process. As a result of mitigating the formation of reverse complements, both impurities of interest are addressed: dsRNA (with 5'ppp) and RNAs initiating with non-pppG (pppA, pppC, and pppU).

RNA templated transcription was enhanced at IVT reaction temperatures less than 37° C. (for example, at 25° C.). The ramp time to achieve 37° C. heating while IVT reaction was underway, can lead to higher impurity levels, especially as 25° C. to 37° C. time ramp increases. The alpha reaction process was more forgiving at 25° C., as trace RNA templated transcription species were detected at ambient temperature.

RP was more effective with alpha reaction than with the equimolar process. There was a lower impurity load with alpha reaction, which leads to improved separations. One can solve for "purity" more explicitly and may potentially increase load challenge, increasing the productivity. A single RP cycle was adequate to knock an unmodified species to baseline using GDP alpha reaction, while two to three sequence RP cycles are required to get two fractions of an unmodified species using equimolar IVT.

Figure 38:
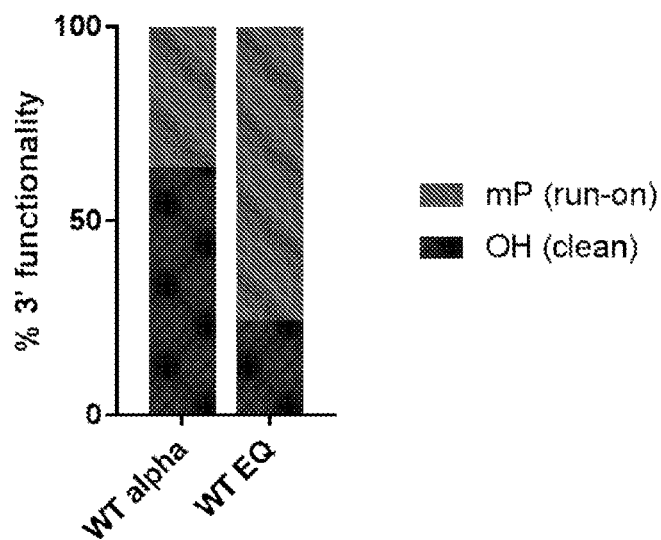
FIG. 38 is a graph demonstrating that that alpha process generates more OH (clean) than equimolar process.

Example 5. RNA Generated with Alpha Process has <40% Run-on Transcripts hEPO RNA was generated using equimolar or alpha processes. RNA was digested with Rnase T1 and the tail fragment was analyzed by LCMS. A tail fragment with a 3' mP indicates a run-on transcript. The alpha process generated a 3'OH (clean) calculated to be 32780 Da and a 5'OH/3'mP (run-on) calculated to be 32860 Da. The equimolar process generated a 5'OH/3'mP (run-on) of 32861 Da and a much smaller amount of 3'OH (clean) (FIG. 38).

Example 6. Total Digestion Indicates that RNA from Equimolar Process has a Higher Abundance of Non-GTP 5' Nucleotide than RNA Made with Alpha Processes Short open reading frame RNA was generated using four different conditions: 37° C. 2 hours (standard) versus 25° C. 6 hours and equimolar versus alpha. Each RNA was enzymatically digested to single nucleotides, then the 5' nucleotide abundance was analyzed by LCMS (e.g. pppG or GTP, pppA or ATP, etc.). A 5' G is the first templated nucleotide, which means that if an impure RNA population was generated then there would be a large fraction of 5' nucleotides as ATP, CTP, or UTP (e.g. equimolar processes), and if a pure RNA population was generated then the majority of 5' nucleotides would be GTP (e.g. alpha processes).

Example 7. Short Open Reading Frame RNA Generated by Alpha Processes Generates Fewer Reverse Complements Short open reading frame RNA was generated in G0 (wild type) and G5 ($m^1\Psi$) chemistries using equimolar or alpha processes containing either 32P-GTP or 32P-CTP. 32P-GTP labels abortive transcripts and 32P-CTP labels reverse complement transcripts. There was no difference in abortive or RC profiles between G0 and G5 chemistries. Equimolar and alpha processes have similar abortive profiles. The equimolar process generates more reverse complements than the alpha process.

Example 8. RNase T1 Digestion Informs Run-on Transcript Populations

RNase T1 is an endonuclease that specifically cleaves RNA after guanosine nucleotides, leaving a 5' hydroxide and a 3' monophosphate. For constructs that contain a templated guanosine nucleotide at the 3' end, RNase T1 can be used to distinguish populations of run-on transcripts, which leave a 3' monophosphate, compared to clean transcripts, which contain a 3' hydroxide. hEPO RNA was generated using equimolar or alpha processes then digested with RNase T1 and analyzed by mass spectrometry. The 3' oligo fragment was analyzed and quantified for its 3' heterogeneity. RNA generated with equimolar process contains approximately 70-80% run-on transcripts, while RNA generated with alpha process contains 30-40% run-on transcripts.

Example 9. Total Digestion of RNA to Determine Sample Purity

A short model RNA construct (surrogate RNA 1) was generated using equimolar or alpha processes at 37° C. or 25° C. incubation. Each sample was purified by oligo dT resin to remove unreacted NTPs. Each sample was enzymatically digested to single nucleotides using S1 and benzonase nucleases. The abundances of 5' nucleotides, which are triphosphorylated at the 5' end, were analyzed by mass spectrometry. Extracted ion peaks were integrated and % NTP abundances are tabulated in Table 5. Since 5' GTP is the first templated nucleotide, a pure RNA population is indicated by a high % GTP value. Likewise, an impure RNA population is indicated by a relatively low abundance of GTP. Samples generated using the EQ process have >5% non-GTP 5' nucleotides, while samples generated using alpha process have <5% non-GTP 5' nucleotides.

TABLE 5

|  | % GTP | % ATP | % CTP | % UTP |
|---|---|---|---|---|
| Surrogate RNA 1 equimolar 37° C. | 94.4 | 0.8 | 3.8 | 1.2 |
| Surrogate RNA 1 alpha 37° C. | 97.4 | 0.3 | 2.3 | 0.0 |
| Surrogate RNA 1 equimolar 25° C. | 68.1 | 5.0 | 12.3 | 21.6 |
| Surrogate RNA 1 alpha 25° C. | 97.6 | 0.2 | 1.9 | 0.4 |

Figure 39:
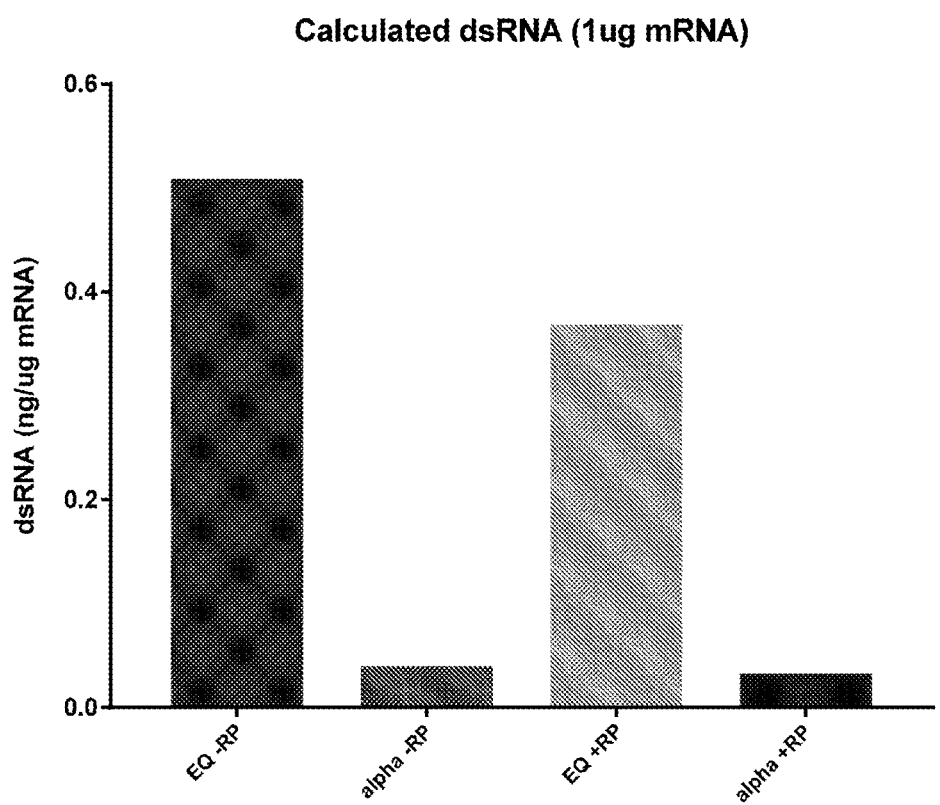
FIG. 39 is a graph showing calculated dsRNA for 1 ug mRNA.

Example 10. dsRNA ELISA Indicates Presence of dsRNA hEPO RNA construct was generated using equimolar or alpha processes and purified either by oligo dT resin only (−RP) or with reverse phase purification (+RP). ELISA using dsRNA-specific antibodies is used to determine relative differences in the purities of RNAs generated using different processes. RNAs generated using equimolar process contain significantly more dsRNA than RNAs generated with alpha process (FIG. 39). Reverse phase purification improves the purities of −RP RNAs.

Example 11. Radioactive Sequencing Gel Analysis Determines Sample Purity

A short model RNA construct (surrogate RNA 1) was generated using equimolar or alpha processes. Each IVT reaction contained either $^{32}$P-GTP, which labels abortive transcripts, or $^{32}$P-CTP, which labels reverse complement transcripts. RNA samples were analyzed by sequencing gel. Based on the $^{32}$P-GTP data, there is no difference in abortive transcript abundance between the two processes. Based on the $^{32}$P-CTP data, equimolar process generates more reverse complements than alpha process.

Example 12. In Vivo Analysis of dsRNA Doped into mRNA

Reverse phase purified hEPO mRNA was doped with 5%, 0.5% or 0.05% w/w 60 bp dsRNA, which corresponds to the first 60 nucleotides of the intact hEPO construct. The mRNA samples were formulated in MC3 then dosed by IV into C57BL/6 and Balb-c mice at 0.5 mpk. After 24 hours, the spleens were harvested and homogenized to generate single cell suspensions. The splenic cells were stained for B cell markers then analyzed by flow cytometry. The activated B cell populations were analyzed based on their expression of CD86 and CD69 markers. The 60 bp dsRNA has the following sequence:

```
60mer 5' UTR Epo F
GGGAAAUAAGAGAGAAAAGAAGAGUAAGAAGAAAUAUAAGAGCCACCAU
GGGAGUGCACG 60mer 5' UTR Epo R
CGUGCACUCCCAUGGUGGCUCUUAUAUUUCUUCUUACUCUUCUUUUCUC
UCUUAUUUCCC
```

Groups that received hEPO mRNA generated by alpha process had lower B cell activation than groups that received hEPO with doped dsRNA. Serum was also collected at 6 h and analyzed by a cytokine luminex panel. The expression trends for IP-10, IFN-gamma, and IFN-alpha markers from the luminex panel were consistent with the trends from the B cell activation analysis, indicating the dsRNA in the doped samples triggered the type I interferon pathway, which led to B cell activation.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

---

What is claimed is:

1. A method of producing a messenger ribonucleic acid (mRNA) that comprises an open reading frame encoding a vaccine antigen, the method comprising incubating a reaction mixture comprising a deoxyribonucleic acid (DNA), an RNA polymerase, nucleoside triphosphates (NTPs), and buffer,
   wherein the NTPs comprise adenosine triphosphate (ATP), cytidine triphosphate (CTP), uridine triphosphate (UTP), and guanosine triphosphate (GTP), or an analog of each respective NTP, and
   wherein the reaction mixture comprises the GTP or an analogue thereof in an amount greater than an amount of one or more of the other NTPs or analogues thereof, thereby producing a composition comprising the mRNA.

2. The method of claim 1, wherein the amount of the GTP or an analogue thereof is greater than an amount of the UTP or an analogue thereof.

3. The method of claim 1, wherein the amount of the GTP is greater than the amount of the UTP.

4. The method of claim 3, wherein an amount of the ATP is greater than the amount of the UTP, and the amount of the CTP is greater than the amount of the UTP.

5. The method of claim 1, wherein the reaction mixture comprises an at least 2:1 ratio of GTP concentration to ATP concentration, an at least 2:1 ratio of GTP concentration to CTP concentration, and an at least 4:1 ratio of GTP concentration to UTP concentration.

6. The method of claim 1, wherein the reaction mixture comprises a 2:1 ratio of GTP concentration to ATP concentration, a 2:1 ratio of GTP concentration to CTP concentration, and a 4:1 ratio of GTP concentration to UTP concentration.

7. The method of claim 1, wherein the reaction mixture further comprises guanosine diphosphate (GDP).

8. The method of claim 1, wherein the reaction mixture comprises an at least 3:1 ratio of GTP plus GDP concentration to ATP concentration, an at least 6:1 ratio of GTP plus GDP concentration to CTP concentration, and an at least 6:1 ratio of GTP plus GDP concentration to UTP concentration.

9. The method of claim 1, wherein the RNA polymerase is selected from T7 polymerase, T3 polymerase, and SP6 polymerase.

10. The method of claim 9, wherein the RNA polymerase is T7 polymerase.

11. The method of claim 1, wherein the DNA is cDNA.

12. The method of claim 1, wherein the buffer comprises magnesium.

13. The method of claim 12, wherein the reaction mixture further comprises dithiothreitol (DTT).

14. The method of claim 13, wherein the reaction mixture further comprises spermidine.

15. The method of claim 14, wherein the reaction mixture further comprises an RNase inhibitor.

16. The method of claim 14, wherein the reaction mixture further comprises pyrophosphatase.

17. The method of claim 1, wherein the reaction mixture is incubated at 25 degrees Celsius or at 37 degrees Celsius.

18. The method of claim 1, wherein the produced mRNA is less immunogenic than an mRNA made by a comparable method but with equimolar amounts of the NTPs in the reaction mixture.

19. The method of claim 1, wherein the produced mRNA has less double stranded impurities than an mRNA made by a comparable method but with equimolar amounts of the NTPs in the reaction mixture.

20. The method of claim 1, wherein the reaction mixture does not contain an RNase inhibitor.

21. The method of claim 1, wherein less than 1% of the total mass of RNA in the composition is a reverse complement transcription product.

22. The method of claim 21, wherein less than 0.1% of the total mass of RNA in the composition is a reverse complement transcription product.

23. A method of producing a messenger ribonucleic acid (mRNA) that comprises an open reading frame encoding a therapeutic protein or peptide, the method comprising incubating a reaction mixture comprising a deoxyribonucleic acid (DNA), an RNA polymerase, nucleoside triphosphates (NTPs), and buffer,
   wherein the NTPs comprise adenosine triphosphate (ATP), cytidine triphosphate (CTP), uridine triphosphate (UTP), and guanosine triphosphate (GTP), or an analog of each respective NTP, and
   wherein the reaction mixture comprises the GTP or an analogue thereof in an amount greater than an amount of one or more of the other NTPs or analogues thereof, thereby producing a composition comprising the mRNA.

* * * * *